(12) United States Patent
Morrow et al.

(10) Patent No.: US 12,384,801 B2
(45) Date of Patent: Aug. 12, 2025

(54) BENZOTHIOPHENE, THIENOPYRIDINE AND THIENOPYRIMIDINE DERIVATIVES FOR THE MODULATION OF STING

(71) Applicant: CTXT PTY LTD, Melbourne (AU)

(72) Inventors: Benjamin Joseph Morrow, Parkville (AU); Jonathan Grant Hubert, Parkville (AU); Ylva Elisabet Bergman Bozikis, Parkville (AU); Michelle Ang Camerino, Parkville (AU); Anthony Nicholas Cuzzupe, Parkville (AU); Paul Anthony Stupple, Parkville (AU)

(73) Assignee: CTXT PTY LTD., Melbourne (AU)

( * ) Notice: Subject to any disclaimer, the term of this patent is extended or adjusted under 35 U.S.C. 154(b) by 378 days.

(21) Appl. No.: 17/624,134

(22) PCT Filed: Jul. 17, 2020

(86) PCT No.: PCT/EP2020/070334
§ 371 (c)(1),
(2) Date: Dec. 30, 2021

(87) PCT Pub. No.: WO2021/009365
PCT Pub. Date: Jan. 21, 2021

(65) Prior Publication Data
US 2022/0389032 A1   Dec. 8, 2022

(30) Foreign Application Priority Data
Jul. 18, 2019  (GB) ...................................... 1910305

(51) Int. Cl.
  *C07D 519/00*  (2006.01)
  *C07D 409/14*  (2006.01)
(52) U.S. Cl.
  CPC ......... *C07D 519/00* (2013.01); *C07D 409/14* (2013.01)
(58) Field of Classification Search
  CPC .................................................. C07D 519/00
  See application file for complete search history.

(56) References Cited

FOREIGN PATENT DOCUMENTS

WO   WO-2019219820 A1 *  11/2019   .............. A61P 35/00

OTHER PUBLICATIONS

Abraham, Robert T., "Phosphatidylinositol 3-kinase related kinases," Current Opinion in Immunology, Jun. 1996, vol. 8, Issue 3, pp. 412-418.
Aguirre et al., "DENV Inhibits Type I IFN Production in Infected Cells by Cleaving Human STING," PLOS Pathogens, Oct. 2012, vol. 8, Issue 10, pp. 1-14.
Ashby, M. N., "CaaX converting enzymes," Current Opinion in Lipidology, Apr. 1998, vol. 9, No. 2: 99-102, pp. 1-7.
Berge et al., "Pharmaceutical Salts," Journal of Pharmaceutical Sciences, Jan. 1977, vol. 66, No. 1, pp. 1-19.
Bolen et al., "Leukocyte Protein Tyrosine Kinases: Potential Targets for Drug Discovery," Annual Review of Immunology, 1997, vol. 15, pp. 371-404.
Brekken et al., "Selective Inhibition of Vascular Endothelial Growth Factor (VEGF) Receptor 2 (KDR/Flk-1) Activity by a Monoclonal Anti-VEGF Antibody Blocks Tumor Growth in Mice," Cancer Research, Sep. 2000, vol. 60, pp. 5117-5124.
Brodt et al., "Inhibition of the type I insulin-like growth factor receptor expression and signaling: Novel strategies for antimetastatic therapy," Biochemical Pharmacology, Oct. 2000, vol. 60, Issue 8, pp. 1101-1107.
Cai et al., "The cGAS-cGAMP-STING Pathway of Cytosolic DNA Sensing and Signaling," Molecular Cell, Apr. 2014, vol. 54, Issue 2, pp. 289-296.
Canman et al., "The role of ATM in DNA damage responses and cancer," Oncogene, Dec. 1998, vol. 17, No. 25, pp. 3301-3308.
Chen et al., "SARS coronavirus papain-like protease inhibits the type I interferon signaling pathway through interaction with the STING-TRAF3-TBK1 complex," Protein & Cell, May 2014, vol. 5, Issue 5, pp. 369-381.
Cirulli et al., "Exome sequencing in amyotrophic lateral sclerosis identifies risk genes and pathways," Science, Mar. 2015, vol. 347, Issue 6229, pp. 1436-1441.
Collins et al., "Cyclic GMP-AMP Synthase is an Innate Immune DNA Sensor for *Mycobacterium tuberculosis*," Cell Host & Microbe, Jun. 2015, vol. 17, pp. 820-828.
Conlon et al., "Mouse, but not Human STING, Binds and Signals in Response to the Vascular Disrupting Agent 5,6-Dimethylxanthenone-4-Acetic Acid," The Journal of Immunology, May 2013, vol. 190, Issue 10: 5216-5225, pp. 1-11.
Crow et al., "Mutations in the gene encoding the 3'-5' DNA exonuclease TREX1 cause Aicardi-Goutières syndrome at the AGS1 locus," Nature Genetics, Aug. 2006, vol. 38, No. 8, pp. 917-920.
Diner et al., "The Innate Immune DNA Sensor cGAS Produces a Noncanonical Cyclic Dinucleotide that Activates Human STING," Cell Reports, May 2013, vol. 3, pp. 1355-1361.

(Continued)

*Primary Examiner* — David K O'Dell
(74) *Attorney, Agent, or Firm* — Thomas | Horstemeyer, LLP

(57) ABSTRACT

A compound of formula (I): wherein: Y is $(CH_2)_n$, where n is from 2 to 4; W1 and W11 are independently selected from OH and ORP, where RP is Me or Et.

17 Claims, No Drawings

(56) References Cited

OTHER PUBLICATIONS

Ding et al., "Hepatitis C virus NS4B blocks the interaction of STING and TBK1 to evade host innate immunity," Journal of Hepatology, Jul. 2013, vol. 59, pp. 52-58.
Dubensky et al., "Rationale, progress and development of vaccines utilizing STING-activating cyclic dinucleotide adjuvants," Therapeutic Advances in Vaccines, Sep. 2013, vol. 1, No. 4, pp. 131-143.
Freischmidt et al., "Haploinsufficiency of TBK1 causes familial ALS and fronto-temporal dementia," Nature Neuroscience, May 2015, vol. 18, No. 5, pp. 631-638.
Gao et al., "Cyclic [G(2',5')pA(3',5')p] is the Metazoan Second Messenger Produced by DNA-Activated Cyclic GMP-AMP Synthase," Cell, May 2013, vol. 153, Issue 5, pp. 1094-1107.
Gao et al., "Cyclic GMP-AMP Synthase is an Innate Immune Sensor of HIV and Other Retroviruses," Science, Aug. 2013, vol. 341, No. 6148, pp. 903-906.
Gao et al., "Structure-Function Analysis of STING Activation by c[G(2',5')pA(3',5')p] and Targeting by Antiviral DMXAA," Cell, Aug. 2013, vol. 154, Issue 4, pp. 748-762.
Green et al., "Monoclonal antibody therapy for solid tumors," Cancer Treatment Reviews, Aug. 2000, vol. 26, Issue 4, pp. 269-286.
Herzner et al., "Sequence-specific activation of the DNA sensor cGAS by Y-form DNA structures as found in primary HIV-1 cDNA," Nature Immunology, Oct. 2015, vol. 16, No. 10, pp. 1025-1035.
Holm et al., "Influenza A virus targets a cGAS-independent STING pathway that controls enveloped RNA viruses," Nature Communications, Feb. 2016, vol. 7, Issue 10680, pp. 1-9.
Huber et al., "Cutting Edge: Type I IFN Reverses Human Th2 Commitment and Stability by Suppressing GATA3," The Journal of Immunology, Jun. 2010, vol. 185, Issue 2, pp. 813-817.
Isaacs et al., "Virus interference. I. The interferon," Proceedings of the Royal Society B: Biological Sciences, Sep. 1957, vol. 147, Issue 927, pp. 258-267.
Ishikawa et al., "STING is an endoplasmic reticulum adaptor that facilitates innate immune signalling," Nature, Oct. 2008, vol. 455, Issue 7219, pp. 674-678.
Ishikawa et al., "STING regulates intracellular DNA-mediated, type I interferon-dependent innate immunity," Nature, Oct. 2009, vol. 461, Issue 7265, pp. 788-792.
Jackson, S. P., "DNA-dependent protein kinase," International Journal of Biochemistry and Cell Biology, Jul. 1997, vol. 29, No. 7, pp. 935-938.
Jin et al., "Identification and Characterization of a Loss-of-Function Human MPYS Variant," Genes and Immunity, Jan. 2011, vol. 12, pp. 263-269.
Jin et al., "MPYS is Required for IFN Response Factor 3 Activation and Type I IFN Production in the Response of Cultured Phagocytes to Bacterial Second Messengers Cyclic-di-AMP and Cyclic-di-GMP," The Journal Immunology, Jan. 2011, vol. 187, No. 5: 2595-2601, pp. 1-8.
Kath, J. C., "Patent focus: inhibitors of tumour cell growth," Expert Opinion on Therapeutic Patents, 2000, vol. 10, Issue 6, pp. 803-818.
Lackey et al., "The discovery of potent cRaf1 kinase inhibitors," Bioorganic and Medicinal Chemistry Letters, Feb. 2000, vol. 10, Issue 3, pp. 223-226.
Lau et al., "DNA tumor virus oncogenes antagonize the cGAS-STING DNA sensing pathway," Science, Sep. 2015, vol. 350, Issue 6260: 568-571, pp. 1-9.
Lemos et al., "Activation of the STING Adaptor Attenuates Experimental Autoimmune Encephalitis," The Journal of Immunology, Jun. 2014, vol. 192, Issue 12, pp. 5571-5578.
Libanova et al., "Cyclic di-nucleotides: new era for small molecules as adjuvants," Microbial Biotechnology, Sep. 2012, vol. 5, No. 2, pp. 168-176.
Liu et al., "RIG-I-Mediated STING Upregulation Restricts Herpes Simplex Virus 1 Infection," Journal of Virology, Oct. 2016, vol. 90, No. 20, pp. 9406-9419.

Ma et al., "Modulation of the cGAS-STING DNA sensing pathway by gammaherpesviruses," PNAS, Jul. 2015, vol. 112, No. 31, pp. E4306-E4315.
Ma et al., "The cGAS-STING Defense Pathway and Its Counteraction by Viruses," Cell Host & Microbe, Feb. 2016, vol. 19, Issue 2, pp. 150-158.
Martínez-Lacaci et al., "RAS transformation causes sustained activation of epidermal growth factor receptor and elevation of mitogen-activated protein kinase in human mammary epithelial cells," International Journal of Cancer, Oct. 2000, vol. 88, Issue 1, pp. 44-52.
McNab et al., "Type I interferons in infectious disease," Nature Reviews Immunology, Feb. 2015, vol. 15, No. 2, pp. 87-103.
Moisan et al., "TLR7 ligand prevents allergen-induced airway hyperresponsiveness and eosinophilia in allergic asthma by a MYD88-dependent and MK2-independent pathway," American Journal of Physiology—Lung Cellular Molecular Physiology, May 2006, vol. 290, Issue 5, pp. L987-L995.
Nitta et al., "Hepatitis C virus NS4B protein targets STING and abrogates RIG-I-mediated type I interferon-dependent innate immunity," Hepatology, Jan. 2013, vol. 57, No. 1, pp. 46-58.
Oliff, A., "Farnesyltransferase inhibitors: targeting the molecular basis of cancer," Biochimica et Biophysica Acta (BBA)—Reviews on Cancer, May 1999, vol. 1423, No. 3, pp. C19-C30.
Persing et al., "Taking toll: lipid A mimetics as adjuvants and immunomodulators," Trends in Microbiology, Oct. 2002, vol. 10, Issue 10, pp. S32-S37.
Philip et al., "Potential for protein kinase C inhibitors in cancer therapy," in: Muggia, F. M., Concepts, Mechanisms, and New Targets for Chemotherapy, New York, Springer Science+Business Media, 1995, pp. 3-27.
Prantner et al., "Stimulator of IFN Gene is Critical for Induction of IFN-β during Chlamydia muridarum Infection," The Journal of Immunology, Mar. 2010, vol. 184, Issue 5, pp. 2551-2560.
Rakoff-Nahoum et al., "Recognition of Commensal Microflora by Toll-Like Receptors is Required for Intestinal Homeostasis," Cell, Jul. 2004, vol. 118, Issue 2, pp. 229-241.
Ramanjulu et al., "Design of amidobenzimidazole STING receptor agonists with systemic activity," Nature, Dec. 2018, vol. 564, pp. 439-443.
Rosania et al., "Targeting hyperproliferative disorders with cyclin dependent kinase inhibitors," Expert Opinion on Therapeutic Patents, 2000, vol. 10, Issue 2, pp. 215-230.
Scharovsky et al., "Inhibition of ras Oncogene: A Novel Approach to Antineoplastic Therapy," Journal of Biomedical Science, Jan. 2000, vol. 7, No. 4, pp. 292-298.
Sharma et al., "Innate Immune Recognition of an AT-Rich Stem-Loop DNA Motif in the Plasmodium falciparum Genome," Immunity, Aug. 2011, vol. 35, No. 2: 194-207, pp. 1-25.
Shawver et al., "Receptor tyrosine kinases as targets for inhibition of angiogenesis," Drug Discovery Today (DDT), Feb. 1997, vol. 2, No. 2, pp. 50-63.
Sherif, S., "Syntheses with heterocyclic β-enaminonitriles: A facile preparation of polyfunctionally substituted thiophene, thieno[3,2-b]pyridine and thieno[3,2-d]pyrimidine derivatives," Chemical Monthly, Aug. 1996, vol. 127, pp. 955-962.
Sinha et al., "Implications for Src Kinases in Hematopoiesis: Signal Transduction Therapeutics," Journal of Hematotherapy and Stem Cell Research, Oct. 1999, vol. 8, pp. 465-480.
Stern, D. F., "Tyrosine kinase signalling in breast cancer: ErbB family receptor tyrosine kinases," Breast Cancer Research, Mar. 2000, vol. 2, No. 3: 176-183, pp. 1-8.
Stetson et al., "Trex1 Prevents Cell-Intrinsic Initiation of Autoimmunity," Cell, Aug. 2008, vol. 134, Issue 4: 587-598, pp. 1-21.
Storek et al., "cGAS and Ifi204 Cooperate to Produce Type I IFNs in Response to Francisella Infection," The Journal of Immunology, Apr. 2015, vol. 194, Issue 7: 3236-3245, pp. 1-11.
Sun et al., "Coronavirus Papain-like Proteases Negatively Regulate Antiviral Innate Immune Response through Disruption of STING-Mediated Signaling," PLOS One, Feb. 2012, vol. 7, Issue 2: e30802, pp. 1-11.

(56) References Cited

OTHER PUBLICATIONS

Wassermann et al., "*Mycobacterium tuberculosis* Differentially Activates cGAS- and Inflammasome-Dependent Intracellular Immune Responses through ESX-1," Cell Host & Microbe, Jun. 2015, vol. 17, Issue 6, pp. 799-810.

Watson et al., "The Cytosolic Sensor cGAS Detects *Mycobacterium tuberculosis* DNA to Induce Type I Interferons and Activate Autophagy," Cell Host & Microbe, Jun. 2015, vol. 17, Issue 6, pp. 811-819.

Wu et al., "Inhibition of cGAS DNA Sensing by a Herpesvirus Virion Protein," Cell Host Microbe, Sep. 2015, vol. 18, Issue 3: 333-344, pp. 1-26.

Yamamoto et al., "Ras-Induced Transformation and Signaling Pathway," The Journal of Biochemistry, Nov. 1999, vol. 126, Issue 5, pp. 799-803.

Yi et al., "Single Nucleotide Polymorphisms of Human STING Can Affect Innate Immune Response to Cyclic Dinucleotides," PLOS One, Oct. 2013, vol. 8, Issue 10: e77846, pp. 1-16.

Zhong et al., "Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics," Cancer Research, Mar. 2000, vol. 60, Issue 6, pp. 1541-1545.

Zitvogel et al., "Type I interferons in anticancer immunity," Nature Reviews Immunology, Jul. 2015, vol. 15, pp. 405-414.

\* cited by examiner

BENZOTHIOPHENE, THIENOPYRIDINE AND THIENOPYRIMIDINE DERIVATIVES FOR THE MODULATION OF STING

BACKGROUND TO THE INVENTION

Vertebrates are constantly threatened by the invasion of microorganisms and have evolved mechanisms of immune defense to eliminate infective pathogens. In mammals, this immune system comprises two branches; innate immunity and adaptive immunity. The innate immune system is the first line of defense which is initiated by Pattern Recognition Receptors (PRRs) which detect ligands from the pathogens as well as damage associated molecular patterns (Takeuchi 2010). A growing number of these receptors have been identified including Toll-like receptors (TLRs), C-type lectin receptors, retinoic acid inducible gene I (RIG-I)-like receptors and NOD-like receptors (NLRs) and also double stranded DNA sensors. Activation of PRRs leads to up-regulation of genes involved in the inflammatory response including type 1 interferons, pro-inflammatory cytokines and chemokines which suppress pathogen replication and facilitate adaptive immunity.

The adaptor protein STING (Stimulator of Interferon Genes), also known as TMEM 173, MPYS, MITA and ERIS, has been identified as a central signaling molecule in the innate immune response to cytosolic nucleic acids (Ishikawa 2008; WO2013/166000). Activation of STING results in up-regulation of IRF3 and $NF_KB$ pathways leading to induction of type 1 interferons including Interferon-β and other cytokines. STING is critical for responses to cytosolic DNA of pathogen or host origin, and of unusual nucleic acids called Cyclic Dinucleotides (CDNs).

CDNs were first identified as bacterial secondary messengers responsible for controlling numerous responses in the prokaryotic cell. Bacterial CDNs, such as c-di-GMP, are symmetrical molecules characterized by two 3',5' phosphodiester linkages.

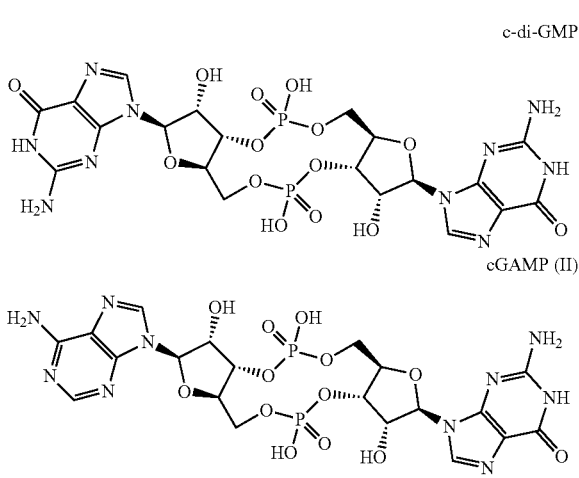

Direct activation of STING by bacterial CDNs has recently been confirmed through X-ray crystallography (Burdette 2013). Bacterial CDNs and their analogues have consequently attracted interest as potential vaccine adjuvants (Libanova 2012; WO2007/054279; WO2005/087238).

More recently, the response to cytosolic DNA has been elucidated and shown to involve generation, by an enzyme called cyclic GMP-AMP synthase (cGAS, previously known as C6orf150 or MB21D1), of a novel mammalian CDN signaling molecule identified as cGAMP, which then activates STING. Unlike bacterial CDNs, cGAMP is an asymmetrical molecule characterized by its mixed 2',5' and 3',5' phosphodiester linkages (Gao 2013A). Interaction of cGAMP (II) with STING has also been demonstrated by X-ray crystallography (Cai 2014).

Interferon was first described as a substance which could protect cells from viral infection (Isaacs 1957). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

Administration of a small molecule compound which could modulate the innate immune response, including the activation or inhibition of type I interferon production and other cytokines, could become an important strategy for the treatment or prevention of human diseases including viral infections and autoimmune disease. This type of immuno-modulatory strategy has the potential to identify compounds which may be useful not only in infectious diseases but also in cancer (Zitvogel 2015), allergic diseases (Moisan 2006), neurodegenerative diseases such as amyotrophic lateral sclerosis and multiple sclerosis (Lemos 2014; Cirulli 2015; Freischmidt 2015), other inflammatory conditions such as irritable bowel disease (Rakoff-Nahoum 2004), and as vaccine adjuvants (Persing 2002; Dubensky 2013).

STING is essential for antimicrobial host defense, including protection against a range of DNA and RNA viruses and bacteria (reviewed in McNab 2015; Ma 2016). Herpesviridae, Flaviviridae, Coronaviridae, Papillomaviridae, Adenoviridae, Hepadnaviridae, ortho- and paramyxoviridae and rhabdoviridae have evolved mechanisms to inhibit STING mediated Type I interferon production and evade host immune control (Holm 2016; Ma 2015; Wu 2015; Liu 2016; Chen 2014; Lau 2013; Ding 2013; Nitta 2013; Sun 2012; Aguirre 2012; Ishikawa 2009). Thus, small molecule activation of STING could be beneficial for treatment of these infectious diseases.

In contrast, increased and prolonged type I IFN production is associated with a variety of chronic infections, including Mycobacteria (Collins 2015; Wassermann 2015; Watson 2015), Franciscella (Storek 2015; Jin 2011A), Chlamydia (Prantner 2010), Plasmodium (Sharma 2011), and HIV (Herzner 2015; Gao 2013B). Similarly, excess type I interferon production is found among patients with complex forms of autoimmune disease. Genetic evidence in humans and support from studies in animal models support the hypothesis that inhibition of STING results in reduced type I interferon that drives autoimmune disease (Crow 2006; Stetson 2008). Therefore, inhibitors of STING provide a treatment to patients with chronic type I interferon and proinflammatory cytokine production associated with infections or complex autoimmune diseases. Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (Huber 2010).

Compounds that bind to STING and act as agonists have been shown to induce type 1 interferons and other cytokines on incubation with human PBMCs. Compounds which induce human interferons may be useful in the treatment of various disorders, for example the treatment of allergic diseases and other inflammatory conditions for example allergic rhinitis and asthma, the treatment of infectious diseases, neurodegenerative disease, pre-cancerous syndromes and cancer, and may also be useful as immugenic composition or vaccine adjuvants. Compounds that bind to STING may act as antagonists and could be useful in the treatment, for example of autoimmune diseases. It is envisaged that targeting STING with activation or inhibiting agents may be a promising approach for preventing and treating diseases and conditions in which modulation for the type 1 IFN pathway is beneficial, including inflammatory, allergic and autoimmune diseases, infectious diseases, cancer, pre-cancerous syndromes and as immugenic compositions or vaccine adjuvants.

Skin cancers and various skin viral infections involve immune privileged environment and activation of local immune response to the lesions may be a topical therapeutic approach. STING agonists may be used for treating viral warts, superficial skin cancers and premalignant actinic keratoses. By a dual mechanism of action, STING activation (e.g., via microneedle patch delivery or topical formulation) may be used to control HPV directly via antiviral type I interferon production and indirectly by enhancing the adaptive immune response downstream of innate immune activation. STING agonist can activate the innate immune response in the lesion and drive the anti-HPV T-cell response.

Recent evidence has indicated that spontaneous activation of the STING pathway within tumor-resident dendritic cells leads to type I IFN production and adaptive immune responses against tumors. Furthermore, activation of this pathway in antigen presenting cells (APCs) within the tumor microenvironment drives the subsequent T-cell priming against tumor-associated antigens (Corrales 2015). International Patent Applications WO2014/093936, WO2014/189805, WO2013/185052, WO2015/077354 and WO2015/185565 disclose certain cyclic di-nucleotides and their use in inducing an immune response via activation of STING.

Additionally non-CDN compounds have been described as active agonists of STING.

Applications WO2019/069269, WO2019/069270, WO2017/175156, and WO2017/175147 and Ramanjulu 2018 describe certain amidobenzimidazole-based and diamidobenzimidazole-based compounds and their use in modulation of STING.

Applications WO2019/027858 and US2018/0093964 describe certain benzo[b]thiophene compounds and their use as agonists of STING. WO2019/195063 describe Aza-benzothiophene compounds, and WO2019/195124 describes benzothiophenes and related compounds and their use as agonists of STING. WO 2019/219820 describes benzothiophenes, thienopyridines and thienopyrimidines as modulators of STING.

Applications WO2018/234808, WO2018/234807, GB2563642A, WO2018/234805 describe certain arylamido compounds and their use as modulators of STING.

STING has known polymorphisms, including alleles encoding histidine at position 232, which are refractory to bis-3',5' (canonical) CDNs, but not 2',5'-3',5' (non-canonical, mixed linkage) CDNs (Diner 2013; Jin 2011B). Single nucleotide polymorphisms in the STING gene have been reported to affect the responsiveness to bacterial-derived canonical CDNs (Diner 2013; Gao 2013C; Conlon 2013). Five major haplotypes of STING have been reported (WT, R232H, HAQ, AQ and Q alleles), which vary at amino acid positions 71, 230, 232 and 293 (Jin 2011B; Yi 2013).

The compounds of this invention modulate the activity of STING, and accordingly, may provide a beneficial therapeutic impact in the prevention and treatment of diseases, disorders and/or conditions in which modulation of STING (Stimulator of Interferon Genes) is beneficial, for example for inflammation, allergic and autoimmune diseases, infectious diseases, cancer, pre-cancerous syndromes and as vaccine adjuvants.

SUMMARY OF THE INVENTION

A first aspect of the present invention provides a compound of formula I:

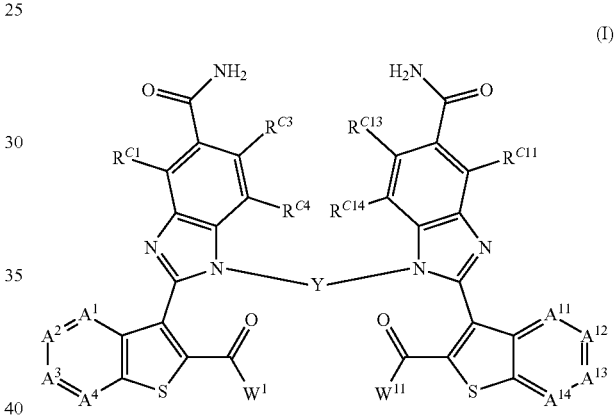

(I)

Y is $(CH_2)_n$, where n is from 2 to 4;
$W^1$ and $W^{11}$ are independently selected from OH and $OR^P$, where $R^P$ is Me or Et;
$A^1$ is $CR^A$ or N;
$A^2$ is $CR^B$ or N;
$A^3$ is $CR^C$ or N;
$A^4$ is $CR^D$ or N;
where no more than two of $A^1$, $A^2$, $A^3$, and $A^4$ may be N;
one or two of $R^A$, $R^B$, $R^C$ and $R^D$, (if present) are selected from H, F, Cl, Br, Me, $CF_3$, cyclopropyl, cyano, OMe, OEt, $CH_2OH$, $CH_2OMe$ and OH;
the remainder of $R^A$, $R^B$, $R^C$ and $R^D$, (if present) are H;
$A^{11}$ is $CR^{AA}$ or N;
$A^{12}$ is $CR^{BB}$ or N;
$A^{13}$ is $CR^{CC}$ or N;
$A^{14}$ is $CR^{DD}$ or N;
where no more than two of $A^{11}$, $A^{12}$, $A^{13}$ and $A^{14}$ may be N;
one or two of $R^{AA}$, $R^{BB}$, $R^{CC}$ and $R^{DD}$, (if present) are selected from H, F, Cl, Br, Me, $CF_3$, cyclopropyl, cyano, OMe, OEt, $CH_2OH$, $CH_2OMe$ and OH;
the remainder of $R^{AA}$, $R^{BB}$, $R^{CC}$ and $R^{DD}$, (if present) are H;
$R^{C1}$, $R^{C3}$ and $R^{C4}$ are independently selected from H, Cl, F, Br, Me, OMe, OEt, cyano, $CF_3$, $CH_2OH$, $CH_2OMe$, $C_{2-4}$ alkenyl and $C_5$heterocyclyl;

$R^{C11}$, $R^{C13}$ and $R^{C14}$ are independently selected from H, Cl, F, Br, Me, OMe, OEt, cyano, $CF_3$, $CH_2OH$, $CH_2OMe$, $C_{2-4}$alkenyl and $C_5$heterocyclyl.

A second aspect of the present invention provides a compound of the first aspect for use in a method of therapy. The second aspect also provides a pharmaceutical composition comprising a compound of the first aspect and a pharmaceutically acceptable excipient.

A third aspect of the present invention provides a method of treatment or prevention of a disease ameliorated by the modulation of STING, comprising administering to a patient in need of treatment, a compound of the first aspect of the invention or a pharmaceutical composition of the second aspect of the invention. The third aspect of the present invention also provides the use of a compound of the first aspect of the invention in the manufacture of a medicament for treating or preventing disease ameliorated by the modulation of STING, and a compound of the first aspect of the invention or pharmaceutical composition thereof for use in the treatment or preventing of disease ameliorated by the modulation of STING.

Definitions $C_{3-6}$ Cycloalkyl: The term "$C_{3-6}$ cycloalkyl" as used herein, pertains to a monovalent moiety obtained by removing a hydrogen atom from a carbon atom of a saturated cyclic hydrocarbon compound having from 3 to 6 carbon atoms. Examples of $C_{3-6}$ cycloalkyl groups include, but are not limited to, cyclopropyl ($C_3$), cyclobutyl ($C_4$), cyclopentyl ($C_5$) and cyclohexyl ($C_6$).

$C_{3-7}$Heterocyclyl: The term "$C_{3-7}$ heterocyclyl" as used herein, pertains to a monovalent moiety obtained by removing a hydrogen atom from a ring atom of a monocyclic heterocyclic compound, which moiety has from 3 to 7 ring atoms; of which from 1 to 2 atoms are heteroatoms, chosen from oxygen or nitrogen.

In this context, the prefixes (e.g. $C_{3-7}$) denote the number of ring atoms, or range of number of ring atoms, whether carbon atoms or heteroatoms.

Examples of $C_{3-7}$ heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), pyrrole ($C_5$), piperidine ($C_6$), dihydropyridine ($C_6$), tetrahydropyridine ($C_6$), pyridine ($C_6$), azepine ($C_7$), azepane ($C_7$);
$N_2$: diazirine ($C_3$) diazetidine ($C_4$), imidazolidine ($C_5$), pyrazolidine (diazolidine) ($C_5$), imidazoline ($C_5$), pyrazoline (dihydropyrazole) ($C_5$), imidazole ($C_5$), pyrazole ($C_5$), piperazine ($C_6$), pyrazine ($C_6$), pyrimidine ($C_6$), pyridazine ($C_6$), diazepine ($C_7$), diazepane ($C_7$);
$O_1$: oxetane ($C_4$), tetrahydrofuran ($C_5$); oxane ($C_6$);
$O_2$: dioxetane ($C_4$), dioxolane ($C_5$); dioxane ($C_6$), dioxole ($C_5$);
$N_1O_1$: tetrahydrooxazole ($C_5$), dihydrooxazole ($C_5$), tetrahydroisoxazole ($C_5$), dihydroisoxazole ($C_5$), isoxazole ($C_5$), oxazole ($C_5$), morpholine ($C_6$), tetrahydrooxazine ($C_6$), dihydrooxazine ($C_6$), oxazine ($C_6$).

$C_{1-4}$ Alkyl: The term "$C_{1-4}$ alkyl" as used herein, pertains to a monovalent moiety obtained by removing a hydrogen atom from a carbon atom of a saturated hydrocarbon compound having from 1 to 4 carbon atoms.

Examples of saturated alkyl groups include, but are not limited to, Me: methyl ($C_1$), Et: ethyl ($C_2$), Pr: propyl ($C_3$), and Bu: butyl ($C_4$).

Examples of saturated linear alkyl groups include, but are not limited to, methyl ($C_1$), ethyl ($C_2$), nPr: n-propyl ($C_3$), and nBu: n-butyl ($C_4$).

Examples of saturated branched alkyl groups include, but are not limited to, iPr: iso-propyl ($C_3$, —$C(CH_3)_2$), iBu: iso-butyl ($C_4$), sBu: sec-butyl ($C_4$) and tBu: tert-butyl ($C_4$).

$C_{2-4}$ Alkenyl: The term "$C_{2-4}$ alkenyl" as used herein, pertains to an alkyl group having from 2 to 4 carbon atoms and having one or more carbon-carbon double bonds.

Examples of unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —$C(CH_3)$=$CH_2$) and butenyl ($C_4$).

$C_{1-4}$ fluoroalkyl: The term "$C_{1-4}$ fluoroalkyl" as used herein, pertains to a $C_{1-4}$alkyl group, substituted with one or more fluorine atoms.

Alkoxy: —OR wherein R is a $C_{1-4}$alkyl group as defined above. It can be represented as —O—$C_{1-4}$ alkyl. Examples of alkoxy groups include, but are not limited to, methoxy (OMe, $C_1$), ethoxy (OEt, $C_2$), propyloxy ($C_3$), and butyloxy ($C_4$).

Alkyl carbamoyl: —NHC(=O)OR wherein R is a $C_{1-4}$alkyl group as defined above. Examples of alkyl carbamoyl groups include, but are not limited to, —N(H)C(=O)$OCH_3$, —N(H)C(=O)$OCH_2CH_3$, and —N(H)C(=O)$OC(CH_3)_3$.

Alkyl carbamoyl ester: —OC(=O)NRR' wherein R and R' are independently selected from H and $C_{1-4}$ alkyl as defined above. Examples of alkyl carbamoyl ester groups include, but are not limited to, —OC(=O)$N(CH_3)_2$, and —OC(=O)N(H)$CH_3$.

Alkyl carboxyl ester: —OC(=O)OR wherein R is a $C_{1-4}$alkyl group as defined above. Examples of alkyl carboxyl ester groups include, but are not limited to, —OC(=O)$OCH_3$, —OC(=O)$OCH_2CH_3$, —OC(=O)$OC(CH_3)_3$, and —OC(=O)$OCH(CH_3)_2$.

Amino: —N(R)R' wherein R and R' are independently selected from H and $C_{1-4}$ alkyl as defined above. Examples of an amino group include, but are not limited to, —$NH_2$, —N(H)$CH_3$, —N(H)$C(CH_3)_2$, —$N(CH_3)_2$, —$N(CH_2CH_3)_2$.

Amido (carbamoyl, carbamyl, aminocarbonyl, carboxamide, aminoacyl):
—C(=O)N(R)R' wherein R and R' are independently selected from H and $C_{1-4}$ alkyl as defined above. Examples of an amido group include, but are not limited to, C(=O)$NH_2$, —C(=O)N(H)$CH_3$, —C(=O)$N(CH_3)_2$, —C(=O)N(H)$CH_2CH_3$, and —C(=O)$N(CH_2CH_3)_2$.

Acylamido: —N(R)C(=O)R' wherein R and R' are independently selected from H and $C_{1-4}$ alkyl as defined above. Examples of an acylamido group include, but are not limited to, —N(H)C(=O)$CH_2CH_3$, —N(H)C(=O)$CH_3$ and —N($CH_3$)C(=O)$CH_3$.

Phenyl: —$C_6H_5$, wherein the phenyl may itself be optionally substituted by one or more $C_{1-4}$alkyl groups, one or more $C_{1-4}$ fluoroalkyl groups, one or more $C_{1-4}$ alkoxy groups, one or more halo substituents and one or more cyano substituents.

Benzyl: —$CH_2$-Phenyl, wherein phenyl is as defined above.

Ester (carboxylate, carboxylic acid ester, oxycarbonyl): —C(=O)OR, wherein R is an ester substituent, for example, a $C_{1-4}$ alkyl group, a $C_{3-7}$ heterocyclyl group, or a phenyl group, as defined above, preferably a $C_{1-4}$ alkyl group. Examples of ester groups include, but are not limited to, —C(=O)$OCH_3$, —C(=O)$OCH_2CH_3$, —C(=O)$OC(CH_3)_3$, and —C(=O)OPh.

Acyloxy (reverse ester): —OC(=O)R, wherein R is an acyloxy substituent, for example, a $C_{1-4}$ alkyl group, a $C_{3-7}$ heterocyclyl group, or a phenyl group, as defined above, preferably a $C_{1-4}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$ and —OC(=O) Ph. Further examples of acyloxy groups include, but are not limited to, methylester ($C_1$), ethylester ($C_2$), propylester ($C_3$) and butylester ($C_4$).

Naturally occurring amino acid: The term "a naturally occurring amino acid", as used herein, pertains to a monovalent moiety obtained by removing a hydrogen atom from a carboxyl group or an amino group on one of the amino acid compounds found commonly in nature (for example, alanine, arginine, asparagine, aspartate, cysteine, glycine, glutamine, glutamate, histidine, isoleucine, leucine, lysine, methionine, phenylalanine, proline, serine, threonine, tryptophan, tyrosine and valine). The amino acid is particularly selected from isoleucine, leucine and valine, most particularly valine.

In each of these groups the carbon atom which is bonded to both a carboxyl and an amino group is known as the α carbon and the carboxyl and amino groups to which it is attached are the α-carboxyl and α-amino groups. Naturally occurring amino acids are optionally substituted with a protecting group on the α-amino group or any other amino group on the moiety, protecting groups include but are not limited to acetyl, methyl and tertbutyl carbamate (boc) groups.

Phosphonate ester: —P(O)(OR)OR', wherein R and R' are independently selected from $C_{1-4}$alkyl as defined above. Examples of a phosphonate ester include, but are not limited to —P(O)(OEt)$_2$.

Cyano: —C≡N.

Pivaloyloxymethyl: A group of formula

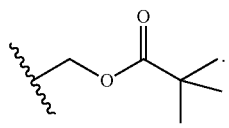 [SMILES: *COC(=O)C(C)(C)C]

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Prodrugs

The active compounds may be prepared as prodrugs. In particular, the carboxy groups comprising W$^1$ and W$^{11}$ may be present as ester, amino (—NH$_2$) and substituted amino groups. In some embodiments W$^1$ and W$^{11}$ may be independently selected from OR$^1$, NH$_2$ and NHR$^1$, where R$^1$ is selected from:

(i) $C_{3-6}$cycloalkyl;
(ii) $C_{3-7}$heterocyclyl optionally substituted with a group selected from:
   methyl; and
   ester; and
(iii) linear or branched $C_{1-4}$alkyl optionally substituted with a group selected from:
   alkoxy;
   amino;
   amido;
   acylamido;
   acyloxy;
   alkyl carboxyl ester;
   alkyl carbamoyl;
   alkyl carbamoyl ester;
   phenyl;
   phosphonate ester;
   $C_{3-7}$heterocyclyl optionally substituted with a group selected from methyl and oxo; and a naturally occurring amino acid, optionally N-substituted with a group selected from methyl, acetyl and boc;

In some embodiments, $W^1$ and $W^{11}$ are $NH_2$. In these embodiments, the compounds are of formula Ic:

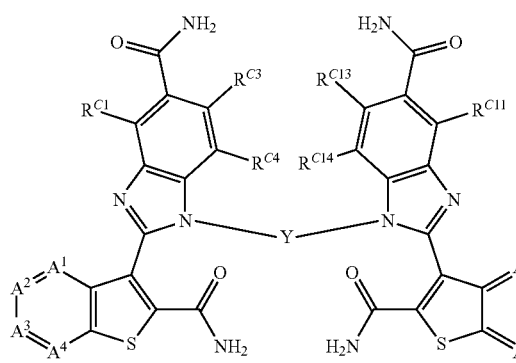

(Ic)

where $A^1$-$A^4$, $A^{11}$-$A^{14}$, $R^{C1}$, $R^{C3}$, $R^{C4}$, $R^{C11}$, $R^{C13}$, $R^{C14}$ and Y are as defined above.

In some embodiments $R^1$ is optionally substituted linear or branched $C_{1-4}$alkyl. In some embodiments $R^1$ is unsubstituted $C_{1-4}$alkyl. In some embodiments $R^1$ is substituted $C_{1-4}$alkyl.

When $R^1$ is $C_{1-4}$ alkyl, in some of these embodiments $R^1$ is methyl. In other of these embodiments, $R^1$ is ethyl. In other of these embodiments, $R^1$ is propyl (e.g. iso-propyl, n-propyl). In other of these embodiments, $R^1$ is butyl (e.g. iso-butyl, sec-butyl, tert-butyl).

In some embodiments, $R^1$ is $C_{3-6}$cycloalkyl. In some of these embodiments, $R^1$ is cyclopropyl. In other of these embodiments, $R^1$ is cyclobutyl. In other of these embodiments, $R^1$ is cyclopentyl. In other of these embodiments, $R^1$ is cyclohexyl.

In some embodiments, $R^1$ is $C_{3-7}$heterocyclyl. In some of these embodiments, the $C_{3-7}$heterocyclyl has a single nitrogen ring atom. In some of these embodiments, $R^1$ is azetidinyl, pyrrolidinyl or piperidinyl. In some of these embodiments, $R^1$ is azetidinyl. In some of these embodiments, $R^1$ is piperidinyl.

Substituents on $R^1$

In some embodiments, when $R^1$ is $C_{3-7}$heterocyclyl, it is substituted with a group selected from methyl and ester. In some embodiments, when $R^1$ is $C_{3-7}$heterocyclyl, it is substituted with methyl. In some embodiments, when $R^1$ is $C_{3-7}$heterocyclyl, it is substituted with ester.

In some embodiments, when $R^1$ is linear or branched $C_{1-4}$alkyl, it is substituted with a group selected from alkoxy, amino, amido, acylamido, acyloxy, alkyl carboxyl ester, alkyl carbamoyl, alkyl carbamoyl ester, phenyl, phosphonate ester $C_{3-7}$heterocyclyloptionally substituted with group selected from methyl and oxo, and a naturally occurring amino acid, optionally N-substituted with a group selected from methyl, acetyl and boc.

In some embodiments, when $R^1$ is linear or branched $C_{1-4}$alkyl, it is substituted with a group selected from acyloxy and phenyl. In some embodiments, when $R^1$ is linear or branched $C_{1-4}$alkyl substituted with acyloxy, it is pivaloyloxymethyl; a group of formula:

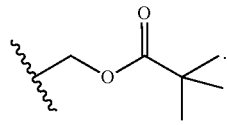 [SMILES: *COC(=O)C(C)(C)C]

In some embodiments, when $R^1$ is linear or branched $C_{1-4}$alkyl substituted with acyloxy, it is propanoyloxy-isobutyl; a group of formula:

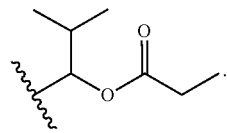 [SMILES: *C(OC(=O)CC)C(C)C]

In some embodiments, when $R^1$ is linear or branched $C_{1-4}$alkyl substituted with phenyl, it is benzyl.

In some embodiments, when $R^1$ is linear or branched $C_{1-4}$alkyl, it is substituted with a naturally occurring amino acid, optionally N-substituted with a group selected from methyl, acetyl and boc. In some embodiments when $R^1$ is linear or branched $C_{1-4}$alkyl substituted with a naturally occurring amino acid, the naturally occurring amino acid is valine. In some embodiments when $R^1$ is linear or branched $C_{1-4}$alkyl substituted with a naturally occurring amino acid, the naturally occurring amino acid is N-methyl valine. In some embodiments when $R^1$ is linear or branched $C_{1-4}$alkyl substituted with a naturally occurring amino acid, the naturally occurring amino acid is N-acetyl valine. In some embodiments when $R^1$ is linear or branched $C_{1-4}$alkyl substituted with a naturally occurring amino acid, the naturally occurring amino acid is N-boc valine.

In some embodiments, when $R^1$ is linear or branched $C_{1-4}$alkyl, it is substituted with amino. In some embodiments, when $R^1$ is linear or branched $C_{1-4}$alkyl, it is substituted with amido. In some embodiments, when $R^1$ is linear or branched $C_{1-4}$alkyl, it is substituted with acylamido. In some embodiments, when $R^1$ is linear or branched $C_{1-4}$alkyl, it is substituted with acyloxy. In some embodiments, when $R^1$ is linear or branched $C_{1-4}$alkyl, it is substituted with alkyl carboxyl ester. In some embodiments, when $R^1$ is linear or branched $C_{1-4}$alkyl, it is substituted with alkyl carbamoyl. In some embodiments, when $R^1$ is linear or branched $C_{1-4}$alkyl, it is substituted with alkyl carbamoyl ester. In some embodiments, when $R^1$ is linear or branched $C_{1-4}$alkyl, it is substituted with phenyl. In some embodiments, when $R^1$ is linear or branched $C_{1-4}$alkyl, it is substituted with phosphonate ester.

In some embodiments, when $R^1$ is linear or branched $C_{1-4}$alkyl, it is substituted with $C_{3-7}$heterocyclyl, optionally substituted with a group selected from methyl and oxo. In some embodiments when $R^1$ is linear or branched $C_{1-4}$alkyl substituted with $C_{3-7}$heterocyclyl, the $C_{3-7}$heterocyclyl is dioxole, optionally substituted with a group selected from methyl and oxo.

Isomers

Certain compounds of the invention may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; M- and P-forms; Δ- and ∧-forms; $R_a$- and $S_a$-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

"Atropisomers" refer to stereoisomers of a compound which arise due to restricted rotation about a single bond, wherein rotation about said bond is sufficiently hindered that individual conformers can be isolated and the conformers are either non-superimposable mirror images of one another (enantiomers) or stereoisomers that are not mirror images of one another (diastereomers).

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, M and P, Δ and ∧, $R_a$ and $S_a$ are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Of particular relevance to the compounds of the present invention is the atropisomerism illustrated below, where there is restricted rotation about the single bond between the two heteroaromatic ring systems in each half of the dimer:

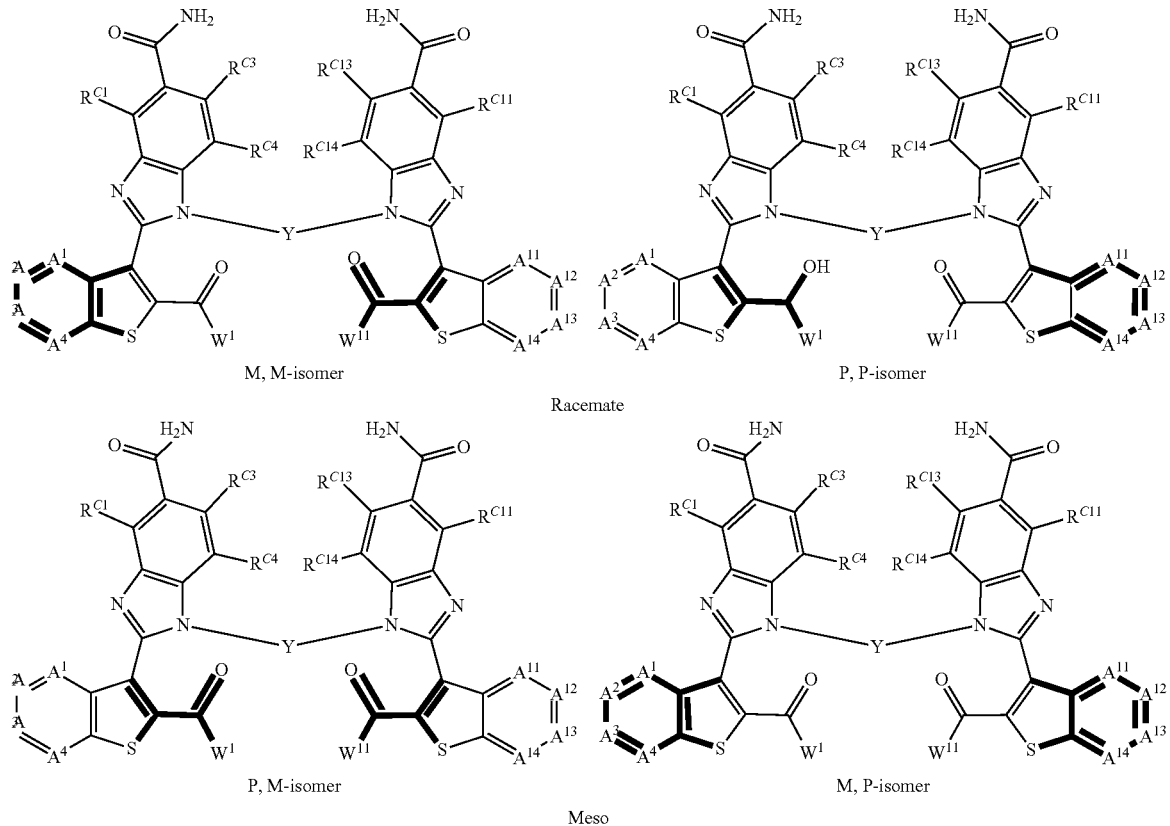

The two compounds of the racemate are non-superimposable mirror images of one another, whereas the two meso compounds which have been drawn out can be superimposed by a 180° rotation about the dotted line, where $A^1=A^{11}$, $A^2=A^{12}$, $A^3=A^{13}$, $A^4=A14$, $W^1=W^{11}$, $R^{C1}=R^{C11}$, $R^{C3}=R^{C13}$ and $R^{C4}=R^{C14}$.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

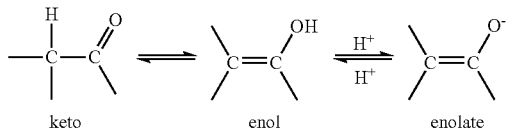

keto        enol        enolate

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as $^3$H, $^{13}$C, and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallization and chromatographic means) of such isomeric forms are either known in the art or are readily obtained by adapting the methods taught herein, or known methods, in a known manner.

Therapeutic Indications

Compounds disclosed herein may provide a therapeutic benefit in a number of disorders, in particular, in the treatment or prevention of diseases ameliorated by the modulation of STING.

One aspect of the invention provides methods of treatment or prevention of STING mediated diseases and disorders, in which agonizing STING is beneficial. Exemplary diseases/disorders includes, but are not limited to, cancer and infectious disease (such as those caused by viruses, e.g., HIV, HBV, HCV, HPV, and influenza, and bacteria). Another aspect of the invention provides the use of a STING agonist as a vaccine adjuvant.

In one embodiment, this invention provides a compound of the invention for use in therapy. This invention also provides a compound of Formula I, or a pharmaceutically acceptable salt thereof, for use in therapy. This invention particularly provides a compound of Formula I, or a pharmaceutically acceptable salt thereof, for use in the treatment of a STING-mediated disease or disorder.

This invention also provides a compound of Formula I, or a pharmaceutically acceptable salt thereof, for use as a vaccine adjuvant. There is also therefore provided an immugenic composition or vaccine adjuvant comprising a compound of Formula I, or a pharmaceutically acceptable salt thereof. In a further embodiment of the invention, there is provided a composition comprising a compound of Formula I, or a pharmaceutically acceptable salt thereof, and one or more immunostimulatory agents.

In another embodiment, this invention provides a compound of the invention for use in the treatment of a STING-mediated disease or disorder and/or for use as an immugenic composition or a vaccine adjuvant. In another embodiment, this invention provides a compound of Formula I, or a pharmaceutically acceptable salt thereof, for use in the amelioration of organ injury or damage sustained as a result of a STING-mediated disease or disorder.

The invention further provides for the use of a compound of the invention in the manufacture of a medicament for treatment of a STING-mediated disease or disorder. The invention further provides for the use of a compound of Formula I, or a salt thereof, particularly a pharmaceutically acceptable salt thereof, in the manufacture of a medicament for treatment of a STING-mediated disease or disorder, for example the diseases and disorders recited herein.

The invention further provides for the use of a compound of Formula I, or a salt thereof, particularly a pharmaceutically acceptable salt thereof, in the manufacture of a vaccine. There is further provided the use of a compound of Formula I, or a pharmaceutically acceptable salt thereof, for the manufacture of an immugenic composition comprising an antigen or antigenic composition, for the treatment or prevention of disease. There is further provided the use of a compound of Formula I, or a pharmaceutically acceptable salt thereof, for the manufacture of a vaccine composition comprising an antigen or antigenic composition, for the treatment or prevention of disease.

In another embodiment, the invention is directed to a method of treating a STING-mediated disease or disorder comprising administering a therapeutically effective amount of a compound of this invention to a human in need thereof. In another embodiment, the invention is directed to a method of treating a STING-mediated disease or disorder comprising administering a therapeutically effective amount of a compound of Formula I or a salt, particularly a pharmaceutically acceptable salt thereof, to a human in need thereof.

Infectious Diseases

The compounds of this invention may be used to treat an infectious disease, which is any disease instigated by or coincident with an infection from a pathogen. Pathogens are broadly defined as any species of organism that is foreign to a human tissue environment. Common disease causing pathogens include bacteria (many like TB), viruses (many like HBV, HIV, flu) and parasitic protozoans (like *P. falciparum* that causes malaria). The compounds of this invention may be used to treat infectious diseases derived from bacteria, such as TB infection *Mycobacterium tuberculosis*), Chlamydia, Tularemia infection *Francisella tularensis*), Plasmodium infection or infections from DNA or RNA virus. The compounds of this invention may be used to treat infectious diseases derived from the DNA virus families: Herpesviridae (herpes simplex virus-1, Kaposi's sarcoma-associated virus and Epstein-Barr virus), Papillomaviridae (human papilloma virus), Adenovirus and Hepadnaviridae (Hepatitis B virus). Examples of RNA virus families include Retroviridae (human immunodeficiency virus) Flaviviridae (Dengue virus, Hepatitis C virus), Orthomyxoviridae (influenza), and Coronaviridae (human coronavirus and SARS coronavirus).

Cancer

As used herein, the terms "cancer", "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias, such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblasts) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polycythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphomas (T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extra medullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

Examples of cancer diseases and conditions in which a compounds of this invention may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hamartoma; mesothelioma; Hodgkin's Disease or a combination of one or more of the foregoing cancers. Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In some embodiments, the compounds of the present invention may be used to treat solid or liquid tumors. In some embodiments, the compounds of the present invention may be used to treat sarcoma, breast cancer, colorectal cancer, gastroesophageal cancer, melanoma, non-small cell lung cancer (NSCLC), clear cell renal cell carcinoma (RCC), lymphomas, squamous cell carcinoma of the head and neck (SCCHN), hepatocellular carcinoma (HCC), and/or Non Hodgkin lymphoma (NHL). Suitably the present invention relates to a method for treating or lessening the severity of pre-cancerous syndromes in a mammal, including a human, wherein the pre-cancerous syndrome is selected from: cervical intraepithelial neoplasia, monoclonal gammopathy of unknown significance (MGUS), myelodysplastic syndrome, aplastic anemia, cervical lesions, skin nevi (pre-melanoma), prostatic intraepithelial (intraductal) neoplasia (PIN), Ductal Carcinoma in situ (DCIS), colon polyps and severe hepatitis or cirrhosis.

In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In one aspect the human has one or more of the following: colorectal cancer (CRC), esophageal, cervical, bladder, breast, head and neck, ovarian, melanoma, renal cell carcinoma (RCC), EC squamous cell, non-small cell lung carcinoma, mesothelioma, and prostate cancer. In another aspect the human has a liquid tumor such as diffuse large B cell lymphoma (DLBCL), multiple myeloma, chronic lymphoblastic leukemia (CLL), follicular lymphoma, acute myeloid leukemia and chronic myelogenous leukemia. In one embodiment, the compounds of the present invention may be useful for treatment of skin cancers (e.g., non-melanoma skin cancer, squamous cell carcinoma, basal cell carcinoma) or actinic keratosis. In addition to a field effect for clearing superficial skin cancers, the compounds of the present invention may prevent the development of subsequent skin cancers and pre-malignant actinic keratosis in treated patients.

Autoimmune Diseases

Autoimmune diseases associated include, but are not limited to STING associated vasculitis with onset at infancy (SAVI), Aicardi Goutieres syndrome (AGS), chilblain lupus, ataxia telanogiectasia (also referred to as Louis-Bar Syndrome), retinal vasculopathy with cerebral leukodystrophy (RCVL), systemic lupus erythematosus (SLE), cutaneous lupus, lupus nephritis, psoriasis, diabetes mellitus including insulin-dependent diabetes mellitus (IDDM), dermatomyositis, human immunodeficiency virus (HIV), AIDS, polymyositis, systemic sclerosis (scleroderma), and Sjogren's syndrome (SS), rheumatoid arthritis, psoriatic arthritis, polyarthritis, myasthenia gravis, polyarteritis nodosa, vasculitis, cutaneous vasculitis, anti-neutrophil cytoplasmic antibody (ANCA)-associated vasculitis, Henoch-Schonlein purpura, autoimmune hepatitis, primary sclerosing cholangitis, Wegener's granulomatosis, microscopi polyangiitis, Behcet's disease, spondylitis, giant cell arteritis, polymyalgia rheumatic, Raynaud's phenomenon, primary biliary cirrhosis, primary angiitis of the central nervous system microscopic polyangiitis, neuromyelitis optica and mixed connective tissue disease.

Inflammation

Inflammation represents a group of vascular, cellular and neurological responses to trauma. Inflammation can be characterized as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self-tissues.

The aim of anti-inflammatory therapy is therefore to reduce this inflammation, to inhibit autoimmunity when present, and to allow for the physiological process or healing and tissue repair to progress.

The compounds of this invention may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knee, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated with the compounds of the invention include encephalitis, Guillain-Barre syndrome, meningitis, neuromyotonia, narcolepsy, multiple sclerosis, myelitis, CNS vasculitis, and schizophrenia.

Examples of inflammation of the vasculature or lymphatic system which may be treated with the compounds of the invention include arthrosclerosis, arthritis, phlebitis, vasculitis, and lymphangitis.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The compounds of this invention may be used to treat autoimmune conditions having an inflammatory component. Such conditions include acute disseminated alopecia universalise, Behcet's disease, Chagas' disease, STING associated vasculitis with onset at infancy (SAVI), Aicardi Goutieres syndrome (AGS), chilblain lupus, ataxia telangiectasia (also referred to as Louis-Bar Syndrome), retinal vasculopathy with cerebral leukodystrophy (RCVL), ANCA)-associated vasculitis, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune hemolytic anemia, interstitial cystitis, lyme disease, morphea, psoriasis, sarcoidosis, scleroderma, ulcerative colitis, and vitiligo.

The compounds of this invention may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celiac disease).

Other inflammatory conditions which may be treated with the compounds of this invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonitis, pharyngitis, pleuritis, pneumonitis, prostatitis, pyelonephritis, and stomatitis, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory distress syndrome, Sezary syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic pulmonary disease, and inflammation accompanying infectious conditions (e.g., sepsis). In one embodiment, the compounds of this invention may be used to treat asthma.

Cellular Proliferation

The compounds of the present invention may also be useful in the treatment of one or more diseases afflicting mammals which are characterized by cellular proliferation in the area of disorders associated with neo-vascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

Neurodegenerative Diseases

The compounds of this invention may be used to treat neurodegenerative diseases. Exemplary neurodegenerative diseases includes, but are not limited to, multiple sclerosis, Huntington's disease, Alzheimer's disease, Parkinson's disease, amyotrophic lateral sclerosis (ALS).

Combinations

The compounds of this invention may be employed alone or in combination with other therapeutic agents. As modulators of the immune response, the compounds of this invention may also be used in monotherapy or used in combination with another therapeutic agent in the treatment of diseases and conditions in which modulation of STING is beneficial. Combination therapies according to the present invention thus comprise the administration of a compound of Formula I or a pharmaceutically acceptable salt thereof, and at least one other therapeutically active agent. In one embodiment, combination therapies according to the present invention comprise the administration of at least one compound of Formula I or a pharmaceutically acceptable salt thereof, and at least one other therapeutic agent. The compound(s) of Formula I and pharmaceutically acceptable salts thereof, and the other therapeutic agent(s) may be administered together in a single pharmaceutical composition or separately and, when administered separately this may occur simultaneously or sequentially in any order. The amounts of the compound(s) of Formula I and pharmaceutically acceptable salts thereof, and the other therapeutic agent(s) and the relative timings of administration will be selected in order to achieve the desired combined therapeutic effect. Thus in a further aspect, there is provided a combination comprising a compound of Formula I, or a pharmaceutically acceptable salt thereof, together with one or more other therapeutic agents.

The compounds of Formula I and pharmaceutically acceptable salts thereof may be used in combination with one or more other therapeutic agents which may be useful in the prevention or treatment of allergic disease, inflammatory disease, or autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents).

The compounds of Formula I and pharmaceutically acceptable salts thereof may be used in combination with radiotherapy and/or surgery and/or at least one other therapeutic agent which may be useful in the treatment of cancer and pre-cancerous syndromes. Any anti-neoplastic agent that has activity versus a susceptible tumor being treated may be utilized in the combination. Typical anti-neoplastic agents useful include, but are not limited to, (a) anti-microtubule agents such as diterpenoids (e.g. paclitaxel, docetaxel) and vinca alkaloids (e.g. vinblastine, vincristine, and vinorelbine); (b) platinum coordination complexes (e.g. oxaliplatin, cisplatin and carboplatin); (c) alkylating agents such as nitrogen mustards (e.g. cyclophosphamide, melphalan, and chlorambucil), oxazaphosphorines, alkylsulfonates (e.g. busulfan), nitrosoureas (e.g. carmustine), and triazenes (e.g. dacarbazine); (d) antibiotic agents such as anthracyclins (e.g. daunorubicin and doxorubicin), actinomycins (e.g. dactinomycin) and bleomycins; (e) topoisomerase II inhibitors such as epipodophyllotoxins (e.g. etoposide and teniposide); (f) antimetabolites such as purine and pyrimidine analogues and anti-folate compounds (e.g. fluorouracil, methotrexate, cytarabine, mercaptopurine, thioguanine, and gemcitabine); (g) topoisomerase I inhibitors such as camptothecins (e.g. irinotecan, topotecan, and various optical forms of 7-(4-methylpiperazino-methylene)-10,II-ethylenedioxy-20-camptothecin); (h) hormones and hormonal analogues (e.g. adrenocorticosteroids such as prednisone and prednisolone which are useful in the treatment of malignant lymphoma and acute leukemia in children; aminoglutethimide and other aromatase inhibitors such as anastrozole, letrozole, vorozole, and exemestane useful in the treatment of adrenocortical carcinoma and hormone dependent breast carcinoma containing estrogen receptors; progestins such as megestrol acetate useful in the treatment of hormone dependent breast cancer and endometrial carcinoma; estrogens, and anti-estrogens such as fulvestrant, flutamide, nilutamide, bicalutamide, cyproterone acetate and 5-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207, 716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and leuprolide); (i) signal transduction pathway inhibitors; (j) non-receptor tyrosine angiogenesis inhibitors; (k) immunotherapeutic agents (e.g. ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell energy, approaches using transfected immune cells such as cytokine-transfected dendritic cells, approaches using cytokine-transfected tumor cell lines and approaches using anti-idiotypic antibodies); (l) proapoptotic agents (e.g. bcl-2 antisense oligonucleotides); (m) cell cycle signaling inhibitors; (n) immuno-oncology agents and (o) immunostimulatory agents.

Signal Transduction Pathway Inhibitors

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath 2000; Shawver 1997; and Lofts 1994.

Tyrosine kinases, which are not growth factor receptor kinases, are termed nonreceptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh 1999; and Bolen 1997.

SH2/SH3 domain blockers are agents that disrupt SH2 or SH3 domain binding in a variety of enzymes or adaptor proteins including, PI3-K p85 subunit, Src family kinases, adaptor molecules (She, Crk, Nek, Grb2) and Ras-GAP. SH2/SH3 domains as targets for anticancer drugs are discussed in Smithgall 1995.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto 1999; Brodt 2000; Massagué 1996; Philip 1995; Lackey 2000; U.S. Pat. No. 6,268,391; and Martínez-Lacaci 2000.

Inhibitors of Phosphotidyl inositol-3 Kinase family members including blockers of Pekinese, ATM, DNA-PK, and Ku are also useful in the present invention. Such kinases are discussed in Abraham 1996; Canman 1998; Jackson 1997; and Zhong 2000.

Also useful in the present invention are Myo-inositol signaling inhibitors such as phospholipase C blockers and Myoinositol analogues. Such signal inhibitors are described in Powis 1994.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky 2000; Ashby 1998; and Oliff 1999.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green 2000); Herceptin® erbB2 antibody (see Stern 2000); and 2CB VEGFR2 specific antibody (see Brekken 2000).

Non-Receptor Tyrosine Angiogenesis Inhibitors

Anti-angiogenic therapeutic agents including non-receptor MEK angiogenesis inhibitors may also be useful. Anti-angiogenic agents such as those which inhibit the effects of vascular endothelial growth factor, (for example the anti-vascular endothelial cell growth factor antibody bevacizumab [Avastin™], and compounds that work by other mechanisms (for example linomide, inhibitors of integrin αvβ3 function, endostatin and angiostatin).

Cell Cycle Signaling Inhibitors

Cell cycle signaling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signaling are under development. For instance, examples of cyclin dependent kinases, including CDK2, CDK4, and CDK6 and inhibitors for the same are described in, for instance, Rosania 2000.

Immuno-Modulators

Additional examples of other therapeutic agents (e.g., anti-neoplastic agent) for use in combination or co-administered with a compound of Formula I are immuno-modulators. As used herein "immuno-modulators" refer to any substance including monoclonal antibodies that affects the immune system. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdivo/nivolumab and Keytruda/pembrolizumab). Other immuno-modulators include, but are not limited to, ICOS antibodies, OX-40 antibodies, PD-L1 antibodies, LAG3 antibodies, TIM-3 antibodies, 41BB antibodies and GITR antibodies.

Anti-PD-L1 Agents

Additional examples of other therapeutic agents (anti-neoplastic agent) for use in combination or co-administered with a compound of this invention are anti-PD-L1 agents. Anti-PD-L1 antibodies and methods of making the same are known in the art. Such antibodies to PD-L1 may be polyclonal or monoclonal, and/or recombinant, and/or humanized. Exemplary PD-L1 antibodies are disclosed in U.S. Pat. Nos. 8,217,149, 8,383,796, 8,552,154, 9,212,224, and 8,779,108, and US Patent Appln. Pub. Nos. 2011/0280877, 2014/0341902 and 2013/0045201. Additional exemplary antibodies to PD-L1 (also referred to as CD274 or B7-H1) and methods for use are disclosed in U.S. Pat. Nos. 7,943,743, 8,168,179, and 7,595,048; WO2014/055897, WO2016/007235; and US Patent Appln. Pub. Nos. 2013/0034559 and 2015/0274835. PD-L1 antibodies are in development as immunomodulatory agents for the treatment of cancer.

In one embodiment, the antibody to PD-L1 is an antibody disclosed in U.S. Pat. No. 8,217,149. In another embodiment, the anti-PD-L1 antibody comprises the CDRs of an antibody disclosed in U.S. Pat. No. 8,217,149. In another embodiment, the antibody to PD-L1 is an antibody disclosed in U.S. Pat. No. 8,779,108. In another embodiment, the anti-PD-L1 antibody comprises the CDRs of an antibody disclosed in US Application No. 8779108. In another embodiment, the antibody to PD-L1 is an antibody disclosed in US Patent Appln. Pub. No. 2013/0045201. In another embodiment, the anti-PD-L1 antibody comprises the CDRs of an antibody disclosed in US Patent Appln. Pub. No. 2013/0045201. In one embodiment, the anti-PD-L1 antibody is BMS-936559 (MDX-1105), which was described in WO 2007/005874. In another embodiment, the anti-PD-L1 antibody is MPDL3280A (RG7446). In another embodiment, the anti-PD-L1 antibody is MEDI4736, which is an anti-PD-L1 monoclonal antibody described in WO 2011/066389 and US 2013/034559. In another embodiment, the anti-PD-L1 antibody is TECENTRIQ™ (atezolizumab), which is an anti-PD-L1 cancer immunotherapy which was approved in the US in May 2016 for specific types of bladder cancer. In another embodiment, anti-PD-L1 antibody is YW243.55.S70 which is an anti-PD-L1 described in WO 2010/077634 and U.S. Pat. No. 8,217,149. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559.

PD-1 Antagonist

Additional examples of other therapeutic agents (anti-neoplastic agent) for use in combination or co-administered with a compound of this invention are PD-1 antagonists. "PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCDI, PDI, CD279 and SLEB2 for PD-1; PDCDILI, PDLI, B7H1, B7-4, CD274 and B7-H for PD-LI; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgGI, IgG2, IgG3 and IgG4 constant regions, and in preferred embodiments, the human constant region is an IgGI or IgG4 constant region. In some embodiments, the antigen binding fragment is selected from the group consisting of Fab, Fab'-SH, F(ab')2, scFv and Fv fragments.

Examples of mAbs that bind to human PD-1, and useful in the various aspects and embodiments of the present invention, are described in U.S. Pat. Nos. 7,488,802, 7,521,051, 8,008,449, 8,354,509, 8,168,757, WO2004/004771, WO2004/072286, WO2004/056875, and US2011/0271358. Specific anti-human PD-1 mAbs useful as the PD-1 antagonist in any of the aspects and embodiments of the present invention include: MK-3475, a humanized IgG4 mAb with the structure described in WHO Drug Information, Vol. 27, No. 2, pages 161-162 (2013) and which comprises the heavy and light chain amino acid sequences shown in FIG. 6; nivolumab, a human IgG4 mAb with the structure described in WHO Drug Information, Vol. 27, No. 1, pages 68-69 (2013) and which comprises the heavy and light chain amino acid sequences shown in FIG. 7; the humanized antibodies h409AII, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Other examples of mAbs that bind to human PD-L1, and useful in the treatment method, medicaments and uses of the present invention, are described in WO2013/019906, WO2010/077634 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdivo/nivolumab is a fully human monoclonal antibody marketed by Bristol Myers Squibb directed against the negative immunoregulatory human cell surface receptor PD-1 (programmed death-1 or programmed cell death-I/POD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of PI3K/Akt pathway activation. Other names for nivolumab include: BMS-936558, MDX-1106, and ONO-4538. The amino acid sequence for nivolumab and methods of using and making are disclosed in U.S. Pat. No. 8,008,449.

Antibodies to ICOS

Additional examples of other therapeutic agents (antineoplastic agent) for use in combination or co-administered with a compound of Formula I are antibodies to ICOS. ICOS is a co-stimulatory T cell receptor with structural and functional relation to the CD28/CTLA-4-Ig superfamily (Hutloff 1999). Activation of ICOS occurs through binding by ICOS-L (B7RP-1/B7-H2). Neither B7-1 nor B7-2 (ligands for CD28 and CTLA4) bind or activate ICOS. However, ICOS-L has been shown to bind weakly to both CD28 and CTLA-4 (Yao 2011). Expression of ICOS appears to be restricted to T cells. ICOS expression levels vary between different T cell subsets and on T cell activation status. ICOS expression has been shown on resting TH17, T follicular helper (TFH) and regulatory T (Treg) cells; however, unlike CD28; it is not highly expressed on naive THI and TH2 effector T cell populations (Paulos 2010). ICOS expression is highly induced on CD4+ and CD8+ effector T cells following activation through TCR engagement (Wakamatsu 2013).

CDRs for murine antibodies to human ICOS having agonist activity are shown in PCT/EP2012/055735 (WO 2012/131004). Antibodies to ICOS are also disclosed in WO 2008/137915, WO 2010/056804, EP1374902, EP1374901, and EP1125585. Agonist antibodies to ICOS or ICOS binding proteins are disclosed in WO2012/131004, WO 2014/033327, WO2016/120789, US20160215059, and US20160304610. In one embodiment, agonist antibodies to ICOS include ICOS binding proteins or antigen binding portions thereof comprising one or more of: CDRHI as set forth in SEQ ID NO:1; CDRH2 as set forth in SEQ ID NO:2; CDRH3 as set forth in SEQ ID NO:3; CDRLI as set forth in SEQ ID NO:4; CDRL2 as set forth in SEQ ID NO:5 and/or CDRL3 as set forth in SEQ ID NO:6 or a direct equivalent of each CDR wherein a direct equivalent has no more than two amino acid substitutions in said CDR as disclosed in WO2016/120789, which is incorporated by reference in its entirety herein. In one embodiment, the ICOS binding protein or antigen binding portion thereof is an agonist antibody to ICOS comprising a VH domain comprising an amino acid sequence at least 90% identical to the amino acid sequence set forth in SEQ ID NO:7 and/or a VL domain comprising an amino acid sequence at least 90% identical to the amino acid sequence as set forth in SEQ ID NO:8 as set forth in WO2016/120789 wherein said ICOS binding protein specifically binds to human ICOS. In one embodiment, the ICOS binding protein is an agonist antibody to ICOS comprising a VH domain comprising the amino acid sequence set forth in SEQ ID NO:7 and a VL domain comprising the amino acid sequence set forth in SEQ ID NO:8 as set forth in WO2016/120789.

Yervoy (ipilimumab) is a fully human CTLA-4 antibody marketed by Bristol Myers Squibb. The protein structure of ipilimumab and methods are using are described in U.S. Pat. Nos. 6,984,720 and 7,605,238.

CD134, also known as OX40, is a member of the TNFR-superfamily of receptors which is not constitutively expressed on resting naive T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in U.S. Pat. Nos. 7,504,101; 7,758,852; 7,858,765; 7,550,140; 7,960,515; WO2012/027328; WO2013/028231. In one embodiment, the OX40 antigen binding protein is one disclosed in WO2012/027328 (PCT/US2011/048752), international filing date 23 Aug. 2011. In another embodiment, the antigen binding protein comprises the CDRs of an antibody disclosed in WO2012/027328 (PCT/US2011/048752), international filing date 23 Aug. 2011, or CDRs with 90% identity to the disclosed CDR sequences. In a further embodiment the antigen binding protein comprises a VH, a VL, or both of an antibody disclosed in WO2012/027328 (PCT/US2011/048752), international filing date 23 Aug. 2011, or a VH or a VL with 90% identity to the disclosed VH or VL sequences.

In another embodiment, the OX40 antigen binding protein is disclosed in WO2013/028231 (PCT/US2012/024570), international filing date 9 Feb. 2012, which is incorporated by reference in its entirety herein. In another embodiment, the antigen binding protein comprises the CDRs of an antibody disclosed in WO2013/028231 (PCT/US2012/024570), international filing date 9 Feb. 2012, or CDRs with 90% identity to the disclosed CDR sequences. In a further embodiment, the antigen binding protein comprises a VH, a VL, or both of an antibody disclosed in WO2013/028231 (PCT/US2012/024570), international filing date 9 Feb. 2012, or a VH or a VL with 90% identity to the disclosed VH or VL sequences. In one embodiment, the OX40 antigen binding protein is an isolated agonist antibody to OX40 comprising a light chain variable region having a sequence at least 90% identical to the amino acid sequence of SEQ ID NO: 10 as set forth in WO2013/028231 and a heavy chain variable region having a sequence at least 90% identical to the amino acid sequence of SEQ ID NO:4 as set forth in WO2013/028231. In one embodiment, the OX40 antigen binding protein is an isolated antibody comprising a light chain variable comprising the amino acid sequence of SEQ ID NO:10 as set forth in WO2013/028231 and a heavy chain variable region comprising the amino acid sequence of SEQ ID NO:4 as set forth in WO2013/028231.

Immunostimulatory Agent

Additional examples of other therapeutic agents for use in combination or coadministered with a compound of Formula I, or a salt thereof are immunostimulatory agents.

As used herein "immunostimulatory agent" refers to any agent that can stimulate the immune system. As used herein immunostimulatory agents include, but are not limited to, vaccine adjuvants, such as Toll-like receptor agonists, T-cell checkpoint blockers, such as mAbs to PD-1 and CTL4 and T-cell checkpoint agonist, such as agonist mAbs to OX-40 and ICOS. As used herein "immunostimulatory agent" refers to any agent that can stimulate the immune system. As used herein immunostimulatory agents include, but are not limited to, vaccine adjuvants.

The term "Toll-like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll-like receptors (TLRs) are a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity. In humans, ten TLRs have been identified. TLRs that are expressed on the surface of cells include TLR-1, -2, -4, -5, and -6, while TLR-3, -7/8, and -9 are expressed with the ER compartment. Human DC subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following: Pam3Cys, a TLRI/2 agonist; CFA, a TLR2 agonist; MALP2, a TLR2 agonist; Pam2Cys, a TLR2 agonist; FSL-I, a TLR-2 agonist; Hib-OMPC, a TLR-2 agonist; polyinosinic:polycytidylic acid (Poly I:C), a TLR3 agonist; polyadenosine-polyuridylic acid (poly AU), a TLR3 agonist; Polyinosinic-Polycytidylic acid stabilized with poly-L-lysine and carboxymethylcellulose (Hiltonol), a TLR3 agonist; bacterial flagellin a TLR5 agonist; imiquimod, a TLR7 agonist; resiquimod, a TLR7/8 agonist; loxoribine, a TLR7/8 agonist; and unmethylated CpG dinucleotide (CpG-ODN), a TLR9 agonist.

Additional TLR agonists known in the art and finding use in the present invention further include, but are not limited to aminoalkyl glucosaminide phosphates (AGPs) which bind to the TLR4 receptor are known to be useful as vaccine adjuvants and immunostimulatory agents for stimulating cytokine production, activating macrophages, promoting innate immune response, and augmenting antibody production in immunized animals. An example of a naturally occurring TLR4 agonist is bacterial LPS. An example of a semisynthetic TLR4 agonist is monophosphoryl lipid A (MPL). AGPs and their immunomodulating effects via TLR4 are disclosed in patent publications such as WO 2006/016997, WO 2001/090129, and/or U.S. Pat. No. 6,113,918 and have been reported in the literature. Additional AGP derivatives are disclosed in U.S. Pat. Nos. 7,129,219, 6,525,028 and 6,911,434. Certain AGPs act as agonists of TLR4, while others are recognized as TLR4 antagonist In addition to the immunostimulatory agents described above, the compositions of the present invention may further comprise other therapeutic agents which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated Listeriamonocytogenes), compositions which mediate innate immune activation via, (NOD)-like receptors (NLRs), Retinoic acid inducible gene-based (RIG)-I-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive bacteria. Lipopolysaccharides are expressed by most bacteria, with MPL being one example. Flagellin refers to the structural component of bacterial flagella that is secreted by pathogenic and commensal bacteria, rt-Galactosylceramide (rt.-GalCer) is an activator of natural killer T (NKT) cells. Muramyl dipeptide is a bioactive peptidoglycan motif common to all bacteria.

Because of their adjuvant qualities, TLR agonists are preferably used in combinations with other vaccines, adjuvants and/or immune modulators, and may be combined in various combinations. Thus, in certain embodiments, the herein described compounds of Formula I that bind to STING and induce STING-dependent TBKI activation and an inactivated tumor cell which expresses and secretes one or more cytokines which stimulate DC induction, recruitment and/or maturation, as described herein can be administered together with one or more TLR agonists for therapeutic purposes.

Indoleamine 2,3-dioxygenase 1 (IDO1) is a key immunosuppressive enzyme that modulates the anti-tumor immune response by promoting regulatory T cell generation and blocking effector T cell activation, thereby facilitating tumor growth by allowing cancer cells to avoid immune surveillance (Lemos 2016; Munn 2016). Further active ingredients (antineoplastic agents) for use in combination or co-administered with the presently invented compounds of Formula I are IDO inhibitors. Epacadostat, ((Z)—N-(3-bromo-4-fluorophenyl)-N'-hydroxy-4-[2-(sulfamoylamino) ethylaminol]-I,2,5-oxadiazole-3-carboxamidine) is a highly potent and selective oral inhibitor of the IDO1 enzyme that reverses tumor-associated immune suppression and restores effective anti-tumor immune responses. Epacadostat is disclosed in U.S. Pat. No. 8,034,953.

Additional examples of other therapeutic agents (antineoplastic agent) for use in combination or co-administered with a compound of Formula I are CD73 inhibitors and A2a and A2b adenosine antagonists.

The compounds of Formula I and pharmaceutically acceptable salts thereof may be used in combination with at least one other therapeutic agent useful in the prevention or treatment of bacterial and viral infections. Examples of such agents include, without limitation: polymerase inhibitors such as those disclosed in WO 2004/037818, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofovir, lamivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, tenofovir disproxil fumarate, tenofovir alafenamide fumarate/hemifumarate, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capraviine, TMC-278, TMC-125, etravirine, rilpivirine and similar agents; entry inhibitors such as enfuvirtide (T-20), T-1249, PRO-542, PRO-140, TNX-355, BMS-806, 5-Helix and similar agents; integrase inhibitors such as dolutegravir, elvitegravir, raltegravir L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; pharmacokinetic enhancers such as cobicistat; neuraminidase inhibitors such as CS-8958, zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents.

The compounds of Formula I and pharmaceutically acceptable salts thereof may also be used in combination with other therapeutic agents which may be useful in the treatment of Kaposi's sarcoma-associated herpesvirus infections (KSHV and KSHV-related) include, without limitation chemotherapeutic agents such as bleomycin, vinblastine, vincristine, cyclophosphamide, prednisone, alitretinoin and liposomal anthracyclines such as doxorubicin, daunorubicin, immunotherapeutics such as Rituximab, Tocilizumab, Siltuximab and others such as Paclitaxel and Rapamycin.

In one embodiment of this invention, the at least one other therapeutic agent is an antimycobacterial agent or a bactericidal antibiotic. The compounds of Formula I and pharmaceutically acceptable salts thereof may also be used in combination with at least one other therapeutic agent which may be useful in the treatment of TB infection *Mycobacterium tuberculosis*) and Tularemia (*Franciseiia tularensis*) include without limitation to first line oral agents isoniazid, Rifampicin, pyrazinamide, ethambutol, streptomycin, rifabutin; injectable agents including kanamycin, amikacin, capreomycin, streptomycin; fluoroquinolones including levofloxacin moxifloxacin ofloxacin; oral bacteriostatic agents para-aminosalicylic acid cycloserine terizidone thionamide protionamide; SQ-109 PNU-100480, Rifapentine Linezolid, PA-824 AZD5847, Gatifloxacin Moxifloxacin, Sirturo (bedaquiline) Delamanid (OPC-67683) and agents with undetermined mechanism of action in the treatment of drug-resistant TB, including clofazimine, linezolid, amoxicillin/clavulanate thioacetazone imipenem/cilastatin high dose isoniazid clarithromycin, ciprofloxacin. The compounds of Formula I and pharmaceutically acceptable salts thereof may also be used in combination with an antimycobacterial agent (such as isoniazid (INH), ehambutol (Myambutol®), rifampin (Rifadin®), and pyrazinamide (PZA)) a bactericidal antibiotic (such as rifabutin (Mycobutin®) or rifapentine (Priftin®)), an aminoglycoside (Capreomycin®), a fluorquinolone (levofloxacin, moxifloxicin, ofloxacin), thioamide (ehionamide), cyclosporine (Sandimmune®), para-aminosalicyclic acid (Paser®), cycloserine (Seromycin®), kanamycin (Kantrex®), streptomycin, viomycin, capreomycin (Capastat®)), bedaquiline fumarate (Sirturo®), oxazolidinone (Sutezolid®), PNU-100480, or delamanid (OPC-67683).

The compounds of Formula I and pharmaceutically acceptable salts thereof may also be used in combination with at least one other therapeutic agent which may be useful in the treatment of Chlamydia include, without limitations Azithromycin, Doxycycline, Erythromycin, Levofloxacin, Ofloxacin.

The compounds of this invention may also be used in combination with at least one other therapeutic agent which may be useful in the treatment of Plasmodium infection include, without limitations to chloroquine, atovaquone-proguanil, artemether-lumefantrine, mefloquine, quinine, quinidine, doxocycline, cindamycin, artesunate, primaquine.

In the treatment of amyotrophic lateral sclerosis (ALS), a compound of Formula I or a pharmaceutically acceptable salts thereof may be used in combination with a glutamate blocker (Riluzole (Rilutek®)), quinidine (Nuedexta®), anticholinergics (Amitriptyline®, Artane®, scopolamine patch (Transderm Scop®)), sympathomimetics (pseudoephedrine), mucolytics (guaifenesin), or analgesics (tramadol (Ultram®); ketorolac (Toradol®); morphine; fentanyl patch (Duragesic®)).

In the treatment of multiple scelrosis, a compound of Formula I or pharmaceutically acceptable salts thereof may be used in combination with corticosteroids (prednisone, methylprednisolone), Interferon Beta 1-A (Avonex®, Extavia®, Rebif®, Betaseron®), peginterferon beta-IA (Plegridy®), Glatiramer acetate (Copaxone®); glatiramer acetate (Glatopa®-generic equivalent of Copaxone); Dimethyl fumarate (Tecfidera®); Fingolimod (Gilenya®)); teriflunomide (Aubagio®); dalfampridine (Ampyra®); daclizumab (Zinbryta); alemtuzumab (Lemtrada®); natalizumab (Tysabri®); or mitoxantrone hydrochloride (Novantrone®).

The compounds of this invention may also be used as adjuvants to improve the immune response raised to any given antigen and/or reduce reactogenicity/toxicity in a patient, particularly a human, in need thereof. As such, a compound of this invention may be used in combination with vaccine compositions to modify, especially to enhance, the immune response for example by increasing the level or duration of protection and/or allowing a reduction in the antigenic dose.

The compounds of Formula I and pharmaceutically acceptable salts thereof may be used in combination with one or more vaccines or immunogenic antigens useful in the prevention or treatment of viral infections. Such vaccines or immunogenic antigens include, without limitation to pathogen derived proteins or particles such as attenuated viruses, virus particles, and viral proteins typically used as immunogenic substances. Examples of viruses and viral antigens include, without limitations to Polioviruses, Coronaviridae and Coronaviruses, Rhinovirus (all subtypes), Adenoviruses (all subtypes), Hepatitis A, Hepatitis B, Hepatitis C, Hepatitis D, Human papillomavirus (including all subtypes), Rabies viruses, Human T-cell lympotropic virus (all subtypes), Rubella virus, Mumps virus, Coxsackie virus A (all subtypes), Cosackie virus B (all subtypes), human enteroviruses, herpesviruses including cytomegalovirus, Epstein-Barr virus, human herpes viruses (all subtypes), herpes simplex virus, varicella zoster virus, human immunodeficiency virus (HIV) (all subtypes), Epstein-Barr virus, Reoviruses (all subtypes), Filoviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkypox virus, vaccinia virus, cowpox virus), yatapoxviruses (tanapox virus, Yaba monkey tumor virus), parapoxvirus, molluscipoxvirus, Yellow fever, Hantaviruses including Hantaan, Seoul, Dobrava, Sin Nombre, Puumala, and Dobrava-like Saaremaa, human para influenza viruses and influenza viruses (all types), HINI influenza and swine influenza viruses, respiratory syncytial virus (all subgroups), rotaviruses including human rotaviruses A-E, bovine rotavirus, rhesus monkey rotavirus, Polyomaviruses including simian virus 40, JC virus, BK virus, Coltiviruses, eyach virus, calciviruses, and Parvoviridae including dependovirus, parvovirus and erythrovirus.

Accordingly, this invention provides an immugenic composition comprising an antigen or antigenic composition and a compound of Formula I, or a pharmaceutically acceptable salt thereof. There is further provided a vaccine composition comprising an antigen or antigenic composition and a compound of Formula I, or a pharmaceutically acceptable salt thereof. The compounds of Formula I and pharmaceutically acceptable salts thereof may also be used in combination with at least one other therapeutic agent which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, anti-fibrotic agents, antiinflammatory agents such as corticosteroids or NSAIDs (non-steroidal anti-inflammatory agents) and similar agents.

A compound that modulates STING, particularly a compound of Formula I or a pharmaceutically acceptable salt thereof, may be administered in combination with other antiinflammatory agents, including oral or topical corticosteroids, anti-TNF agents, 5-aminosalicyclic acid and mesalamine preparations, hydroxycloroquine, thiopurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologies, anti-ILI agents, anti-IL17 biologies, anti-CD22, anti-integrin agents, anti-IFNa, anti-CD20 or CD4 biologies and other cytokine inhibitors or biologies to T-cell or B-cell receptors or interleukins.

For example, in the treatment of systemic lupus erythematosus and related lupus disorders, a compound that modulates STING, particularly a compound of Formula I, or a pharmaceutically acceptable salt thereof, may be administered in combination with at least one other therapeutic agent, including, a corticosteroid (such as prednisolone (Delatsone®, Orapred, Millipred, Omnipred, Econopred, Flo-Pred), an immunosuppressive agent (such as methotrexate (Rhuematrex®, Trexall®), dexamethasone (Decadron®, Solurex®), Mycophenolate mofetil (Cellcept®), Tacrolimus®, Sirolimus®), B-cell therapy (belimumab (Benlysta®), B-cell inhibitor (Atacicept®, Apratuzumab® (anti-CD22), SBI-087 (anti-CD20), an anti-BAFF antibody (LY2127399, A623), Velcade®), azathioprine (Azasan®, Imuran®), triamcinolone (Clinacort®, Kenalog-10®), hydroxychloroquine (Plaquenil®), thalidomide (Immunoprin®, Contergan®), immunoglobulin therapy (HyQiva®, Flebogamma®, Gamunex®, Privigen®, Gammagard®), anti-interferon-alpha therapy (Rontalizumab®, Sifalimumab®, AGS-009®, IFN Kinoid), TLR7 and TLR9 blockers (IMO-3100), anti-cytokine therapies (anti-IL6 (CNTO-136), anti-interferon-gamma (AMG811), immunomodulatory therapy (Lupuzor™, Abatacept, Orencia®, AMG557, Laquinimod, Paquinimod, Leflunomide, anti-ICOS (Medi-570), anti-CD40 ligand antibody (CDP7657)), and/or a platelet aggregation inhibitor (aspirin).

In treatment of vasculitis and disease with inflammation of small or medium size blood vessels, a compound that modulates STING, particularly a compound of Formula I, or a pharmaceutically acceptable salt thereof, may be administered in combination with alkylating agents (cyclophosphamide, Cytoxan®), anti-rheumatic anti-CD20 antibody (Rituxan®, Rituximab®), and anti-TNF inhibitors (Etanrcept®).

In the treatment of psoriasis, a compound that modulates STING, particularly a compound of Formula I, or a pharmaceutically acceptable salt thereof, may be administered in combination with ixekizumab, tildrakizumab (MK-3222), or secukinumab (AIN457).

In one embodiment of this invention, the at least one other therapeutic agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarinic antagonist. For example, in the treatment of asthma, a compound that inhibits STING, particularly a compound of Formula I or a pharmaceutically acceptable salt thereof, may be administered in combination with an inhaled corticosteroid ((ICS) such as fluticasone proprionate (Flovent®), beclomethasone dipropionate (QVAR®), budesonide (Pulmicort), trimcinolone acetonide (Azmacort®), flunisolide (Aerobid®), mometasone fuorate (Asmanex® Twisthaler®), or Ciclesonide (Alvesco®)), a long acting beta agonist ((LABA) such as formoterol fumarate (Foradil®), salmeterol xinafoate (Serevent®)), a combination of an ICS and LABA (such as fluticasone furoate and vilanterol (Breo Ellipta®), formoterol/budesonide inhalation (Symbicort®), beclomethasone dipropionate/formoterol (Inuvair®), and fluticasone propionate/salmeterol (Advair®), a short acting beta agonist ((SABA) such as albuterol sulfate (ProAir®, Proventil HFA®, Ventolin HFA®, AccuNeb® Inhalation Solution), levalbuterol tartrate (Xopenex® HFA), ipratropium bromide/albuterol (Combivent® Respimat®), ipratropium bromide (Atrovent® HFA), a leukotriene modifier (such as montelukast sodium (Singulair®), zafirlukast (Accolate®), or zileuton (Zyflo®), and anti-IgE (such as omalizumab (Xolair®)), a methylxanthine bronchodilator (such as theophylline (Accurbron®, Aerolate®, Aquaphyllin®, Asbron®, Bronkodyl®, Duraphyl®, Elixicon®, Elixomin®, Elixophyllin®, Labid®, Lanophyllin®, Quibron-T®, Slo-Bid®, Slo-Phyllin®, Somophyllin®, Sustaire®, Synophylate®, T-Phyll®, Theo-24®, Theo-Dur®, Theobid®, Theochron®, Theoclear®, Theolair®, Theolixir®, Theophyl®, Theovent®, Uni-dur®, Uniphyl®), a mast cell inhibitor (such as cromulyn sodium (Nasalcrom®) and nedocromil sodium (Tilade®)), a long-acting muscarinic antagonist ((LAMA) such as mometasone furoate/formoterol fumarate dihydrate (Dulera®)).

Other agents that may be suitable for use in combination therapy in the treatment of asthma include a protein tyrosine kinase inhibitor (masitinib), CRTH2/D-prostanoid receptor antagonist (AMG 853), indacaterol (Arcapta®Neohaler®), an epinephrine inhalation aerosol (E004), fluticasone furoate/fluticasone proprionate, vinanterol inhalation/fluticasone furoate powder (Relovair™), fluticasone propionate/eformoterol fumarate dehydrate (Flutiform®), reslizumab, salbutamol dry-powder inhalation, tiotropium bromide (Spiriva®HandiHaler®), formoterol/budesonide (Symbicort®SMART®), fluticasone furoate (Veramyst®), Vectura's VR506, lebrikizumab (RG3637), a combination phosphodiesterase (PDE)-3 and (PDE)-4 inhibitor (RPL554).

In one embodiment of this invention, the at least one other therapeutic agent is selected from a long acting beta agonist, a long-acting inhaled anticholinergic or muscarinic antagonist, a phosphodiesterase inhibitor, a combination of an inhaled corticosteroid long acting beta agonist, a short acting beta agonist, and an inhaled corticosteroid. For example, in the treatment of COPD, a compound that modulates STING, particularly a compound of Formula I or a pharmaceutically acceptable salt thereof, may be administered in combination with a LABA (such as salmeterol xinafoate (Serevent), umeclidinium/vilanterol (Anoro Ellipta®), umeclidinium (Incruse Ellipta®), aformoterol tartrate (Brovana®), formoterol fumarate inhalation powder (Foradil®), indacterol maleate (Arcapta® Neohaler®), or fluticasone propionate/eformoterol fumarate dehydrate (Flutiform®)), a long-acting inhaled anticholinergic (or muscarinic antagonist, such as tiotropium bromide (Spiriva®), and aclidinium bromide (Tudorza® Pressair®), a phosphodiesterase (PDE-r) inhibitor (such as roflumilast, Daliresp®), a combination ICS/LABA (such as fluticasone furoate and vilanterol (Breo Ellipta®), fluticasone propionate/salmeterol (Advair®), budesonide/formoterol (Symbicort®), mometasone/formoterol (Dulera®), ipratropium bromide/albuterol sulfate (Duoneb®, Atrovent®), albuterol/ipratropium (Combivent Respimat®)), a SABA (such as ipratropium bromide (Atrovent®), and albuterol sulfate (ProAir®, Proventil®)), and an ICS (such as budesonide (Pulmicort®) and fluticasone propionate (Flovent®), beclometasone dipropionate (QVAR®).

Other agents that may be suitable for use in combination therapy in the treatment of COPD include SCH527123 (a CXCR2 antagonist), glycoprronium bromide ((NVA237) Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Striverdi® Respimat®), tiotropium (Spiriva®)/olodaterol (Striverdi® Respimat®), and aclidinium/formoterol inhalation.

In one embodiment of this invention, the at least one other therapeutic agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. For example, in the treatment of systemic scleroderma, a compound that modulates STING, particularly a compound of Formula I or a pharmaceutically acceptable salt thereof, may be administered in combination with an oral corticosteroid (such as prednisolone (Delatsone®, Orapred, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®), FK506 (tacrolimus), thalidomide (Thalomid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestril®, Prinivil®), diltaizem (Cardizem®, Cardizem SR®, Cardizem CD®, Cardia®, Dilacor®, Tiazac®)), a serotonin reuptake inhibitor (such as fluoxetine (Prozac®)), an endothelin-1 receptor inhibitor (such as bosentan (Tracleer®) or epoprostenol (Flolan®, Veletri®, Prostacyclin®)) an anti-fibrotic agent (such as colchicines (Colcrys®), para-aminobenzoic acid (PABA), dimethyl sulfoxide (DMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (arGentis Pharmaceutical), belimumab (Benlysta®), tocilizumab (Actema®).

In the treatment of Sjogren's syndrome, a compound that modulates STING, particularly a compound of Formula I or a pharmaceutically acceptable salt thereof, may be administered in combination with anti-rheumatic agents (hydroxychloroquine and Plaquenil®, Ridaura®, Kineret®), cholinergic agonists (Salagen®, Evoxac®), a JAK inhibitor (Xelijanz®, and anti-TNF treatments (Remicade®, Humira®, Enbrel®, Cimzia®, Simponi®).

In one embodiment of this invention, the at least one other therapeutic agent is a ciliary neurotrophic growth factor or a gene transfer agent. For example, in the treatment of retinitis pigmentosa, a compound that modulates STING, particularly a compound of Formula I or a pharmaceutically acceptable salt thereof, may be administered in combination with a ciliary neurotrophic growth factor (NT-501-CNTF) or gene transfer agent, UshStat®.

In one embodiment of this invention, the at least one other therapeutic agent is selected from a trivalent (IIV3) inactivated influenza vaccine, a quadrivalent (IIV4) inactivated influenza vaccine, a trivalent recombinant influenza vaccine, a quadrivalent live attenuated influenza vaccine, an antiviral agent, or inactivated influenza vaccine. For example, in the treatment of influenza, a compound that modulates STING, particularly a compound of Formula I or a pharmaceutically acceptable salt thereof, may be administered in combination with a trivalent (IIV3) inactivated influenza vaccine (such as Afluria®, Fluarix®, Flucelvax®, FluLaval®, Fluvirin®, Fluzone®), a quadrivalent (IIV4) inactivated influenza vaccine (such as Fluarix® Quadrivalent, Flulaval® Quadrivalent, Fluzone® Quadrivalent), a trivalent recombinant influenza vaccine (such as FluBlok®), a quadrivalent live attenuated influenza vaccine (such as FluMist® Quadrivalent), an antiviral agent (such as oseltamivir (Tamiflu®), zanamivir (Relenza®), rimantadine (Flumadine®), or amantadine (Symmetrel®)), or Fluad®, Fludase, FluNhance®, Preflucel, or VaxiGrip®.

In the treatment of a staphylococcus infection, a compound that modulates STING, particularly a compound of Formula I or a pharmaceutically acceptable salt thereof, may be administered in combination with an antibiotic (such as a β-Lactam cephalosporin (Duricef®, Kefzol®, Ancef®, Biocef®, etc), nafcillin (Unipen®), a sulfonamide (sulfamethoxazole and trimethoprim (Bacrim®, Septra®) sulfasalazine (Azulfidine®), acetyl sulfisoxazole (Gantrisin®), etc), or vancomycin (Vancocin®)).

In one embodiment of this invention, the at least one other therapeutic agent is selected from a topical immunomodulator or calcineurin inhibitor, a topical corticosteroid, an oral corticosteroid, an interferon gamma, an antihistamine, or an antibiotic. For example, in the treatment of atopic dermatitis, a compound that modulates STING, particularly a compound of Formula I, or a pharmaceutically acceptable salt thereof, may be administered in combination with a topical immunomodulator or calcineurin inhibitor (such as pimecrolimus (Elidel®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methyl prednisolone (Medrol®), or prednisolone (Pediapred®, Prelone®), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives flucloxacillin (Floxapen®) or dicloxacillin (Dynapen®), erythromycin (Eryc®, T-Stat®, Erythra-Derm®, etc.)), a non-steroidal immunosuppressive agent (such as azathioprine (Imuran®, Azasan®), methotrexate (Rhuematrex®, Trexall®), cyclosporin (Sandimmune®), or mycophenolate mofetil (CellCept®)).

The compounds of the invention may also be formulated with vaccines as adjuvants to modulate their activity. Such compositions may contain antibody(ies) or antibody fragment(s) or an antigenic component including but not limited to protein, DNA, live or dead bacteria and/or viruses or virus-like particles, together with one or more components with adjuvant activity including but not limited to aluminum salts, oil and water emulsions, heat shock proteins, lipid A preparations and derivatives, glycolipids, other TLR agonists such as CpG DNA or similar agents, cytokines such as GM-CSF or IL-12 or similar agents.

In a further aspect of the invention, there is provided a vaccine adjuvant comprising a compound of Formula I, or a pharmaceutically acceptable salt thereof. There is further provided a vaccine composition comprising a compound of Formula I, or a pharmaceutically acceptable salt thereof, and an antigen or antigen composition.

Methods of Treatment

The compounds of the present invention may be used in a method of therapy. Also provided is a method of treatment, comprising administering to a subject in need of treatment a therapeutically-effective amount of a compound of the invention. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, intravitreal and intrasternal; by implant of a depot, for example, subcutaneously, intravitreal or intramuscularly. The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orang-utan, gibbon), or a human.

In one embodiment where treating tumours, intratumoural injection may used.

Formulations

While it is possible for the active compound to be administered alone, it is preferable to present it as a pharmaceutical composition (e.g. formulation) comprising at least one active compound, as defined above, together with one or more pharmaceutically acceptable carriers, adjuvants, excipients, diluents, fillers, buffers, stabilizers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, *Remington's Pharmaceutical Sciences,* 18th edition, Mack Publishing Company, Easton, Pa., 1990.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g. by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or moulding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g. sodium lauryl sulfate); and preservatives (e.g. methyl p-hydroxybenzoate, propyl p-hydroxybenzoate, sorbic acid). Moulded tablets may be made by moulding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavoured basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurized pack, with the use of a suitable propellant, such as dichlorodifluoromethane, trichlorofluoromethane, dichlorotetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required.

Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or exosomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/mL to about 10 μg/mL, for example from about 10 ng/ml to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or exosomes or other microparticulate systems which are designed to target the active compound to blood components or one or more organs.

Dosage

It will be appreciated by one of skill in the art that appropriate dosages of the compound, and compositions comprising the compound, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 μg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, the active compound is administered to a human patient according to the following dosage regime: about 100 mg, 3 times daily.

In one embodiment, the active compound is administered to a human patient according to the following dosage regime: about 150 mg, 2 times daily.

In one embodiment, the active compound is administered to a human patient according to the following dosage regime: about 200 mg, 2 times daily.

However in one embodiment, the active compound is administered to a human patient according to the following dosage regime: about 50 or about 75 mg, 3 or 4 times daily.

In one embodiment, the active compound is administered to a human patient according to the following dosage regime: about 100 or about 125 mg, 2 times daily.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

The Subject/Patient

The subject/patient may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject/patient may be any of its forms of development, for example, a foetus. In one preferred embodiment, the subject/patient is a human.

General Synthesis Methods

The compounds of the invention can be prepared employing the following general methods and using procedures described in detail in the examples. The reaction conditions referred to are illustrative and non-limiting, for example one skilled in the art may use a diverse range of synthetic methods to synthesize the desired compounds such as but not limited to methods described in literature (for example but not limited to March's Advanced Organic Chemistry: Reactions, Mechanisms, and Structure, 7th Edition or Larock's Comprehensive Organic Transformations: Comprehensive Organic Transformations: A Guide to Functional Group Preparations).

Compounds of formula I as described above, can be prepared by synthetic strategies outlined below, wherein the definitions above apply.

General Synthesis 1
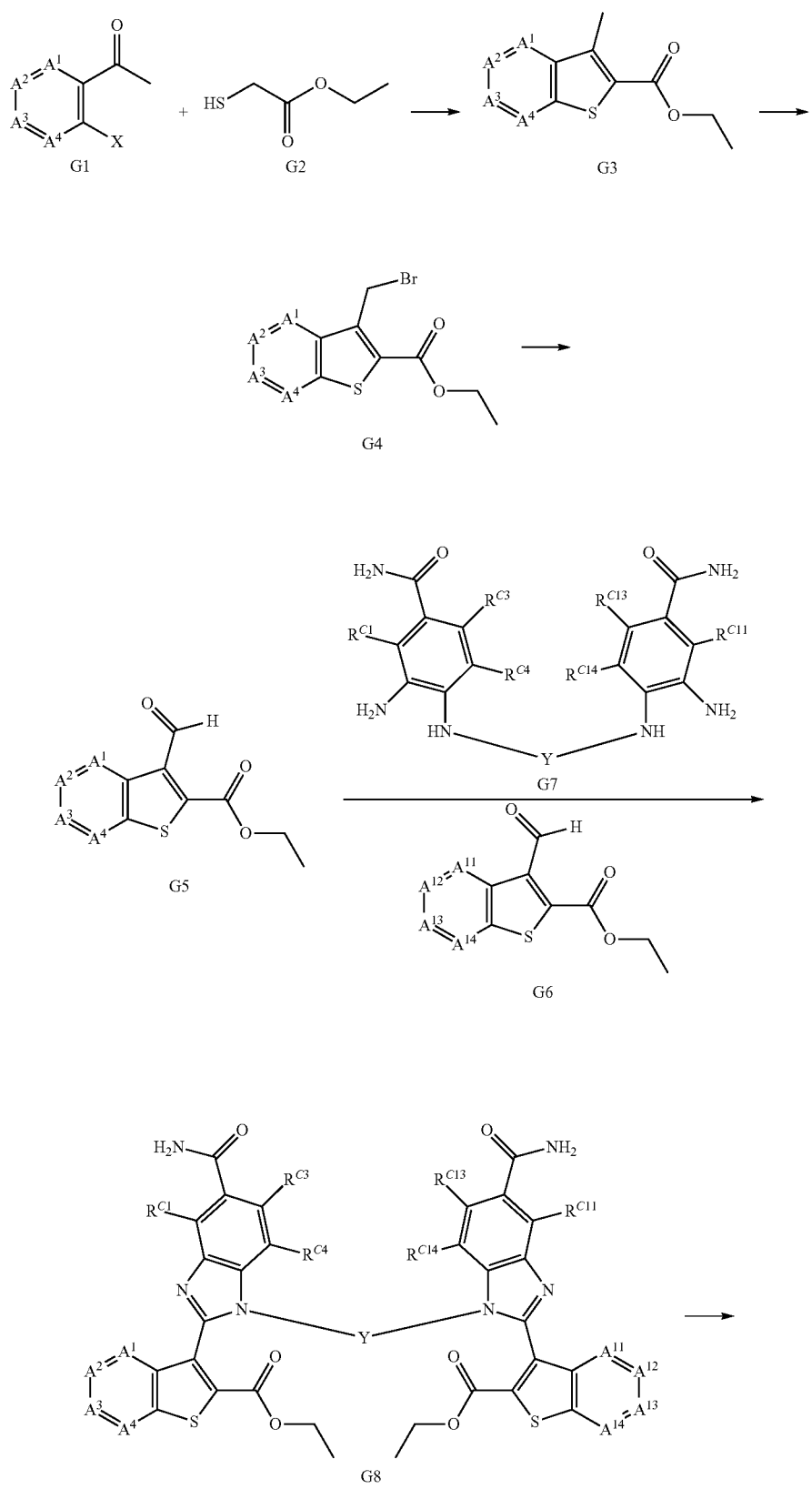

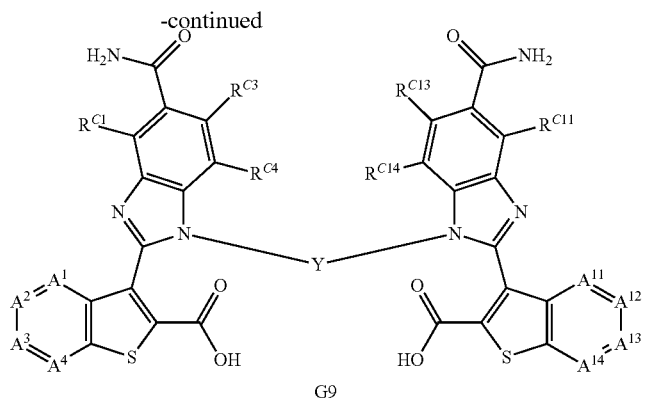

G9

Scheme 1 illustrates the synthesis of compounds with the structure G9. The first step involves reaction of a suitably substituted ketone G1 with ethyl 2-mercaptoacetate G2 in the presence of a suitable base such as, but not limited to, $K_2CO_3$. Bromination of product G3 to form alkyl bromide G4 may be performed using a suitable bromine source such as, but not limited to, N-bromosuccinimide, in the presence of an initiator such as, but not limited to, benzoyl peroxide. An oxidation reaction of G4 may be carried out with a suitable oxidant such as, but no limited to, N-methylmorpholine N-oxide to give compounds of the type G5. One equivalent of aldehyde G5 with substituents $A^1$, $A^2$, $A^3$ and $A^4$ and one equivalent of aldehyde G6 with substituents $A^{11}$, $A^{12}$, $A^{13}$ and $A^{14}$ are reacted with one equivalent of tetra-aniline G7 in the presence of either (a) a suitable acid such as, but not limited to, acetic acid or (b) sodium bisulfite or (c) sodium metabisulfite to give compounds of the type G8. In some instances two equivalents of the same aldehyde (i.e. G6=G5, $A^1=A^{11}$, $A^2=A^{12}$, $A^3=A^{13}$, $A^4=A^{14}$) are reacted with one equivalent of tetra-aniline G7 to give compounds of the type G8. In other instances, the tetra-aniline will be symmetrical ($R^{C1}=R^{C11}$, $R^{C3}=R^{C13}$, $R^{C4}=R^{C14}$) Dicarboxylic acid G9 can be formed by hydrolysis of diester G8 with a base such as an alkali metal hydroxide or an acid such as aqueous hydrochloric acid.

It will be appreciated by those skilled in the art that substituents $R^A$ (when $A^1=CR^A$), $R^B$ (when $A^2=CR^B$), $R^C$ (when $A^3=CR^C$), and $R^D$ (when $A^4=CR^D$), $R^{AA}$ (when $A^{11}=CR^{AA}$), $R^{BB}$ (when $A^{12}=CR^{BB}$), $R^{CC}$ (when $A^{13}=CR^{CC}$) and $R^{DD}$ (when $A^{14}=CR^{DD}$), $R^{C1}$, $R^{C3}$ and $R^{C4}$, $R^{C11}$, $R^{C13}$ and $R^{C14}$ on compound G8 or G9 may be a halogen atom to allow for transition-metal catalyzed transformations such as Ulmann, Negishi, Stille, Suzuki-Miyaura, Sonogashira and Buchwald-Hartwig couplings, or for SnAr displacements to produce further examples of the type of compound I.

General Synthesis 2

Scheme 2

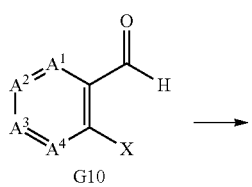

G10

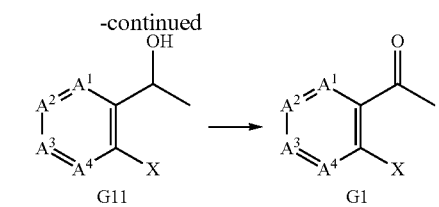

G11　　G1

Compounds of the structure G1 can be obtained by reaction of a suitably substituted aldehyde G10 with a Grignard reagent such as methyl magnesium bromide to give alcohol G11. Methods for oxidation of alcohol G11 to give ketone G1 will be apparent to those skilled in the art, but include for example the use of reagents such as chromium trioxide and sulphuric acid.

General Synthesis 3

Scheme 3

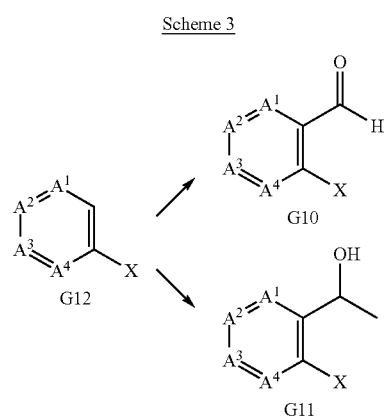

Compounds of the structure G10 can be made by treatment of a suitably substituted arene or heteroarene G12 with either an alkyl lithium such as, but not limited to, n-butyllithium, or a lithium amide base such as, but not limited, to lithium diisopropylamide, and subsequent quenching of the resultant lithiated species with N,N-dimethylformamide. Alternatively, the lithiated species formed from treatment of G12 with alkyl lithium or lithium amide may be quenched with acetaldehyde to give compound G11 directly.

General Synthesis 4

Scheme 4

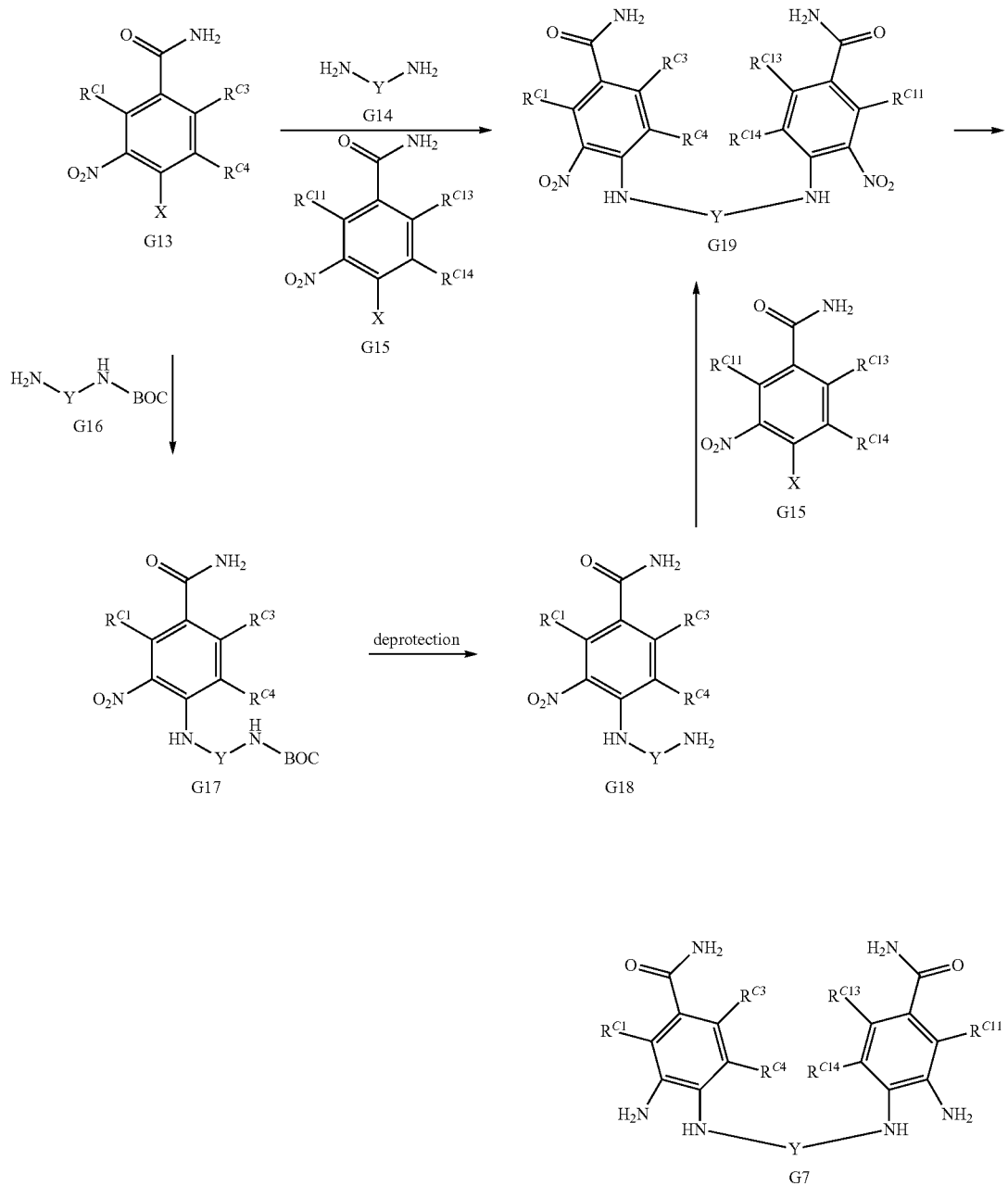

Compounds of the formula G7 can be obtained by reaction of a suitably substituted halo-nitrophenyl compound G13 with a di-amine of the type G14 and an equivalent of another halo-nitrophenyl compound of the type G15 to give the bis-nitro species G19. In some instances, the bis-nitro compound G19 will be symmetrical where $R^{C1}=R^{C11}$, $R^{C3}=R^{C13}$, $R^{C4}=R^{C14}$. Alternatively, compounds of the type G19 can be accessed by first reacting a suitably substituted halo-nitrophenyl compound G13 with a diamine G16 mono-protected with a suitable protecting group such as, but not limited to, a Boc group to give intermediate G17. Deprotection of the amine using, for example, acidic conditions gives intermediates of the type G18 which can be subsequently reacted with a suitably substituted halo-nitrophenyl group G15 to give the di-nitro intermediate G19. A final reduction step, such as hydrogenation using 10% Pd/C in a hydrogen atmosphere, provides access to the tetra-aniline intermediate G7.

General Synthesis 5

Scheme 5a

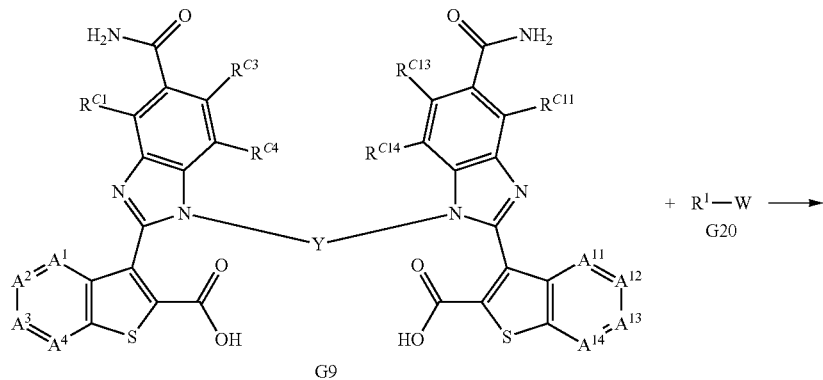

Conditions for conversion of diacid G9 to diester or diamide G21 will be apparent to those skilled in the art, but include an excess of a suitable nucleophile G20 and a catalyst such as concentrated sulphuric acid (for formation of an ester), as shown in Scheme 5a. Alternatively G9 may be first activated by a coupling agent such as, but not limited to, 1-[bis(dimethylamino)methylene]-1H-1,2,3-triazolo[4,5-b]pyridinium 3-oxide hexafluorophosphate, 1-ethyl-3-(3-dimethylaminopropyl)carbodiimide or N,N'-dicyclohexylcarbodiimide before reaction with nucleophile G20 in the presence of a catalyst such as, but not limited to, 4-dimethylaminopyridine (for formation of a diester or diamide) or in the presence of a base such as, but not limited to, N,N-diisopropylethylamine (for formation of a diamide).

Diester G23 can be accessed by reaction of diacid G9 with a suitable alkyl halide G22 in the presence of a suitable base such as, but not limited to, cesium carbonate as shown in Scheme 5b.

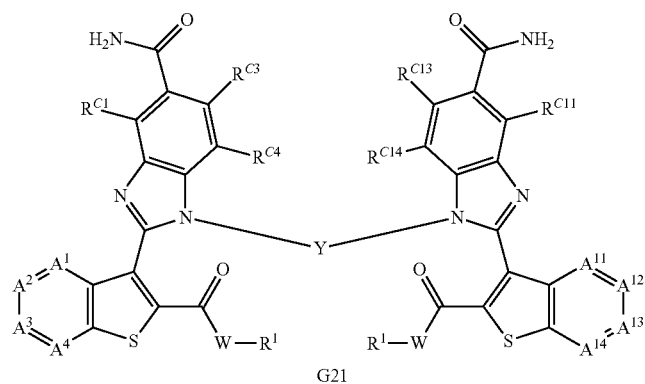

Scheme 5b

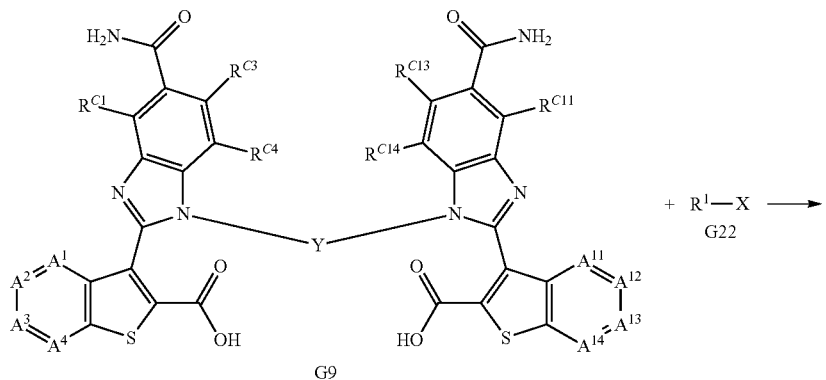

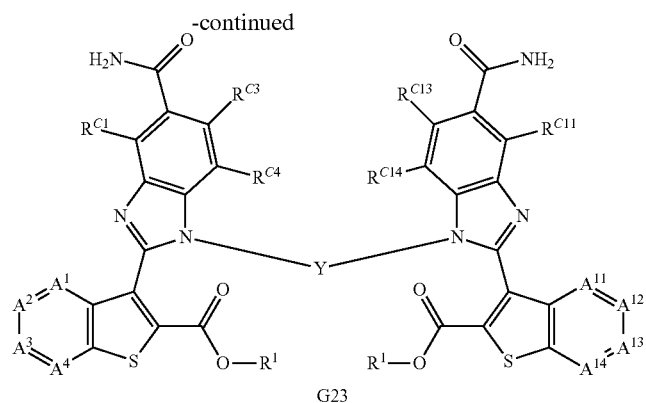
G23
General Synthesis 6
Scheme 6
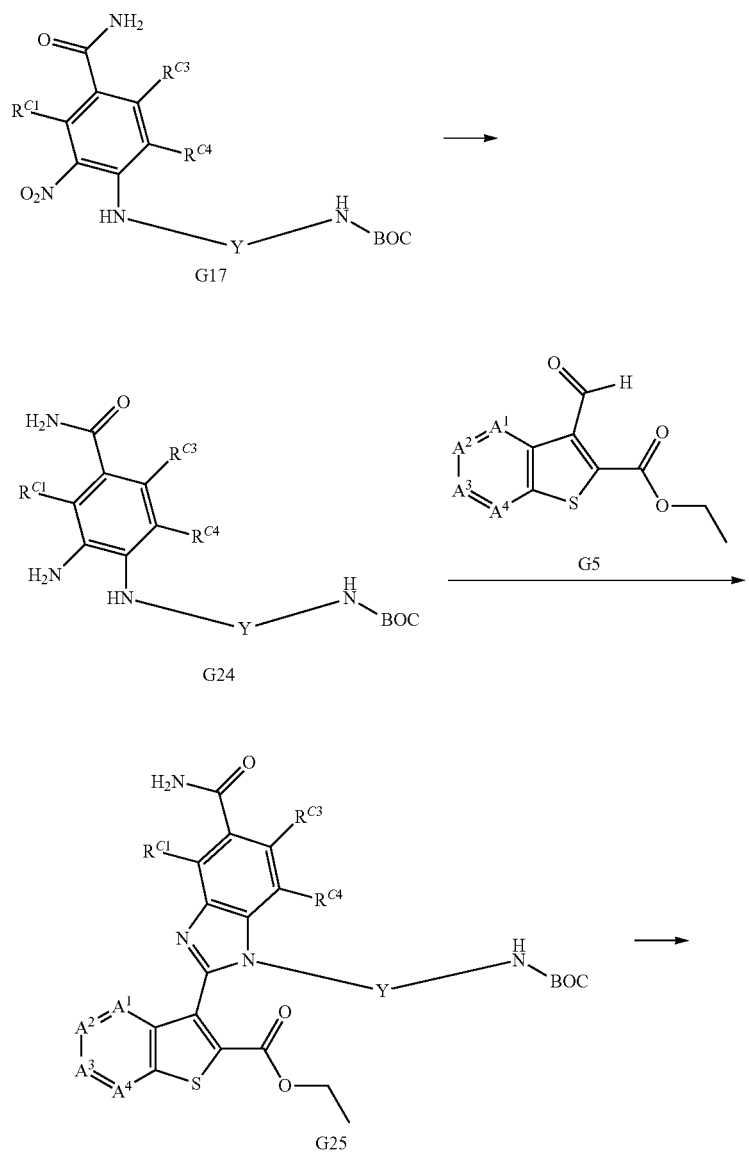

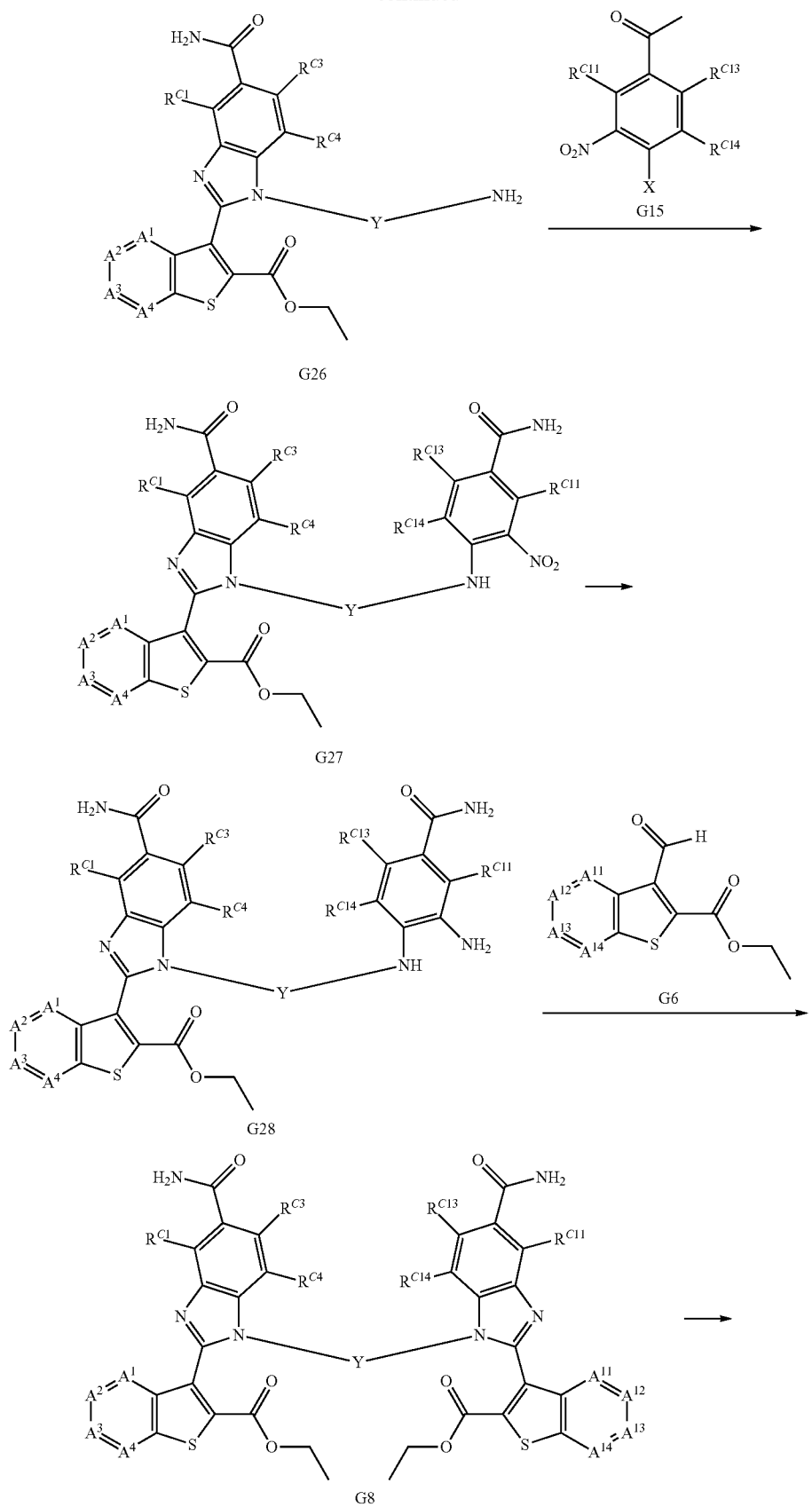

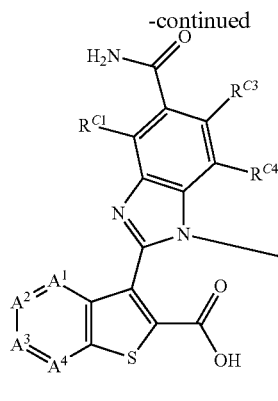
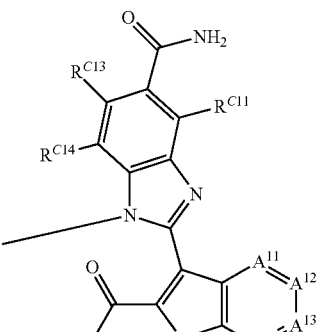

G9

Scheme 6 illustrates an alternative route into the synthesis of compounds with the structure G9. Nitro intermediate G17 can be reduced to the di-aniline intermediate using conditions such as, but not limited to, stirring over a heterogenous catalyst such as Pd/C under an atmosphere of hydrogen to give G24. Condensation of this di-aniline with aldehyde intermediate G5 in the presence of either (a) a suitable acid such as, but not limited to, acetic acid or (b) sodium bisulfite or (c) sodium metabisulfite provides access to intermediates of the type G25. Treatment of the mono-Boc protected material under acidic conditions liberates the primary amine to give compounds of the type G26. A second nucleophilic aromatic substitution can be performed with a halo-nitrophenyl compound of the type G15 in the presence of a base such as but not limited to trimethylamine to give G27. A reduction step of the nitro compound G27 can be performed to give G28 using conditions such as, but not limited to, stirring over a heterogenous catalyst such as Pd/C under an atmosphere of hydrogen. The di-aniline intermediate G28 can be condensed with an equivalent of an aldehyde of the type G6 in the presence of either (a) a suitable acid such as, but not limited to, acetic acid or (b) sodium bisulfite or (c) sodium metabisulfite to give bis-benzimidazole G8. The bis-benzimidazole structure G8 can then be hydrolyzed in a final step with a base such as an alkali metal hydroxide or an acid such as aqueous hydrochloric acid to give the free diacid G9.

It will be appreciated by those skilled in the art that substituents $R^A$ (when $A^1=CR^A$), $R^B$ (when $A^2=CR^B$), $R^C$ (when $A^3=CR^C$), and $R^D$ (when $A^4=CR^D$), $R^{AA}$ (when $A^{11}=CR^{AA}$), $R^{BB}$ (when $A^{12}=CR^{BB}$), $R^{CC}$ (when $A^{13}=CR^{CC}$) and $R^{DD}$ (when $A^{14}=CR^{DD}$), $R^{C1}$, $R^{C3}$ and $R^{C4}$, $R^{C11}$, $R^{C13}$ and $R^{C14}$ on compound G8 or G9 may be a halogen atom to allow for transition-metal catalyzed transformations such as Ulmann, Negishi, Stille, Suzuki-Miyaura, Sonogashira and Buchwald-Hartwig couplings, or for SnAr displacements to produce further examples of the type of compound I.

FURTHER EMBODIMENTS

In some embodiments, the two moieties attached to Y are the same, i.e. $A^{11}=A^1$, $A^{12}=A^2$, $A^{13}=A^3$, $A^{14}=A^4$, $R^{C11}=R^{C1}$, $R^{C13}=C^3$, $R^{C14}=R^{C4}$, $W^{11}=W^1$.

$A^1$-$A^4$ and $A^{11}$-$A^{14}$

In some embodiments, $A^1$ is $CR^A$.
In other embodiments, $A^1$ is N.
In some embodiments, $A^2$ is $CR^B$.
In other embodiments, $A^2$ is N.
In some embodiments, $A^3$ is $CR^C$.
In other embodiments, $A^3$ is N.
In some embodiments, $A^4$ is $CR^D$.
In other embodiments, $A^4$ is N.
In some embodiments, two of $A^1$, $A^2$, $A^3$ and $A^4$ are N.
In other embodiments, one of $A^1$, $A^2$, $A^3$ and $A^4$ are N.
In other embodiments, none of $A^1$, $A^2$, $A^3$ and $A^4$ are N, i.e. $A^1$, $A^2$, $A^3$ and $A^4$ are $CR^A$, $CR^B$, $CR^C$, and $CR^D$ respectively.
In some embodiments, $A^{11}$ is $CR^{AA}$.
In other embodiments, $A^{11}$ is N.
In some embodiments, $A^{12}$ is $CR^{BB}$.
In other embodiments, $A^{12}$ is N.
In some embodiments, $A^{13}$ is $CR^{CC}$.
In other embodiments, $A^{13}$ is N.
In some embodiments, $A^{14}$ is $CR^{DD}$.
In other embodiments, $A^{14}$ is N.
In some embodiments, two of $A^{11}$, $A^{12}$, $A^{13}$ and $A^{14}$ are N.
In other embodiments, one of $A^{11}$, $A^{12}$, $A^{13}$ and $A^{14}$ are N.
In other embodiments, none of $A^{11}$, $A^{12}$, $A^{13}$ and $A^{14}$ are N, i.e. $A^{11}$, $A^{12}$, $A^{13}$ and $A^{14}$ are $CR^{AA}$, $CR^{BB}$, $CR^{CC}$, and $CR^{DD}$ respectively.

In some embodiments, the compound of formula I is selected from compounds of formulae (IIIa)-(IIIe):

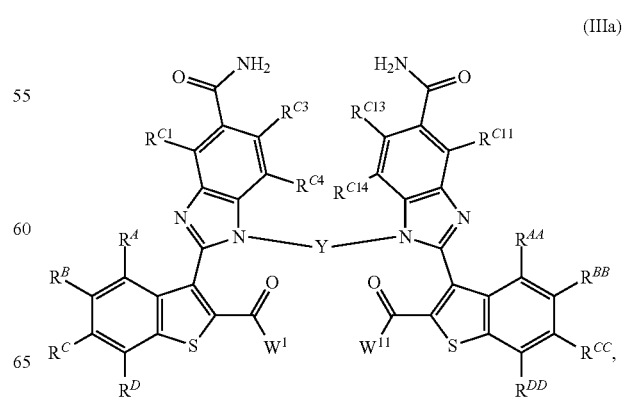

(IIIa)

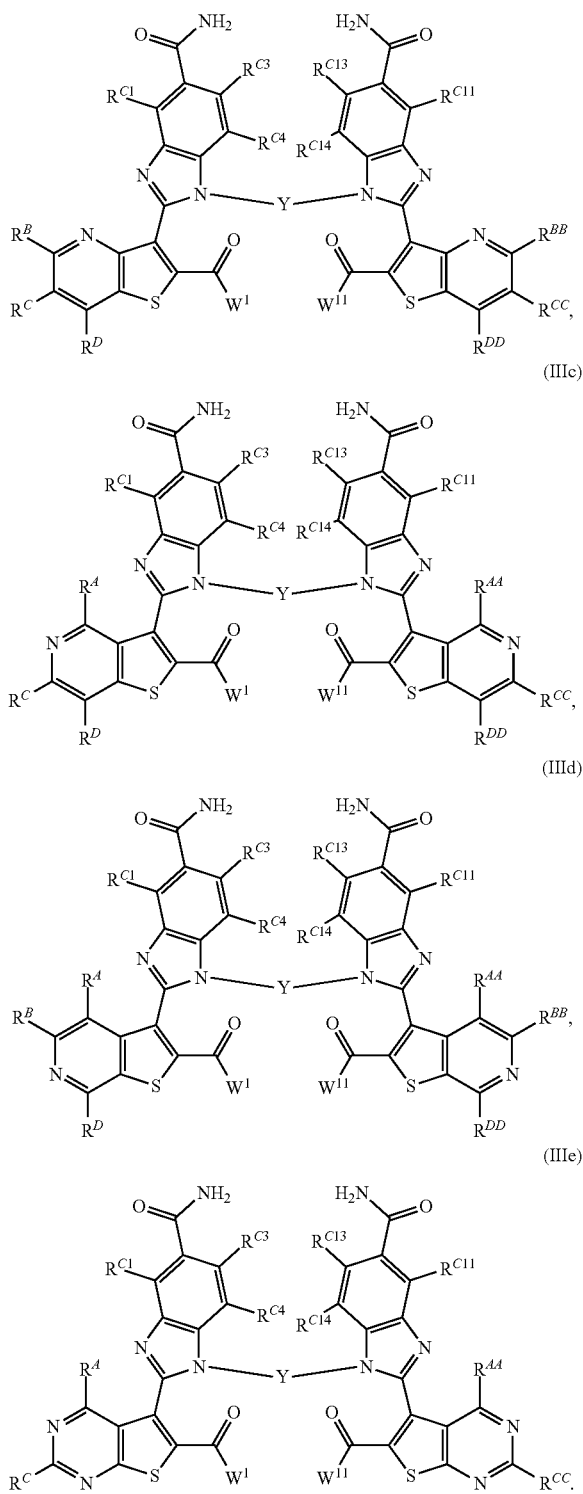

$R^A$, $R^B$, $R^C$, $R^D$, $R^{AA}$, $R^{BB}$, $R^{CC}$ and $R^{DD}$ (if Present)

In some embodiments, $R^A$, $R^B$, $R^C$, $R^D$, $R^{AA}$, $R^{BB}$, $R^{CC}$ and $R^{DD}$, (if present) are selected from H, F, Cl, Br, Me, $CF_3$, cyclopropyl, cyano, OMe, OEt, $CH_2OH$, $CH_2OMe$ and OH.

In some embodiments one of $R^A$, $R^B$, $R^C$ and $R^D$, (if present), and one of $R^{AA}$, $R^{BB}$, $R^{CC}$ and $R^{DD}$, (if present) is selected from H, F, Cl, Br, Me, $CF_3$, cyclopropyl, cyano, OMe, OEt, $CH_2OH$, $CH_2OMe$ and OH. The remainder (if present) are H.

In other embodiments two of $R^A$, $R^B$, $R^C$ and $R^D$, (if present), and two of $R^A$, $R^B$, $R^C$, $R^D$, $R^{AA}$, $R^{BB}$, $R^{CC}$ and $R^{DD}$, (if present) are selected from H, F, Cl, Br, Me, $CF_3$, cyclopropyl, cyano, OMe, OEt, $CH_2OH$, $CH_2OMe$ and OH. The remainder (if present) are H.

In some embodiments, one or two of $R^A$, $R^B$, $R^C$ and $R^D$, (if present), and one or two of $R^{AA}$, $R^{BB}$, $R^{CC}$ and $R^{DD}$, (if present) are selected from H, F, Cl, Br, Me, $CF_3$, cyclopropyl, cyano and OMe. The remainder (if present) are H. In some of these embodiments, one or two of $R^A$, $R^B$, $R^C$ and $R^D$ (if present), and one or two of $R^{AA}$, $R^{BB}$, $R^{CC}$ and $R^{DD}$, (if present) are selected from H, F, Cl, Br, Me, $CF_3$, and cyclopropyl and OMe. The remainder (if present) are H. In some of these embodiments, one or two of $R^A$, $R^B$, $R^C$ and $R^D$, (if present), and one or two of $R^{AA}$, $R^{BB}$, $R^{CC}$ and $R^{DD}$, (if present) are selected from H, F, Cl, Br, Me, and $CF_3$ and OMe. The remainder (if present) are H. In some of these embodiments, one or two of $R^A$, $R^B$, $R^C$ and $R^D$, (if present) and one or two of $R^{AA}$, $R^{BB}$, $R^{CC}$ and $R^{DD}$, (if present) are selected from H, F, Cl, Br and OMe. The remainder (if present) are H.

In some embodiments $R^A$, $R^{AA}$, $R^D$ and $R^{DD}$ are selected from H, F, Cl, Br, Me, $CF_3$, cyclopropyl, cyano and OMe; and $R^B$, $R^{BB}$, $R^C$ and $R^{CC}$ are H. In some embodiments $R^A$, $R^{AA}$, $R^D$ and $R^{DD}$ are selected from H, F, Cl, Br and OMe; and $R^B$, $R^{BB}$, $R^C$ and $R^{CC}$ are H.

In some embodiments $R^A$ and $R^{AA}$ are selected from H, F, Cl, Br, Me, $CF_3$, cyclopropyl, cyano, OMe, OEt and $CH_2OMe$. In some embodiments $R^A$ and $R^{AA}$ are selected from F, Cl, Br, Me, $CF_3$, cyclopropyl, cyano and OMe. In some embodiments $R^A$ and $R^{AA}$ are selected from Cl, Br and OMe. In some embodiments $R^A$ and $R^{AA}$ are selected from Cl, Br, Me and $CF_3$. In some embodiments $R^A$ and $R^{AA}$ are Cl. In some embodiments $R^A$ and $R^{AA}$ are Br. In some embodiments $R^A$ and $R^{AA}$ are OMe.

In some embodiments $R^D$ and $R^{DD}$ are selected from H, F, Cl, Br, Me, $CF_3$, cyclopropyl, cyano, OMe, $CH_2OH$, and $CH_2OMe$. In some embodiments $R^D$ and $R^{DD}$ are selected from H, F, Cl, Br, Me, $CF_3$, cyclopropyl, cyano and OMe. In some embodiments $R^D$ and $R^{DD}$ are selected from H, F, Br, Me and OMe. In some embodiments $R^D$ and $R^{DD}$ is selected from H and F. In some embodiments $R^D$ and $R^{DD}$ are H. In some embodiments $R^{D4}$ and $R^{DD}$ are F. In some embodiments $R^D$ and $R^{DD}$ are Br. In some embodiments $R^D$ and $R^{DD}$ are Me. In some embodiments $R^D$ and $R^{DD}$ are OMe.

In some embodiments, $A^1$, $A^2$, $A^3$, $A^4$, $A^{11}$, $A^{12}$, $A^{13}$ and $A^{14}$ are selected from combinations 1-10 in the following table:

| Combination | $A^1/A^{11}$ | $A^2/A^{12}$ | $A^3/A^{13}$ | $A^4/A^{14}$ |
|---|---|---|---|---|
| 1 | CCl | CH | CH | CH |
| 2 | CCl | CH | CH | $CCH_3$ |
| 3 | CCl | CH | CH | CBr |
| 4 | CBr | CH | CH | CH |
| 5 | CCl | CH | CH | CF |
| 6 | CCl | CH | CH | C—$OCH_3$ |
| 7 | CBr | CH | CH | CF |
| 8 | C—$OCH_3$ | CH | CH | CH |
| 9 | $CCF_3$ | H | H | H |
| 10 | $CCH_3$ | H | H | H |

In some embodiments, combinations 1, 4, 9 and 10 are preferred.

Y

In some embodiments, Y is $(CH_2)_n$, where n is from 2 to 3. In some embodiments, Y is $(CH_2)_2$. In some embodiments, Y is $(CH_2)_3$. In some embodiments, Y is $(CH_2)_4$.

$R^{C1}$, $R^{C3}$, $R^{C4}$, $R^{C11}$, $R^{C13}$ and $R^{C14}$

In some embodiments, $R^{C1}$, $R^{C3}$, $R^{C4}$, $R^{C11}$, $R^{C13}$ and $R^{C14}$ are all H.

In other embodiments, two of $R^{C1}$, $R^{C3}$ and $R^{C4}$ are H and two of $R^{C11}$, $R^{C13}$ and $R^{C14}$, and the others are selected from the defined groups (except H).

In other embodiments, one of $R^{C1}$, $R^{C3}$ and $R^{C4}$ is H and one of $R^{C11}$, $R^{C13}$ and $R^{C14}$, and the others are independently selected from the defined groups (except H). In some of these embodiments, $R^{C1}$ and $R^{C11}$ are OMe.

In some embodiments, $R^{C1}$, $R^{C3}$ and $R^{C4}$ are independently selected from H, Cl, F, Br, Me, OMe, OEt, cyano, $CF_3$ and $CH_2OH$. In some of these embodiments, $R^{C1}$, $R^{C3}$ and $R^{C4}$ are independently selected from H, Cl, F, $CF_3$, OMe and $CH_2OH$. In further of these embodiments, $R^{C1}$, $R^{C3}$ and $R^{C4}$ are independently selected from H, Cl and OMe.

In some embodiments, $R^{C11}$, $R^{C13}$ and $R^{C14}$ are independently selected from H, Cl, F, Br, Me, OMe, cyano, $CF_3$ and $CH_2OH$. In some of these embodiments, $R^{C11}$, $R^{C13}$ and $R^{C14}$ are independently selected from H, Cl, F, $CF_3$, OMe and $CH_2OH$. In further of these embodiments, $R^{C11}$, $R^{C13}$ and $R^{C14}$ are independently selected from H, Cl and OMe.

$W^1$ and $W^{11}$

In some embodiments, $W^1$ and $W^{11}$ are OH.

In other embodiments, $W^1$ and $W^{11}$ are $OR^P$, where $R^P$ is Me or Et.

OTHER EMBODIMENTS

In some embodiments, there is provided a compound of formula II:

(II)

wherein:
Y is $(CH_2)_n$, where n is from 2 to 4;
$W^1$ and $W^{11}$ are OH;
$A^1$ is $CR^A$ or N;
$A^2$ is $CR^B$ or N;
$A^3$ is $CR^C$ or N;
$A^4$ is $CR^D$ or N;
where no more than two of $A^1$, $A^2$, $A^3$, and $A^4$ may be N;
one or two of $R^A$, $R^B$, $R^C$ and $R^D$, (if present) are selected from H, F, Cl, Br, Me, $CF_3$, cyclopropyl, cyano, OMe, OEt, $CH_2OH$, $CH_2OMe$ and OH;
the remainder of $R^A$, $R^B$, $R^C$ and $R^D$, (if present) are H;
$A^{11}$ is $CR^{AA}$ or N;
$A^{12}$ is $CR^{BB}$ or N;
$A^{13}$ is $CR^{CC}$ or N;
$A^{14}$ is $CR^{DD}$ or N;
where no more than two of $A^{11}$, $A^{12}$, $A^{13}$ and $A^{14}$ may be N;
one or two of $R^{AA}$, $R^{BB}$, $R^{CC}$ and $R^{DD}$, (if present) are selected from H, F, Cl, Br, Me, $CF_3$, cyclopropyl, cyano, OMe, OEt, $CH_2OH$, $CH_2OMe$ and OH;
the remainder of $R^{AA}$, $R^{BB}$, $R^{CC}$ and $R^{DD}$, (if present) are H;
$R^{C1}$, $R^{C3}$ and $R^{C4}$ are independently selected from H, Cl, F, Br, Me, OMe, cyano, $CF_3$, $CH_2OH$, $CH_2OMe$, $C_{2-4}$alkenyl and $C_5$heterocyclyl;
$R^{C11}$, $R^{C13}$ and $R^{C14}$ are independently selected from H, Cl, F, Br, Me, OMe, cyano, $CF_3$, $CH_2OH$, $CH_2OMe$, $C_{2-4}$alkenyl and $C_5$heterocyclyl.

EXAMPLES

The following examples are provided solely to illustrate the present invention and are not intended to limit the scope of the invention, as described herein.

Acronyms

For convenience, many chemical moieties are represented using well known abbreviations, including but not limited to, methyl (Me), ethyl (Et), n-propyl (nPr), isopropyl (iPr), n-butyl (nBu), tert-butyl (tBu), phenyl (Ph), benzyl (Bn), methoxy (MeO), ethoxy (EtO), trimethylsilyl (TMS), and acetyl (Ac).

For convenience, many chemical compounds are represented using well known abbreviations, including but not limited to, methanol (MeOH), deuterated methanol (MeOD-$d_4$ or $CD_3OD$) ethanol (EtOH), isopropanol (i-PrOH), ether or diethyl ether ($Et_2O$), ethyl acetate (EtOAc), acetic acid (AcOH), acetonitrile (MeCN or ACN), dichloromethane (methylene chloride, DCM), trifluoroacetic acid (TFA), dimethylformamide (DMF), tetrahydrofuran (THF), dimethylsulfoxide (DMSO), deuterated chloroform ($CDCl_3$), diethylamine (DEA), deuterated dimethylsulfoxide (DMSO-$d_6$), N-ethyl-N'-(3-dimethylaminopropyl)carbodiimide hydrochloride (EDCl·HCl), meta-chloroperoxybenzoic acid (mCPBA), 1,1'-bis(diphenylphosphino)ferrocene (dppf), tert-butyloxycarbonyl (Boc, BOC), 2-(trimethylsilyl) ethoxymethyl (SEM), triethylamine ($Et_3N$ or TEA), 2-(1H-7-azabenzotriazol-1-yl)-1,1,3,3-tetramethyluronium hexafluorophosphate (HATU), 4-dimethylaminopyridine (DMAP), N,N-diisopropylethylamine (DIPEA or DIEA), 1,1'-bis(diphenylphosphino)ferrocene dichloropalladium (II) ($PdCl_2$(dppf)), trans-dichlorobis(triphenylphosphine) palladium(II) ($PdCl_2(PPh_3)_2$), tris(dibenzylideneacetone) dipalladium(0) ($Pd_2(dba)_3$), tetrakis(triphenylphosphine) palladium(0) ($Pd(PPh_3)_4$), propylphosphonic anhydride (T3P), hexamethylphosphoramide (HMPA), 1,2-dichloroethane (DCE), chromium(VI) oxide ($CrO_3$), n-bromosuccinimide (NBS), potassium hydroxide (KOH), benzoyl peroxide (BPO), carbon tetrachloride ($CCl_4$), petroleum ether (Pet. Ether), potassium carbonate ($K_2CO_3$), sodium sulfate ($Na_2SO_4$), lithium diisopropylamine (LDA), azobisisobutyronitrile (AIBN), N-methylmorpholine N-oxide (NMO), benzoyl peroxide (BPO) and 1-hydroxybenzotriazole (HOBt).

Other abbreviations: thin layer chromatography (TLC), retention time (rt).

General Experimental Details

Unless otherwise stated the following generalizations apply. $^1$H NMR spectra were recorded on a Bruker AVANCE III (400 MHz). The multiplicity of a signal is designated by the following abbreviations: s, singlet; d, doublet; t, triplet; q, quartet; dd, doublet of doublets; dt, doublet of triplets; tt, triplet of triplets; td, triplet of doublets; ddd, doublet of doublet of doublets br, broad; m, multiplet. All observed coupling constants, J, are reported in Hertz. Exchangeable protons are not always observed.

LCMS data was generated using the conditions described below. Chlorine isotopes are reported as $^{35}Cl$, Bromine isotopes are reported as either $^{79}Br$ or $^{81}Br$ or both $^{79}Br/^{81}Br$.

LC-MS Method A (LCMS-A):
Equipment Information
   LC model: Agilent 1200
   (Pump type: Binary Pump, Detector type: DAD)
   MS model: Agilent G6110A Quadrupole
Parameters of LCMS
   LC: Column: Xbridge-C18, 2.5 μm, 2.1×30 mm
   Column temperature: 30° C.
   Acquisition of wavelength: 214 nm, 254 nm
   Mobile phase: A: 0.07% HCOOH aqueous solution, B: MeOH
   MS: Ion source: ES+ (or ES−) MS range: 50~900 m/z
   Fragmentor: 60 Drying gas flow: 10 L/min
   Nebulizer pressure: 35 psi Drying gas temperature: 350° C.
   Vcap: 3.5 kV
Gradient Table:

| Flow (mL/min) | T (min) | A (%) | B (%) |
|---|---|---|---|
| 0.5 | 0.0 | 70 | 30 |
| 0.5 | 0.2 | 70 | 30 |
| 0.5 | 1.8 | 5 | 95 |
| 0.5 | 2.4 | 5 | 95 |
| 0.5 | 2.6 | 70 | 30 |
| 0.5 | 3.5 | 70 | 30 |

Sample Preparation

The sample was dissolved in methanol, the concentration about 0.11~1 mg/mL, then filtered through syringe filter with 0.22 μm. (Injection volume: 1~10 μL)

LC-MS Method B (LCMS-B):
Equipment Information
   LC model: Agilent 1200 (Pump type: Binary Pump, Detector type: DAD)
   MS model: Agilent G6110A Quadrupole
Parameters of LCMS
   LC: Column: Xbridge-C18, 2.5 μm, 2.1×30 mm
   Column temperature: 30° C.
   Acquisition of wavelength: 214 nm, 254 nm
   Mobile phase: A: 0.07% HCOOH aqueous solution, B: MeOH
   MS: Ion source: ES+ (or ES−) MS range: 50~900 m/z
   Fragmentor: 60 Drying gas flow: 10 L/min
   Nebulizer pressure: 35 psi Drying gas temperature: 350° C.
   Vcap: 3.5 kV
Gradient Table:

| Flow (mL/min) | T (min) | A (%) | B (%) |
|---|---|---|---|
| 0.5 | 0.0 | 70 | 30 |
| 0.5 | 0.3 | 70 | 30 |
| 0.5 | 0.6 | 50 | 50 |
| 0.5 | 0.9 | 40 | 60 |
| 0.5 | 1.2 | 30 | 70 |
| 0.5 | 3.2 | 5 | 95 |
| 0.5 | 3.5 | 5 | 95 |
| 0.5 | 4.0 | 70 | 30 |
| 0.5 | 5.0 | 70 | 30 |

Sample Preparation

The sample was dissolved in methanol, the concentration about 0.11~1 mg/mL, then filtered through the syringe filter with 0.22 μm. (Injection volume: 1~10 μL)

LC-MS Method C (LCMS-C):
Equipment Information
   LC model: Waters 2695 alliance (Pumptype: Quaternary Pump, Detector: 2996 Photodiode Array Detector)
   MS model: Micromass ZQ
Parameters of LCMS
   LC: Column: Xbridge-C18, 3.5 μm, 2.1×50 mm
   Column temperature: 30° C.
   Acquisition of wavelength: 214 nm, 254 nm
   Mobile phase: A: 0.07% HCOOH aqueous solution, B: MeOH
   MS: Ion source: ES+ (or ES−) MS range: 50~900 m/z
   Capillary: 3 kV Cone: 3 V Extractor: 3 V
   Drying gas flow: 600 L/hr Cone: 50 L/hr
   Desolvation temperature: 300° C.
   Source temperature: 100° C.
Gradient Table:

| Flow (mL/min) | T (min) | A (%) | B (%) |
|---|---|---|---|
| 0.3 | 0.0 | 80 | 20 |
| 0.3 | 0.5 | 80 | 20 |
| 0.3 | 0.8 | 50 | 50 |
| 0.3 | 1.2 | 35 | 65 |
| 0.3 | 2.0 | 20 | 80 |
| 0.3 | 4.0 | 5 | 95 |
| 0.3 | 5.0 | 5 | 95 |
| 0.3 | 5.8 | 15 | 85 |
| 0.3 | 6.2 | 80 | 20 |
| 0.3 | 8.0 | 80 | 20 |

Sample Preparation

The sample was dissolved in methanol, the concentration about 0.11~1 mg/mL, then filtered through the syringe filter with 0.22 μm. (Injection volume: 1~10 μL)

Preparative RP-HPLC:
   Instrument type: Varian 940-LC series;
   Pump type: Quaternary Pump;
   Detector type: Diode Array Detector
   HPLC conditions: Waters Sunfire prep C18 OBD, 5 μm 19×100 mm column, eluting with a gradient of MeOH in water with 0.07% TFA at a flow rate of 15 mL/min. Acquisition wavelength 214 nm, 254 nm.

Analytical thin-layer chromatography was performed on Merck silica gel 60 F254 aluminium-backed plates which were visualized using fluorescence quenching under UV light or a basic $KMnO_4$ dip or Ninhydrin dip.

Preparative thin-layer chromatography (prep TLC) was performed using Tklst (China), grand grade: (HPTLC): 8±2 μm>80%; (TLC): 10-40 μm. Type: GF254. Compounds were visualized by UV (254 nm).

Column chromatography was performed using Tklst (China), grand grade, 100-200 meshes silica gel.

Microwave irradiation was achieved using a CEM Explorer SP Microwave Reactor.

Where necessary, anhydrous solvents were purchased from Sigma-Aldrich or dried using conventional methods. Solutions of inorganic acids or bases were made up as aqueous solutions unless stated otherwise.

Additional Cartridges used are as follows:

Phase Separator:

Manufacturer: Biotage

Product: ISOLUTE® Phase Separator (3 mL unless otherwise stated)

SCX and SCX-2 Cartridges:

Manufacturer: Biotage

Product: ISOLUTE® SCX 1 g, (6 mL SPE Column unless otherwise stated)

Manufacturer: Biotage

Product: ISOLUTE® SCX-2 1 g (6 mL Column)

Manufacturer: Silicycle

Product: SCX-2 500 mg or 5 g

Manufacturer: Agilent

Product: Bond Elut® SCX 10 g

Sample Extraction Cartridge:

Manufacturer: Waters

Product: Oasis® HLB 35 cc (6 g) LP extraction cartridge

Solutions of hydrogen chloride, sodium hydroxide, potassium carbonate and sodium bicarbonate are aqueous, unless otherwise stated.

Intermediate Preparations (i) 4,4'-(Ethane-1,2-diylbis(azanediyl))bis(3-aminobenzamide) (I4)

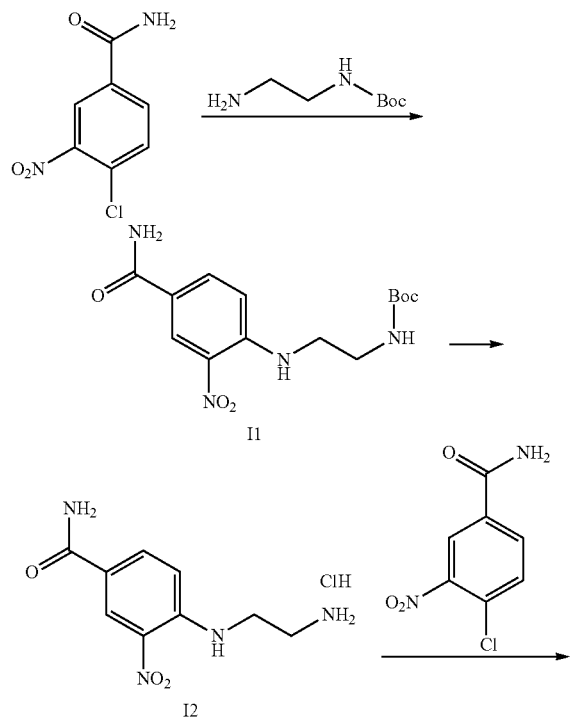

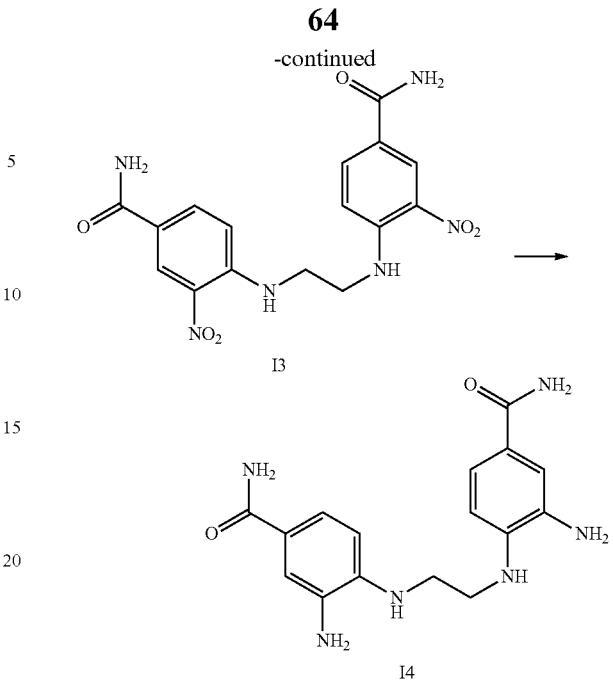

(a) tert-Butyl (2-((4-carbamoyl-2-nitrophenyl)amino)ethyl)carbamate (I1)

A suspension of 4-chloro-3-nitrobenzamide (8.0 g, 39.9 mmol), tert-butyl (2-aminoethyl)carbamate (6.40 g, 39.9 mmol) and $Et_3N$ (8.1 g, 79.8 mmol) in NMP (80 mL) was heated at 150° C. under $N_2$ overnight. Water (500 mL) was added followed by Pet. Ether/EtOAc (5:1, 300 mL) and the resulting precipitate was collected by filtration to give the title compound I1 (12.0 g, 92%) as a yellow solid. LCMS-B: rt 3.2 min, m/z 347.1 [M+Na]$^+$. $^1$H NMR (400 MHz, DMSO-$d_6$) δ 8.65 (s, 1H), 8.44 (t, J=5.8 Hz, 1H), 8.05-7.92 (m, 2H), 7.27 (s, 1H), 7.14 (d, J=9.1 Hz, 1H), 7.04 (t, J=5.8 Hz, 1H), 3.46-3.45 (m, 2H), 3.20-3.19 (m, 2H), 1.35 (s, 9H).

(b) 4-((2-Aminoethyl)amino)-3-nitrobenzamide hydrochloride (I2)

A mixture of tert-butyl (2-((4-carbamoyl-2-nitrophenyl)amino)ethyl)carbamate (I1) (12.0 g, 37.0 mmol) and a 5.5 M HCl in dioxane solution (200 mL) was stirred at room temperature overnight. The solvent was then removed under reduced pressure to give the title compound I2 (8.0 g, 96%) as a yellow solid. LCMS-B: rt 1.2 min, m/z 225.1 [M+H]$^+$. $^1$H NMR (400 MHz, DMSO-$d_6$) δ 8.65 (d, J=2.1 Hz, 1H), 8.42 (s, 1H), 8.25 (s, 2H), 8.05 (dd, J=9.0, 2.2 Hz, 1H), 7.25 (d, J=9.0 Hz, 1H), 5.62 (br s, 3H), 3.76-3.74 (m, 2H), 3.01-2.97 (m, 2H).

(c) 4,4'-(Ethane-1,2-diylbis(azanediyl))bis(3-nitrobenzamide) (I3)

A suspension of 4-((2-aminoethyl)amino)-3-nitrobenzamide hydrochloride (I2) (7.6 g, 33.9 mmol), 4-chloro-3-nitrobenzamide (6.80 g, 33.9 mmol) and $Et_3N$ (20.6 g, 203 mmol) in NMP (80 mL) was heated at 150° C. under $N_2$ overnight. Additional 4-((2-aminoethyl)amino)-3-nitrobenzamide hydrochloride (I2) (800 mg, 3.57 mmol) and $Et_3N$ (3.0 g, 29.6 mmol) were added and the mixture was heated at 150° C. under $N_2$ overnight. The mixture was allowed to cool to room temperature, diluted with Pet. Ether/EtOAc (1:1, v/v, 500 mL) and the resulting precipitate was collected by filtration to give the title compound I3 (12.0 g, 91%) as a yellow solid. LCMS-B: rt 1.3 min, m/z 389.0 [M+H]+. $^1$H NMR (400 MHz, DMSO-$d_6$) δ 8.62 (s, 4H), 7.99-7.95 (m, 4H), 7.30-7.28 (m, 4H), 3.70-3.64 (m, 4H).

(d) 4,4'-(Ethane-1,2-diylbis(azanediyl))bis(3-aminobenzamide) (I4)

A suspension of 4,4'-(ethane-1,2-diylbis(azanediyl))bis(3-nitrobenzamide) (I3) (12 g, 30.9 mmol), and 10% Pd/C (2.0 g) in DMF (200 mL) was heated at 100° C. under a $H_2$ atmosphere overnight. The mixture was filtered and the filtrate was concentrated under reduced pressure to give the title compound I4 (9.0 g, 90%) as a black solid. LCMS-B: rt 0.3 min, m/z 329.1 [M+H]+. $^1$H NMR (400 MHz, DMSO-$d_6$) δ 7.44 (s, 2H), 7.13 (d, J=8.2 Hz, 2H), 7.11 (s, 2H), 6.74 (s, 2H), 6.46 (d, J=8.0 Hz, 2H), 5.05 (s, 2H), 4.58 (s, 4H), 3.41-3.36 (m, 4H).

(ii) 4,4'-(Propane-1,3-diylbis(azanediyl))bis(3-aminobenzamide) (I8)

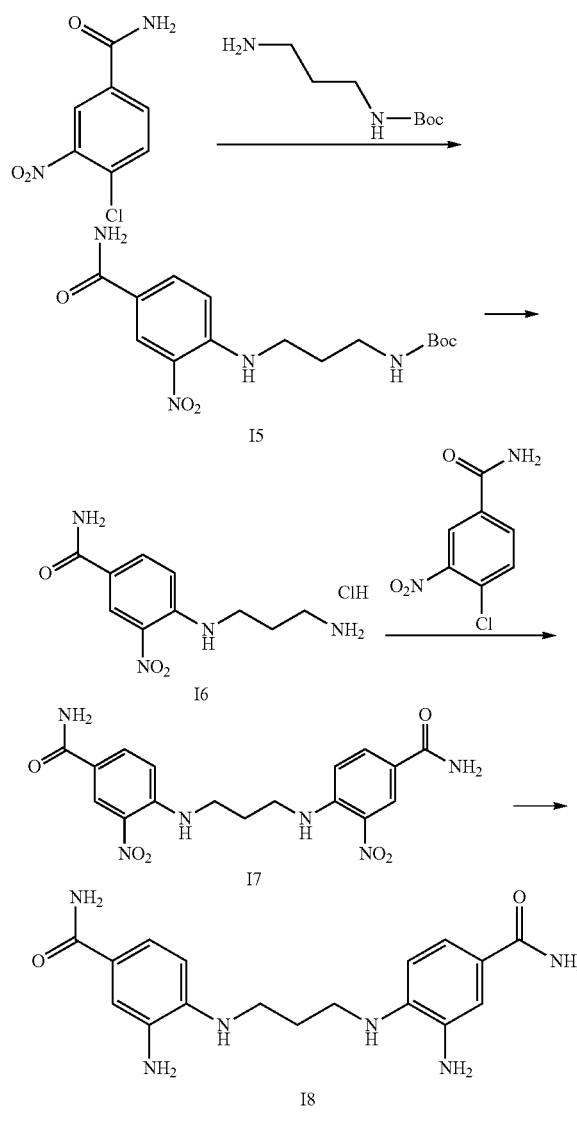

(a) tert-Butyl (3-((4-carbamoyl-2-nitrophenyl)amino)propyl)carbamate (I5)

To a solution of 4-chloro-3-nitrobenzamide (2 g, 10 mmol) in NMP (30 mL) was added tert-butyl (3-aminopropyl)carbamate (1.7 g, 9.97 mmol) and $Et_3N$ (2.1 g, 19.9 mmol) and the mixture was heated at 150° C. overnight. Water was added and the resulting mixture was extracted with EtOAc (150 mL×3). The combined organic extracts were washed with water, brine, dried over $Na_2SO_4$, filtered and concentrated under reduced pressure. The residue was purified by silica gel chromatography (DCM/MeOH=100:1 to 50:1) to give the title compound I5 (2.1 g, 62%) as a yellow solid. LCMS-B: rt 3.42 min, m/z 361.1 [M+Na]+.

(b) 4-((3-Aminopropyl)amino)-3-nitrobenzamide hydrochloride (I6)

A mixture of tert-butyl (3-((4-carbamoyl-2-nitrophenyl)amino)propyl)carbamate (I5) (2.1 g, 6.2 mmol) and a 6 M solution of HCl in dioxane (40 mL) was stirred at room temperature overnight. The solvent was then removed under reduced pressure to give the title compound I6 (1.5 g, 88%) as a yellow solid. LCMS-B: rt 0.29 min, m/z 239.3 [M+H]+.

(c) 4,4'-(Propane-1,3-diylbis(azanediyl))bis(3-nitrobenzamide) (I7)

To a mixture of 4-((3-aminopropyl)amino)-3-nitrobenzamide hydrochloride (I6) (2.0 g, 7.31 mmol) in NMP (50 mL) was added 4-chloro-3-nitrobenzamide (1.5 g, 7.31 mmol) and $Et_3N$ (2.2 g, 21.9 mmol) and the mixture was heated at 150° C. overnight. Water was added and the mixture was extracted with EtOAc (300 mL×3). The combined organic extracts were washed with water, brine, dried over $Na_2SO_4$, filtered and concentrated under reduced pressure. The residue was purified by silica gel chromatography (DCM/MeOH=100:1 to 50:1) to give the title compound I7 (1.3 g, 45%) as a black solid. LCMS-B: rt 2.98 min, m/z 403.1 [M+H]+. $^1$H NMR (400 MHz, DMSO-$d_6$) δ 8.65 (s, 2H), 8.60-8.48 (m, 2H), 7.99 (s, 4H), 7.29 (s, 2H), 7.12 (d, J=9.1 Hz, 2H), 3.62-3.48 (m, 4H), 2.01-1.88 (m, 2H).

(d) 4,4'-(Propane-1,3-diylbis(azanediyl))bis(3-aminobenzamide) (I8)

To a solution of 4,4'-(propane-1,3-diylbis(azanediyl))bis(3-nitrobenzamide) (I7) (1 g, 2.5 mmol) in DMF (30 mL) was added 10% Pd/C (100 mg) and the mixture was heated at 90° C. under a $H_2$ atmosphere overnight. The mixture was filtered and the filtrate was concentrated under reduced pressure to give the title compound I8 (777 mg, 91%) as a black solid. LCMS-B: rt 0.27 min, m/z 343.1 [M+H]+. $^1$H NMR (400 MHz, DMSO-$d_6$) δ 7.41 (s, 2H), 7.17-6.96 (m, 4H), 6.69 (s, 2H), 6.48-6.29 (m, 2H), 5.22-4.12 (m, 6H), 3.27-3.12 (m, 4H), 1.99-1.87 (m, 2H).

(iii) 4,4'-(Butane-1,4-diylbis(azanediyl))bis(3-aminobenzamide) (I12)

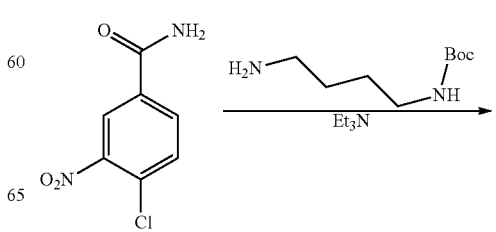

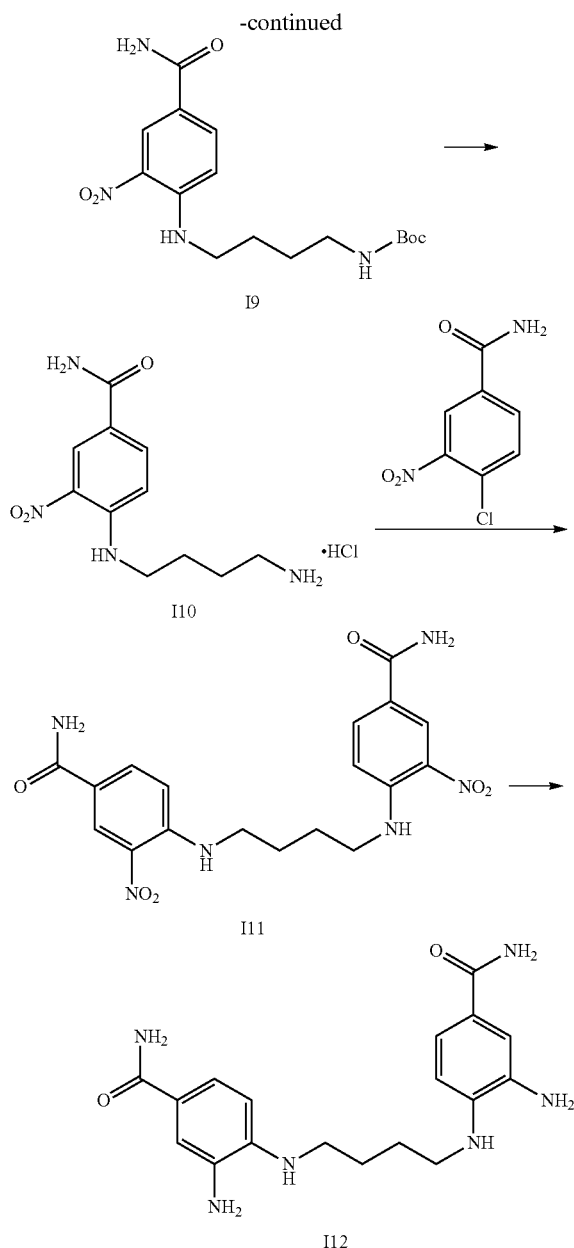

(a) tert-Butyl (4-((4-carbamoyl-2-nitrophenyl)amino)butyl)carbamate (I9)

To a solution of 4-chloro-3-nitrobenzamide (2.0 g, 10.0 mmol) in NMP (20 mL) was added tert-butyl (4-aminobutyl)carbamate (2.24 g, 10.0 mmol) and Et$_3$N (2.02 g, 20.0 mmol) and the mixture was heated at 150° C. overnight. The mixture was partitioned between water (100 mL) and EtOAc (100 mL), the layers were separated and the aqueous layer was extracted with EtOAc (100 mL×3). The combined organic layers were washed with brine (100 mL), dried over Na$_2$SO$_4$, filtered and concentrated under reduced pressure. The residue was purified by silica gel chromatography (DCM/MeOH=100:1 to 40:1) to give the title compound I9 (2.0 g, 57%) as a yellow solid. LCMS-B: rt 3.44 min, m/z 375.1 [M+Na]$^+$.

(b) 4-((4-Aminobutyl)amino)-3-nitrobenzamide hydrochloride (I10)

A mixture of tert-butyl (4-((4-carbamoyl-2-nitrophenyl)amino)butyl)carbamate (I9) (2.27 g, 6.44 mmol) and a 6 M HCl in dioxane solution (30 mL) was stirred at room temperature for 16 h. The solvent was removed under reduced pressure to give the title compound I10 (1.61 g, 100%) as a yellow solid. LCMS-B: rt 3.47 min, m/z 253.1 [M+H]$^+$.

(c) 4,4'-(Butane-1,4-diylbis(azanediyl))bis(3-nitrobenzamide) (I11)

To a solution of 4-((4-aminobutyl)amino)-3-nitrobenzamide hydrochloride (I10) (1.50 g, 5.95 mmol) in NMP (50 mL) was added 4-chloro-3-nitrobenzamide (1.19 g, 5.95 mmol) and Et$_3$N (1.81 g, 17.85 mmol) and the mixture was heated at 150° C. for 16 h. The mixture was partitioned between water (200 mL) and EtOAc (200 mL) which resulted in a precipitate forming. The precipitate was collected by filtration to give the title compound I11 (1.22 g, 49%) as a black solid. LCMS-B: rt 3.12 min, m/z 417.1 [M+H]$^+$. $^1$H NMR (400 MHz, DMSO-d$_6$) δ 8.64 (s, 2H), δ 8.41 (s, 2H), 8.10-7.88 (m, 4H), 7.27 (s, 2H), 7.12 (d, J=8.7 Hz, 2H), 3.55-3.40 (m, 4H), 1.73 (s, 4H).

(d) 4,4'-(Butane-1,4-diylbis(azanediyl))bis(3-aminobenzamide) (I12)

To a solution of 4,4'-(butane-1,4-diylbis(azanediyl))bis(3-nitrobenzamide) (I11) (1.0 g, 2.40 mmol) in DMF (20 mL) was added 10% Pd/C (100 mg) and the mixture was heated at 90° C. under a H$_2$ atmosphere for 16 h. The mixture was filtered and the filtrate was concentrated under reduced pressure to give the title compound I12 (842 mg, 98%) as a black solid. LCMS-B: rt 0.32 min, m/z 357.2 [M+H]$^+$. $^1$H NMR (400 MHz, DMSO-d$_6$) δ 7.41 (s, 2H), 7.16-7.04 (m, 4H), 6.71 (s, 2H), 6.39 (d, J=8.2 Hz, 2H), 4.92 (s, 2H), 4.60 (s, 4H), 3.13 (s, 4H), 1.73 (s, 4H).

(iv) Ethyl 3-formyl-4-methoxybenzo[b]thiophene-2-carboxylate (I16)

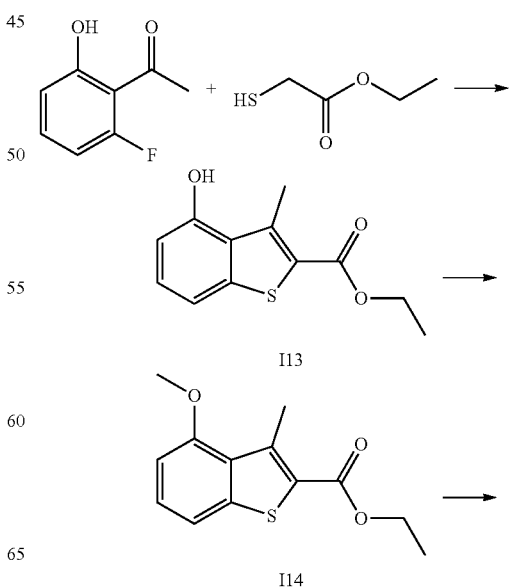

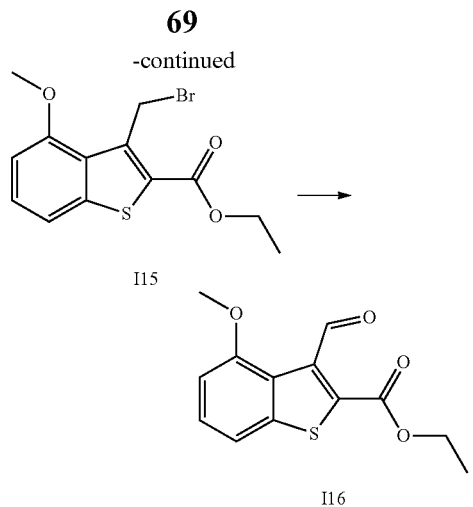

(a) Ethyl 4-hydroxy-3-methylbenzo[b]thiophene-2-carboxylate (I13)

To a solution of 1-(2-fluoro-6-hydroxyphenyl)ethan-1-one (2.0 g, 3.24 mmol) in DMF (20 mL) was added ethyl 2-mercaptoacetate (2.4 g, 4.86 mmol) and $K_2CO_3$ (3.6 g, 26.1 mmol) and the mixture was heated at 100° C. under nitrogen overnight. Water (100 mL) was added and the mixture was extracted with EtOAc (100 mL×3). The combined organic extracts were washed with water (100 mL×3), brine (100 mL), dried over $Na_2SO_4$, filtered and concentrated under reduced pressure. The residue was purified by silica gel chromatography (Pet. Ether/EtOAc=1:0 to 10:1) to give the title compound I13 (1.8 g, 60%) as a grey solid. LCMS-A: rt 2.64 min; m/z 259.0 [M+Na]$^+$.

(b) Ethyl 4-methoxy-3-methylbenzo[b]thiophene-2-carboxylate (I14)

To a solution of ethyl 4-hydroxy-3-methylbenzo[b]thiophene-2-carboxylate (I13) (350 mg, 1.48 mmol) and methyl iodide (2.1 g, 14.8 mmol) in DMF (8 mL) was added $K_2CO_3$ (613 mg, 4.44 mmol) and the mixture was stirred at room temperature in a sealed tube overnight. Water was added and the mixture was extracted with EtOAc. The combined organic extracts were washed with water, brine, dried over $Na_2SO_4$, filtered and concentrated under reduced pressure. The residue was purified by silica gel chromatography (Pet. Ether/EtOAc=10:1) to give the title compound I14 (380 mg, 100%). LCMS-A: rt 2.65 min; m/z 251.0 [M+H]$^+$.

(c) Ethyl 3-(bromomethyl)-4-methoxybenzo[b]thiophene-2-carboxylate (I15)

To a suspension of ethyl 4-methoxy-3-methylbenzo[b]thiophene-2-carboxylate (I14) (380 mg, 1.48 mmol) and NBS (268 mg, 1.50 mmol) in $CCl_4$ (20 mL) was added BPO (92 mg, 0.38 mmol) and the mixture was heated at reflux overnight. Water was added and the mixture was extracted with EtOAc. The organic extract was washed with water, brine, dried over $Na_2SO_4$, filtered and concentrated under reduced pressure. The residue was purified by silica gel chromatography (Pet. Ether/EtOAc=10/1) to give the title compound (360 mg, 76%). LCMS-A: rt 2.73 min; m/z 350.8/352.9 [M+Na]$^+$.

(d) Ethyl 3-formyl-4-methoxybenzo[b]thiophene-2-carboxylate (I16)

To a solution of ethyl 3-(bromomethyl)-4-methoxybenzo[b]thiophene-2-carboxylate (I15) (1.0 g, 3.0 mmol) in THF (30 mL) was added NMO (1.41 g, 12.0 mmol) and the mixture was heated at reflux overnight. The mixture was allowed to cool to room temperature, poured into water (50 mL) and extracted with EtOAc (50 mL×3). The combined organic extracts were washed with water, brine, dried over $Na_2SO_4$, filtered and concentrated under reduced pressure. The residue was purified by silica gel chromatography (Pet. Ether/EtOAc=50:1 to 10:1) to give the title compound (330 mg, 42%) as a yellow solid. LCMS-B: rt 4.0 min; m/z 265.0 [M+H]$^+$. $^1$H NMR (400 MHz, DMSO-d$_6$) δ 10.6 (s, 1H), 7.67 (dd, J=8.2, 0.8 Hz, 1H), 7.55 (t, J=8.1 Hz, 1H), 7.05 (d, J=8.0 Hz, 1H), 4.32 (q, J=7.1 Hz, 2H), 3.90 (s, 3H), 1.30 (t, J=7.1 Hz, 3H).

(v) Ethyl 4-chloro-3-formylbenzo[b]thiophene-2-carboxylate (I19)

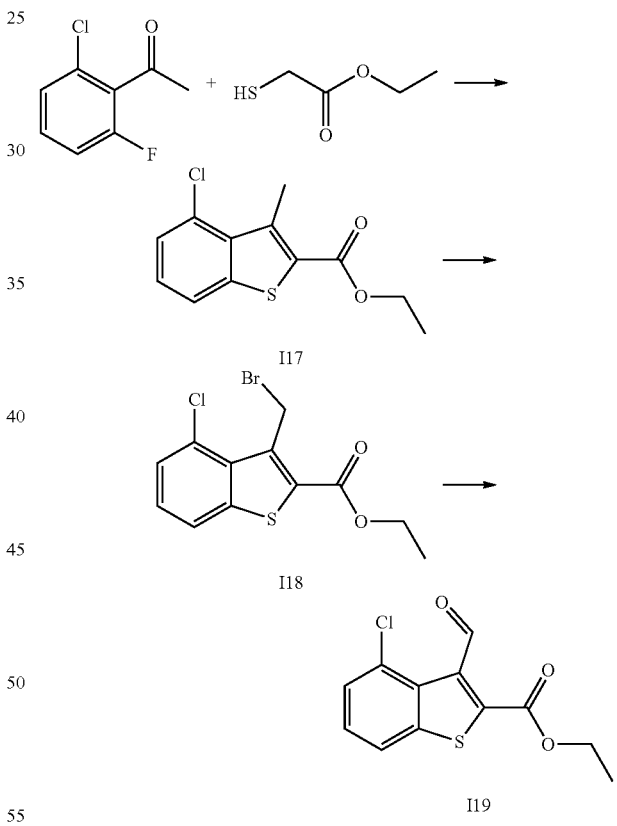

(a) Ethyl 4-chloro-3-methylbenzo[b]thiophene-2-carboxylate (I17)

A solution of 1-(2-chloro-6-fluorophenyl)ethanone (25.0 g, 145 mmol), ethyl 2-mercaptoacetate (17.4 g, 145 mmol) and $K_2CO_3$ (30.0 g, 217 mmol) in DMF (200 mL) was heated at 100° C. overnight. The mixture was allowed to cool to room temperature then poured into water (1.0 L) and EtOAc (500 mL). The organic layer was separated and the aqueous layer was extracted with EtOAc (500 mL×3). The combined organic extracts were dried over anhydrous Na₂SO₄, filtered and concentrated under reduced pressure. The residue was purified by re-crystallization from Pet. Ether/EtOAc to give the title compound I17 (28.0 g, 76%) as a yellow solid. LCMS-A: rt 2.82 min; m/z 255.0 [M+H]⁺.

(b) Ethyl 3-(bromomethyl)-4-chlorobenzo[b]thiophene-2-carboxylate (I18)

A suspension of ethyl 4-chloro-3-methylbenzo[b]thiophene-2-carboxylate (I17) (28.0 g, 0.11 mol), NBS (19.6 g, 0.11 mol) and BPO (2.67 g, 0.011 mol) in CCl₄ (200 mL) was heated at 115° C. for 1.5 h. The mixture was allowed to cool to room temperature then concentrated under reduced pressure and the residue was purified by re-crystallization from DCM/Pet. Ether to give the title compound I18 (26.0 g, 71%) as a purple solid. ¹H NMR (400 MHz, CDCl₃) δ 7.74 (dd, J=8.0, 1.2 Hz, 1H), 7.46 (dd, J=7.6, 0.8 Hz, 1H), 7.40 (t, J=8.0 Hz, 1H), 5.61 (s, 2H), 4.44 (q, J=7.1 Hz 2H), 1.44 (t, J=7.1 Hz, 3H).

(c) Ethyl 4-chloro-3-formylbenzo[b]thiophene-2-carboxylate (I19)

A mixture of ethyl 3-(bromomethyl)-4-chlorobenzo[b]thiophene-2-carboxylate (I18) (10.00 g, 29.97 mmol) and NMO (14.00 g, 119.88 mmol) in THF (250 mL) was heated at reflux for 16 h. The mixture was concentrated under reduced pressure and the residue was purified by silica gel chromatography (Pet. Ether/EtOAc=100:1 to 50:1) to give the title compound I19 (2.70 g, 34%) as a white solid. LCMS-B: rt 4.16 min, m/z 269.0 [M+H]⁺, 290.9 [M+Na]⁺. ¹H NMR (400 MHz, DMSO-d₆) δ 10.7 (s, 1H), 8.17 (dd, J=7.6, 1.5 Hz, 1H), 7.66-7.58 (m, 2H), 4.36 (q, J=7.1 Hz, 2H), 1.32 (t, J=7.1 Hz, 3H).

(vi) Ethyl 4-chloro-7-fluoro-3-formylbenzo[b]thiophene-2-carboxylate (I24)

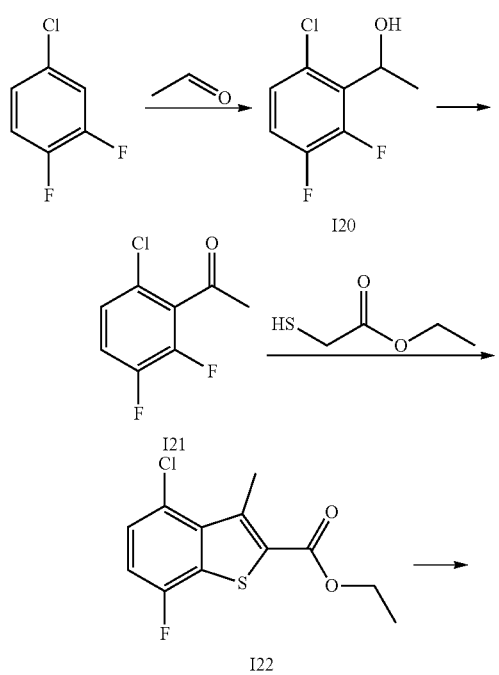

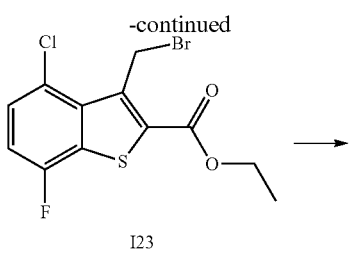

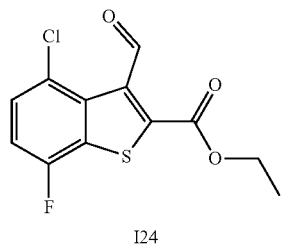

(a) 1-(6-Chloro-2,3-difluorophenyl)ethan-1-ol (I20)

To a solution of diisopropylamine (4.4 g, 43.9 mmol) in dry THF (100 mL) at −78° C. under nitrogen was added n-BuLi (2.5 M solution in n-hexane, 17.6 mL, 43.9 mmol) dropwise followed by 4-chloro-1,2-difluorobenzene (5.0 g, 33.8 mmol) and the mixture was stirred for 1 h. Acetaldehyde (4.4 g, 101.4 mmol) was added dropwise and the mixture was allowed to warm to room temperature and stirred overnight. The reaction mixture was quenched by addition of a saturated aqueous NH₄Cl solution and the aqueous phase was extracted with EtOAc. The combined organic extracts were dried over Na₂SO₄, filtered and concentrated under reduced pressure. The residue was purified by silica gel chromatography (Pet. Ether/EtOAc=1:0 to 20:1) to give the title compound I20 (3.0 g, 46%) as a yellow oil. LCMS-B: rt 3.39 min; m/z 175.0 [M−OH]⁺. ¹H NMR (400 MHz, DMSO-d₆) δ 7.41-7.33 (m, 1H), 7.31-7.25 (m, 1H), 5.54 (d, J=4.4 Hz, 1H), 5.25-5.16 (m, 1H), 1.45 (d, J=6.7 Hz, 3H).

(b) 1-(6-Chloro-2,3-difluorophenyl)ethan-1-one (I21)

To a solution of 1-(6-chloro-2,3-difluorophenyl)ethan-1-ol (I20) (3.0 g, 15.6 mmol) in dry DCM (50 mL) was added Dess-Martin periodinane (19.8 g, 46.7 mmol) and the mixture was stirred at room temperature overnight. The mixture was filtered and the filtrate diluted with water and extracted with EtOAc. The combined organic extracts were washed with a saturated aqueous NaHCO₃ solution, dried over Na₂SO₄, filtered and concentrated under reduced pressure. The residue was purified by silica gel chromatography (Pet. ether) to give the title compound I21 (2.3 g, 79%) as yellow oil, which was used directly in the next step.

(c) Ethyl 4-chloro-7-fluoro-3-methylbenzo[b]thiophene-2-carboxylate (I22)

To a mixture of 1-(6-chloro-2,3-difluorophenyl)ethan-1-one (I21) (1.8 g, 9.3 mmol) and K₂CO₃ (3.9 g, 28.0 mmol) in DMF (20 mL) under nitrogen was added ethyl 2-mercaptoacetate (1.3 g, 11.2 mmol) and the mixture was stirred at room temperature overnight. Water was added and the mixture was extracted with EtOAc. The combined organic extracts were washed with water, brine and concentrated under reduced pressure. The residue was purified by silica gel chromatography (Pet. Ether/EtOAc=1:0) to give the title compound I22 (1.5 g, 60%) as a brown solid. LCMS-A: rt 3.54 min; m/z 273.0 [M+H]⁺. $^1$H NMR (400 MHz, DMSO-d$_6$) δ 7.55-7.50 (m, 1H), 7.40 (t, J=8.7 Hz, 1H), 4.35 (q, J=7.1 Hz, 2H), 2.97 (s, 3H), 1.34 (t, J=7.1 Hz, 3H).

(d) Ethyl 3-(bromomethyl)-4-chloro-7-fluorobenzo[b]thiophene-2-carboxylate (I23)

To a solution of ethyl 4-chloro-7-fluoro-3-methylbenzo[b]thiophene-2-carboxylate (I22) (1.5 g, 5.5 mmol) in CCl$_4$ (50 mL) was added NBS (978 mg, 5.5 mol) and AIBN (451 mg, 2.75 mmol) and the mixture was heated at 80° C. under N$_2$ overnight. The mixture was diluted with water, extracted with EtOAc and the combined organic extracts were washed with water, brine and concentrated under reduced pressure to give the title compound I23 (1.3 g, 80%) as a yellow solid. $^1$H NMR (400 MHz, DMSO-d$_6$) δ 7.67-7.61 (m, 1H), 7.50 (t, J=8.7 Hz, 1H), 5.47 (s, 2H), 4.41 (q, J=7.1 Hz, 2H), 1.36 (t, J=7.0 Hz, 3H).

(e) Ethyl 4-chloro-7-fluoro-3-formylbenzo[b]thiophene-2-carboxylate (I24)

To a solution of ethyl 3-(bromomethyl)-4-chloro-7-fluorobenzo[b]thiophene-2-carboxylate (I23) (1.0 g, 2.8 mmol) in THF (20 mL) under N$_2$ was added NMO (1.33 g, 11.4 mmol) and the mixture was heated at reflux for 16 h. The mixture was diluted with water, extracted with EtOAc and the combined organic extracts were washed with brine, dried over Na$_2$SO$_4$, filtered and concentrated under reduced pressure. The residue was purified by silica gel chromatography (Pet. Ether/EtOAc=1:0 to 100:1) to give the title compound I24 (250 mg, 31%) as a white solid. LCMS-B: rt 4.39 min; m/z 286.9 [M+H]⁺, 308.9 [M+Na]⁺. $^1$H NMR (400 MHz, DMSO-d$_6$) δ 10.7 (s, 1H), 7.73-7.66 (m, 1H), 7.57 (t, J=8.9 Hz, 1H), 4.38 (q, J=7.1 Hz, 2H), 1.32 (t, J=7.1 Hz, 3H).

(vii) 4,4'-(Ethane-1,2-diylbis(azanediyl))bis(3-amino-2-methoxybenzamide) (I33)

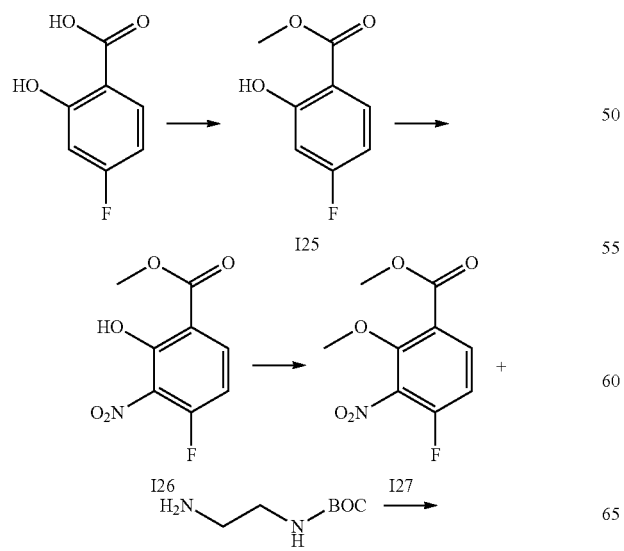

-continued

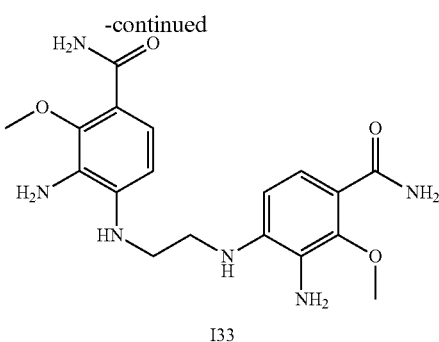

I33

(a) Methyl 4-fluoro-2-hydroxybenzoate (I25)

A mixture of 4-fluoro-2-hydroxybenzoic acid (50.0 g, 320.3 mmol) and concentrated $H_2SO_4$ (40 mL, 672.7 mmol) in MeOH (600 mL) was heated at reflux under $N_2$ for 16 h. The mixture was poured into water (500 mL) and extracted with EtOAc (500 mL×3). The combined organic extracts were washed with water (500 mL×2), brine (500 mL), dried over $Na_2SO_4$, filtered and concentrated under reduced pressure. The residue was purified by silica gel chromatography (Pet. Ether/EtOAc=100:1 to 20:1) to give the title compound (50.0 g, 91%) as a white solid. LCMS-A (ES-API): rt 1.80 min, m/z 171.1 $[M+H]^+$. $^1H$ NMR (400 MHz, DMSO-$d_6$) δ 10.8 (s, 1H), 7.83 (dd, J=8.9, 6.8 Hz, 1H), 6.90-6.70 (m, 2H), 3.88 (s, 3H).

(b) Methyl 4-fluoro-2-hydroxy-3-nitrobenzoate (I26)

To a solution of methyl 4-fluoro-2-hydroxybenzoate (I25) (50.0 g, 294.0 mmol) in concentrated $H_2SO_4$ (100 mL) at 0° C. under $N_2$ was added concentrated $HNO_3$ (20 mL, 382.1 mmol) dropwise and the mixture was allowed to warm to room temperature and stirred for 16 h. The mixture was slowly poured into water (2.0 L) and extracted with EtOAc (1.5 L×3). The combined organic extracts were washed water (1.5 L×2), brine (1.5 L), dried over $Na_2SO_4$, filtered and concentrated under reduced pressure. The residue was purified by silica gel chromatography (100% Pet. Ether) to give a mixture of the title compound and an uncharacterised regioisomer (50 g, ~3.75:1 uncharacterised regioisomer/title compound). The mixture was used in the next step without further purification or characterization. LCMS-A (ES-API): rt 1.57 min (minor) m/z 216.0 $[M+H]^+$ and rt 1.68 min (major) m/z 216.1 $[M+H]^+$.

(c) Methyl 4-fluoro-2-methoxy-3-nitrobenzoate (I27)

A mixture of methyl 4-fluoro-2-hydroxy-3-nitrobenzoate (containing a major, uncharacterised regioisomer) (I26) (50.0 g), $CH_3I$ (99.0 g, 697 mmol) and $K_2CO_3$ (64.1 g, 465 mml) in DMF (200 mL) was stirred at room temperature under $N_2$ for 16 h. The mixture was poured into water (1.0 L), extracted with EtOAc (1.0 L×3) and the combined organic extracts were washed water (1.0 L×2), brine (1.0 L), dried over $Na_2SO_4$, filtered and concentrated under reduced pressure. The residue was purified by silica gel chromatography (Pet. Ether/EtOAc=100:1 to 40:1) and the fractions containing the minor component were collected to give the title compound (14.0 g, 21% over two steps) as a white solid. LCMS-C (ES-API): rt 3.53 min, m/z 230.0 $[M+H]^+$. $^1H$ NMR (400 MHz, DMSO-$d_6$) δ 8.12 (dd, J=9.1, 6.5 Hz, 1H), 7.50 (t, J=9.0 Hz, 1H), 3.93 (s, 3H), 3.91 (s, 3H).

(d) Methyl 4-((2-((tert-butoxycarbonyl)amino)ethyl)amino)-2-methoxy-3-nitrobenzoate (I28)

A mixture of methyl 4-fluoro-2-methoxy-3-nitrobenzoate (I27) (6.0 g, 26.2 mmol), tert-butyl (2-aminoethyl) carbamate (4.2 g, 26.2 mmol) and $Et_3N$ (5.3 g, 52.4 mmol) in NMP (100 mL) was heated at 80° C. under $N_2$ for 16 h. The mixture was poured into water (500 mL), extracted with EtOAc (500 mL×3) and the combined organic extracts were washed with water (500×2 mL), brine (500 mL), dried over $Na_2SO_4$, filtered and concentrated under reduced pressure. The residue was purified by silica gel chromatography (Pet. Ether/EtOAc=100:1 to 10:1) to give the title compound (9.5 g, 98%) as a yellow solid. LCMS-C (ES-API): rt 4.43 min, m/z 392.1 $[M+Na]^+$. $^1H$ NMR (400 MHz, DMSO-$d_6$) δ 7.79 (d, J=9.2 Hz, 1H), 6.96 (t, J=5.5 Hz, 1H), 6.74 (d, J=9.2 Hz, 1H), 6.70 (t, J=5.7 Hz, 1H), 3.79 (s, 6H), 3.27-3.21 (m, 2H), 3.11-3.06 (m, 2H), 1.37 (s, 9H).

(e) Methyl 4-((2-aminoethyl)amino)-2-methoxy-3-nitrobenzoate hydrochloride (I29)

A mixture of methyl 4-((2-((tert-butoxycarbonyl)amino)ethyl)amino)-2-methoxy-3-nitrobenzoate (I28) (9.5 g, 25.7 mmol) and a 3 M HCl in dioxane solution (200 mL) was stirred at room temperature under $N_2$ for 16 h. The mixture was concentrated under reduced pressure to give the title compound (6.0 g, 87%) as a white solid. LCMS-C (ES-API): rt 0.82 min, m/z 270.0 $[M+H]^+$. $^1H$ NMR (400 MHz, DMSO-$d_6$) δ 7.81 (dd, J=9.2, 3.8 Hz, 1H), 6.82-6.71 (m, 2H), 3.79 (s, 3H), 3.75 (s, 3H), 3.31-3.28 (m, 4H).

(f) Dimethyl 4,4'-(ethane-1,2-diylbis(azanediyl))bis(2-methoxy-3-nitrobenzoate) (I30)

A mixture of methyl 4-((2-aminoethyl)amino)-2-methoxy-3-nitrobenzoate hydrochloride (I29) (5.5 g, 18.0 mmol), methyl 4-fluoro-2-methoxy-3-nitrobenzoate I27 (4.68 g, 20.4 mmol) and $Et_3N$ (6.2 g, 61.3 mmol) in NMP (100 mL) was heated at 80° C. under $N_2$ for 16 h. The mixture was poured into water (600 mL) and the resulting precipitate was collected by filtration to give the title compound (8.0 g, 82%) as a yellow solid. LCMS-C (ES-API): rt 4.75 min, m/z 477.1 $[M-H]^-$. $^1H$ NMR (400 MHz, DMSO-$d_6$) δ 7.76 (d, J=9.2 Hz, 2H), 6.77-6.74 (m, 4H), 3.78 (s, 6H), 3.77 (s, 6H), 3.40 (br s, 4H).

(g) 4,4'-(Ethane-1,2-diylbis(azanediyl))bis(2-methoxy-3-nitrobenzoic acid) (I31)

A mixture of dimethyl 4,4'-(ethane-1,2-diylbis(azanediyl))bis(2-methoxy-3-nitrobenzoate) (I30) (4.0 g, 8.4 mmol) and NaOH (2.0 g, 50.2 mmol) in EtOH/water (50 mL/50 mL) was heated at 80° C. for 16 h. Most of the EtOH was removed under reduced pressure and the residue was diluted with water (50 mL) and acidified to pH 4-5 with a 2 M aqueous HCl solution. The resulting precipitate was collected by filtration to give the title compound (3.5 g, 93%) as a yellow solid. LCMS-C (ES-API): rt 3.45 min, m/z 473.1 $[M+Na]^+$. $^1H$ NMR (400 MHz, DMSO-$d_6$) δ 12.6 (br s, 2H), 7.77 (d, J=9.1 Hz, 2H), 6.74 (d, J=9.3 Hz, 2H), 6.69 (t, J=5.5 Hz, 2H), 3.78 (s, 6H), 3.44 (br s, 4H).

(h) 4,4'-(Ethane-1,2-diylbis(azanediyl))bis(2-methoxy-3-nitrobenzamide) (I32)

A mixture of 4,4'-(ethane-1,2-diylbis(azanediyl))bis(2-methoxy-3-nitrobenzoic acid) (I31) (3.4 g, 7.6 mmol), NH$_4$Cl (2.4 g, 45.3 mmol), HOBt (3.1 g, 22.7 mmol), EDCl·HCl (4.3 g, 22.7 mmol) and DIPEA (5.9 g, 45.3 mmol) in DMF (300 mL) was stirred at room temperature under N$_2$ for 16 h. The mixture was poured into water (600 mL) and the resulting precipitate was collected by filtration to give the title compound (2.4 g, 71%) as a yellow solid. LCMS-C (ES-API): rt 3.02 min, m/z 471.1 [M+Na]$^+$. $^1$H NMR (400 MHz, DMSO-d$_6$) δ 7.63 (d, J=9.0 Hz, 2H), 7.42 (br s, 4H), 6.77 (d, J=9.1 Hz, 2H), 6.60 (t, J=4.8 Hz, 2H), 3.77 (s, 6H), 3.39-3.36 (m, 4H).

(i) 4,4'-(Ethane-1,2-diylbis(azanediyl))bis(3-amino-2-methoxybenzamide) (I33)

A mixture of 4,4'-(ethane-1,2-diylbis(azanediyl))bis(2-methoxy-3-nitrobenzamide) (I32) (1.0 g, 2.3 mmol) and 10% Pd/C (200 mg) in MeOH (150 mL) was stirred at room temperature under a H$_2$ atmosphere (3 MPa) for 3 days. The mixture was filtered and the filtrate was concentrated under reduced pressure give the title compound (120 mg). The filter cake was washed with DMSO and the filtrate was freeze-dried to give additional title compound (680 mg). The isolated solids were combined to give the title compound (800 mg, 92%) as a brown solid. LCMS-B (ES-API): rt 1.09 min, m/z 388.8 [M+H]$^+$. $^1$H NMR (400 MHz, DMSO-d$_6$) δ 7.39 (br s, 2H), 7.11 (d, J=8.4 Hz, 2H), 7.10 (br s, 2H), 6.37 (d, J=8.5 Hz, 2H), 5.23 (br s, 2H), 4.42 (br s, 4H), 3.66 (s, 6H), 3.35 (br s, 4H).

(viii) Ethyl 3-formylbenzo[b]thiophene-2-carboxylate (I36)

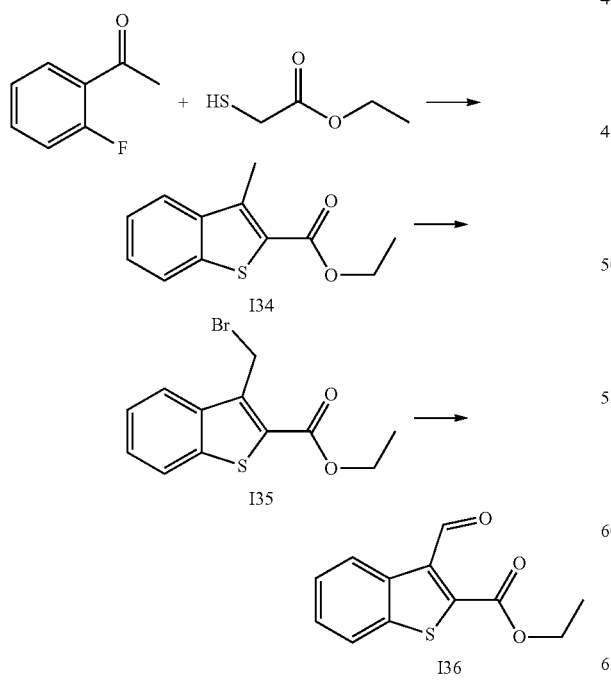

(a) Ethyl 3-methylbenzo[b]thiophene-2-carboxylate (I34)

A solution of 1-(2-fluorophenyl)ethan-1-one (25.0 g, 181 mmol), ethyl 2-mercaptoacetate (26.1 g, 217 mmol) and K$_2$CO$_3$ (75.1 g, 543 mmol) in DMF (250 mL) was heated at 75° C. under N$_2$ for 16 h. Water was added and the resulting mixture was extracted EtOAc. The combined organic extracts were dried over Na$_2$SO$_4$, filtered and concentrated under reduced pressure. The residue was purified by silica gel chromatography (Pet. Ether/EtOAc=100:0 to 100:1) to give the title compound (38.8 g, 97%) as a light green solid. LCMS-B (ES-API): rt 4.51 min; m/z 221.1 [M+H]$^+$.

(b) Ethyl 3-(bromomethyl)benzo[b]thiophene-2-carboxylate (I35)

A solution of ethyl 3-methylbenzo[b]thiophene-2-carboxylate (I34) (10.0 g, 45.4 mmol), NBS (8.08 g, 45.4 mmol) and BPO (1.09 g, 4.5 mmol) in CCl$_4$ (200 mL) was heated at reflux under N$_2$ for 16 h. Water was added and the resulting mixture was extracted with EtOAc. The combined organic extracts were dried over Na$_2$SO$_4$, filtered and concentrated under reduced pressure. The residue was purified by silica gel chromatography (DCM) to give title compound (11.8 g, 86%) as a light yellow solid. $^1$H NMR (400 MHz, DMSO-d$_6$) δ 8.11-8.08 (m, 2H), 7.61-7.57 (m, 2H), 5.30 (s, 2H), 4.41 (q, J=7.2 Hz, 2H), 1.37 (t, J=7.2 Hz, 3H).

(c) Ethyl 3-formylbenzo[b]thiophene-2-carboxylate (I36)

A mixture of ethyl 3-(bromomethyl)benzo[b]thiophene-2-carboxylate (I35) (5 g, 16.7 mmol) and NMO (7.83 g, 66.8 mmol) in THF (100 mL) was heated at reflux under N$_2$ overnight. The mixture was concentrated under reduced pressure and the residue was purified by silica gel chromatography (Pet. Ether/EtOAc=100:1 to 50:1) to give title compound (2.0 g, 50%) as a yellow solid. LCMS-B (ES-API): rt 4.18 min; m/z 235.0 [M+H]$^+$. $^1$H NMR (400 MHz, DMSO-d$_6$) δ 10.7 (s, 1H), 8.63-8.57 (m, 1H), 8.21-8.15 (m, 1H), 7.67-7.57 (m, 2H), 4.44 (q, J=7.1 Hz, 2H), 1.38 (t, J=7.1 Hz, 3H).

(ix) Ethyl 7-fluoro-3-formyl-4-methoxybenzo[b]thiophene-2-carboxylate (I40)

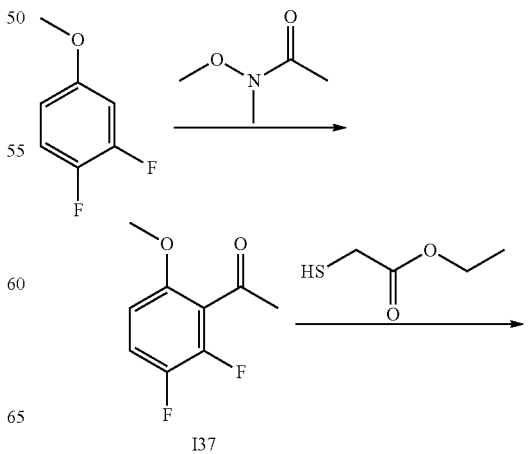

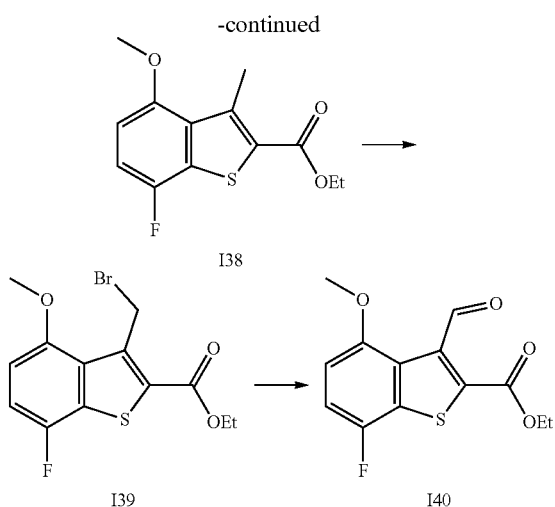

(a) 1-(2,3-Difluoro-6-methoxyphenyl)ethan-1-one (I37)

To a solution of 1,2-difluoro-4-methoxybenzene (10.0 g, 69.4 mmol) in THF (300 mL) at −78° C. was added n-BuLi (2.5 M solution in hexanes, 30.5 mL, 76.3 mmol) dropwise and the mixture was stirred at −78° C. for 40 min. A solution of N-methoxy-N-methylacetamide (11.3 g, 69.4 mmol) in THF (50 mL) was then added dropwise at −78° C. and the mixture was stirred at −78° C. for a further 1 h. The reaction was quenched with a saturated aqueous NH$_4$Cl solution, diluted with water (300 mL) and extracted with EtOAc (500 mL×3). The combined organic extracts were washed with brine, dried over Na$_2$SO$_4$, filtered and concentrated under reduced pressure. The residue was purified by silica gel chromatography (Pet. Ether/EtOAc=50:1 to 10:1) to give the title compound (2.1 g, 16%) as a yellow oil. LCMS-B (ES-API): rt 3.56 min, m/z 187.0 [M+H]$^+$. $^1$H NMR (400 MHz, CDCl$_3$) δ 7.17-7.10 (m, 1H), 6.63-6.60 (m, 1H), 3.82 (s, 3H), 2.54 (d, J=0.8 Hz, 3H).

(b) Ethyl 7-fluoro-4-methoxy-3-methylbenzo[b]thiophene-2-carboxylate (I38)

A mixture of 1-(2,3-difluoro-6-methoxyphenyl)ethan-1-one (I37) (1.88 g, 10.1 mmol), ethyl 2-mercaptoacetate (1.21 g, 10.1 mmol) and K$_2$CO$_3$ (1.39 g, 10.1 mmol) in DMF (75 mL) was heated at 75° C. under N$_2$ overnight. The mixture was poured into water, extracted with EtOAc and the combined organic extracts were washed with brine, dried over Na$_2$SO$_4$, filtered and concentrated under reduced pressure. The residue was purified by silica gel chromatography (Pet. Ether/EtOAc=500:1 to 100:1) to give the title compound (2.19 g, 81%) as white solid. LCMS-B (ES-API): rt 3.56 min, m/z 291.2 [M+Na]$^+$. $^1$H NMR (400 MHz, DMSO-d$_6$) δ 7.34 (t, J=9.0 Hz, 1H), 6.93 (dd, J=8.8, 3.8 Hz, 1H), 4.33 (q, J=7.1 Hz, 2H), 3.91 (s, 3H), 2.90 (s, 3H). 1.34 (t, J=7.1 Hz, 3H).

(c) Ethyl 3-(bromomethyl)-7-fluoro-4-methoxy-benzo[b]thiophene-2-carboxylate (I39)

To a solution of ethyl 7-fluoro-4-methoxy-3-methylbenzo[b]thiophene-2-carboxylate (I38) (1.7 g, 6.21 mmol) in CCl$_4$ (75 mL) was added NBS (1.2 g, 6.69 mmol) and AIBN (500 mg, 3.11 mmol) and the mixture was heated at 80° C. under N$_2$ overnight. The mixture was diluted with water (70 mL), extracted with EtOAc (70 mL×3) and the combined organic extracts were washed with brine, dried over Na$_2$SO$_4$, filtered and concentrated under reduced pressure.

The residue was purified by silica gel chromatography (Pet. Ether/EtOAc=500:1 to 150:1) to give the title compound (1.85 g, 84%) as a white solid. $^1$H NMR (400 MHz, DMSO-d$_6$) δ 7.53-7.30 (m, 2H), 5.39 (s, 2H), 4.41-4.36 (m, 2H), 3.97 (s, 3H), 1.37-1.33 (m, 3H).

(d) Ethyl 7-fluoro-3-formyl-4-methoxybenzo[b]thiophene-2-carboxylate (I40)

To a solution of ethyl 3-(bromomethyl)-7-fluoro-4-methoxybenzo[b]thiophene-2-carboxylate (I39) (1.8 g, 0.005 mol) in THF (25.0 mL) was added NMO (2.5 g, 0.02 mol) and the mixture was heated at reflux under N$_2$ overnight. The mixture was diluted with water (60 mL), extracted with EtOAc (60 mL×3) and the combined organic extracts were washed brine, dried over Na$_2$SO$_4$, filtered and concentrated under reduced pressure. The residue was purified by silica gel chromatography (Pet. Ether/EtOAc=500:1 to 40:1) to give the title compound (810 mg, 54%) as a white solid. LCMS-B (ES-API): rt 3.33 min, m/z 283.0 [M+H]$^+$. $^1$H NMR (400 MHz, DMSO-d$_6$) δ 10.5 (s, 1H), 7.47 (dd, J=9.5, 8.7 Hz, 1H), 7.05 (dd, J=8.8, 3.6 Hz, 1H), 4.34 (q, J=7.1 Hz, 2H), 3.89 (s, 3H), 1.31 (t, J=7.1 Hz, 3H).

(x) Ethyl 4-cyano-3-formylbenzo[b]thiophene-2-carboxylate (I44)

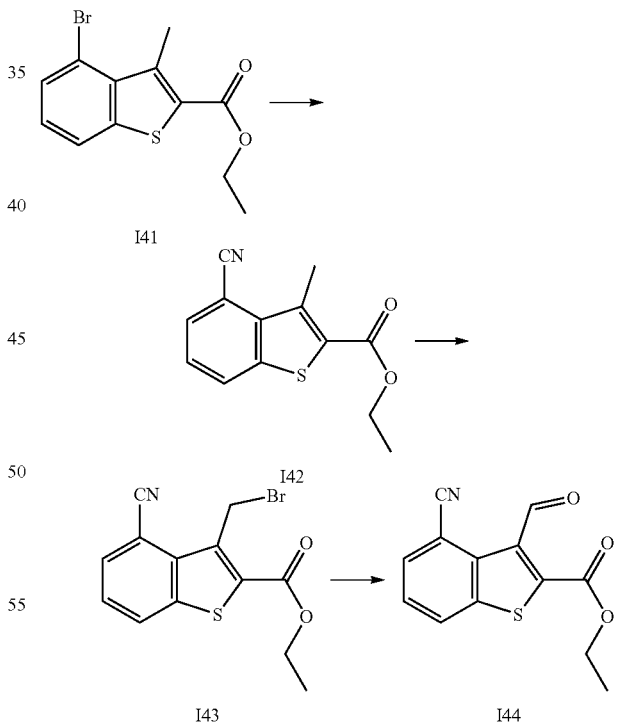

Compound I41 is compound I61 of WO 2019/219820.

(a) Ethyl 4-cyano-3-methylbenzo[b]thiophene-2-carboxylate (I42)

To a solution of ethyl 4-bromo-3-methylbenzo[b]thiophene-2-carboxylate (I41) (1.2 g, 4.01 mmol) in DMF (40 mL) was added CuCN (717 mg, 8.02 mmol) and Pd[PPh$_3$]$_4$ (463 mg, 0.40 mmol) and the mixture was heated at 120° C. under N$_2$ overnight. The mixture was filtered and the filtrate was diluted with water and extracted with EtOAc. The combined organic extracts were washed with brine, dried over Na$_2$SO$_4$, filtered and concentrated under reduced pressure. The residue was purified by silica gel chromatography (Pet. Ether/EtOAc=100:1 to 80:1) to give the title compound (600 mg, 60%) as a white solid. LCMS-B (ES-API): rt 4.27 min, m/z 246.1 [M+H]$^+$. $^1$H NMR (400 MHz, DMSO-d$_6$) δ 8.40 (d, J=8.2 Hz, 1H), 8.02 (d, J=7.3 Hz, 1H), 7.68 (t, J=8.0 Hz, 1H), 4.36 (q, J=7.1 Hz, 2H), 2.99 (s, 3H), 1.34 (t, J=7.1 Hz, 3H).

(b) Ethyl 3-(bromomethyl)-4-cyanobenzo[b]thiophene-2-carboxylate (I43)

A mixture of ethyl 4-cyano-3-methylbenzo[b]thiophene-2-carboxylate (I42) (450 mg, 1.83 mmol), NBS (392 mg, 2.20 mmol) and BPO (44 mg, 0.18 mmol) in CCl$_4$ (20 mL) was heated at reflux under N$_2$ for 16 h. The mixture was concentrated under reduced pressure and the residue was purified by silica gel chromatography (Pet. Ether/EtOAc=100:1 to 20:1) to give the title compound (360 mg, 60%) as a white solid. $^1$H NMR (400 MHz, DMSO-d$_6$) 8.52 (dd, J=8.3, 0.9 Hz, 1H), 8.14 (dd, J=7.4, 0.9 Hz, 1H), 7.77 (dd, J=8.1, 7.6 Hz, 1H), 5.49 (s, 2H), 4.43 (q, J=7.1 Hz, 2H), 1.37 (t, J=7.1 Hz, 3H).

(c) Ethyl 4-cyano-3-formylbenzo[b]thiophene-2-carboxylate (I44)

A solution of ethyl 3-(bromomethyl)-4-cyanobenzo[b]thiophene-2-carboxylate (I43) (450 mg, 1.39 mmol) and NMO (651 mg, 5.56 mmol) in THF (15 mL) was heated at reflux under N$_2$ for 16 h. The solvent was removed under reduced pressure and the residue was purified by silica gel chromatography (Pet. Ether/EtOAc=100:1 to 50:1) to give the title compound (180 mg, 50%) as a white solid. LCMS-A (ES-API): rt 1.56 min, m/z 260.0 [M+H]$^+$. $^1$H NMR (400 MHz, DMSO-d$_6$) δ 10.7 (s, 1H), 8.57 (dd, J=8.3, 0.8 Hz, 1H), 8.13 (dd, J=7.4, 0.8 Hz, 1H), 7.78 (t, J=8.0 Hz, 1H), 4.44 (q, J=7.1 Hz, 2H), 1.36 (t, J=7.1 Hz, 3H).

(xi) Ethyl 3-formyl-4-(trifluoromethyl)benzo[b]thiophene-2-carboxylate (I47)

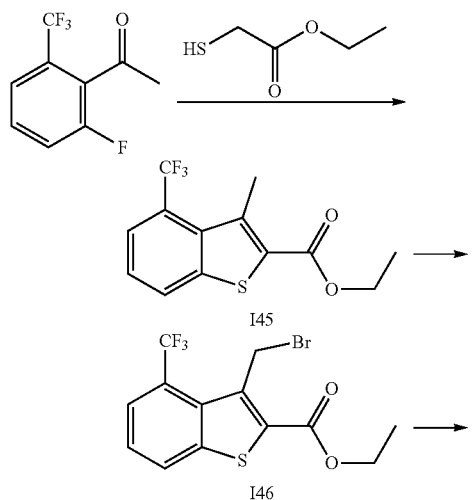

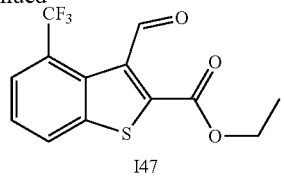

(a) Ethyl 3-methyl-4-(trifluoromethyl)benzo[b]thiophene-2-carboxylate (I45)

A mixture of 1-(2-fluoro-6-(trifluoromethyl)phenyl)ethan-1-one (2.0 g, 0.01 mol), ethyl 2-mercaptoacetate (1.44 g, 0.012 mol) and K$_2$CO$_3$ (4.15 g, 0.03 mol) in DMF (40 mL) was heated at 100° C. under N$_2$ overnight. The mixture was diluted with water (50 mL), extracted with EtOAc (50 mL×3) and the combined organic extracts were washed with water and brine then concentrated under reduced pressure. The residue was purified by silica gel chromatography (Pet. Ether/EtOAc=120:1 to 100:1) to give the title compound (2.4 g, 86%) as a white solid. LCMS-B (ES-API): rt 4.6 min, m/z 289.6 [M+H]$^+$. $^1$H NMR (400 MHz, DMSO-d$_6$) δ 8.40 (d, J=8.1 Hz, 1H), 7.94 (d, J=7.5 Hz, 1H), 7.68 (t, J=7.8 Hz, 1H), 4.36 (q, J=7.1 Hz, 2H), 2.83 (d, J=2.0 Hz, 3H), 1.34 (t, J=7.1 Hz, 3H).

(b) Ethyl 3-(bromomethyl)-4-(trifluoromethyl)benzo[b]thiophene-2-carboxylate (I46)

A mixture of ethyl 3-methyl-4-(trifluoromethyl)benzo[b]thiophene-2-carboxylate (I45) (1.2 g, 4.2 mmol), NBS (0.78 g, 4.4 mmol) and AIBN (65.7 mg, 0.4 mmol) in CCl$_4$ (20 mL) was heated at reflux under N$_2$ for 3 h. More NBS (0.28 g, 1.6 mmol) was added and the mixture was heated at reflux for a further 2 h. More NBS (0.28 g, 1.6 mmol) was added and the mixture was heated at reflux overnight. The mixture was diluted with water (20 mL), extracted with EtOAc (30 mL×3) and the combined organic extracts were washed with water, dried over Na$_2$SO$_4$, filtered and concentrated under reduced pressure. The residue was purified by silica gel chromatography (Pet. Ether/EtOAc=100:1) to give the title compound (1.17 g, 80%) as a white solid. $^1$H NMR (400 MHz, DMSO-d$_6$) δ 8.47 (d, J=8.1 Hz, 1H), 8.02 (d, J=7.5 Hz, 1H), 7.74 (t, J=7.9 Hz, 1H), 5.33 (s, 2H), 4.16 (q, J=7.1 Hz, 2H), 1.37 (t, J=7.1 Hz, 3H).

(c) Ethyl 3-formyl-4-(trifluoromethyl)benzo[b]thiophene-2-carboxylate (I47)

A solution of ethyl 3-(bromomethyl)-4-(trifluoromethyl)benzo[b]thiophene-2-carboxylate (I46) (1.5 g, 4.1 mmol) and NMO (2.06 g, 17.6 mmol) in THF (20 mL) was heated at reflux under N$_2$ overnight. Water (40 mL) was added and the mixture was extracted with EtOAc (40 mL×3). The combined organic extracts were washed with brine, dried over Na$_2$SO$_4$, filtered and concentrated under reduced pressure. The residue was purified by silica gel chromatography (Pet. Ether/EtOAc=100:1 to 70:1) to give the title compound (560 mg, 45%) as a white solid. LCMS-B (ES-API): rt 4.20 min, m/z 303.0 [M+H]$^+$. $^1$H NMR (400 MHz, DMSO-d$_6$) δ 10.5 (d, J=2.1 Hz, 1H), 8.55 (d, J=8.3 Hz, 1H), 8.01 (d, J=7.5 Hz, 1H), 7.80 (t, J=7.9 Hz, 1H), 4.39 (q, J=7.1 Hz, 2H), 1.33 (t, J=7.1 Hz, 3H).

(xii) Ethyl 4-bromo-7-fluoro-3-formylbenzo[b]thiophene-2-carboxylate (I49)

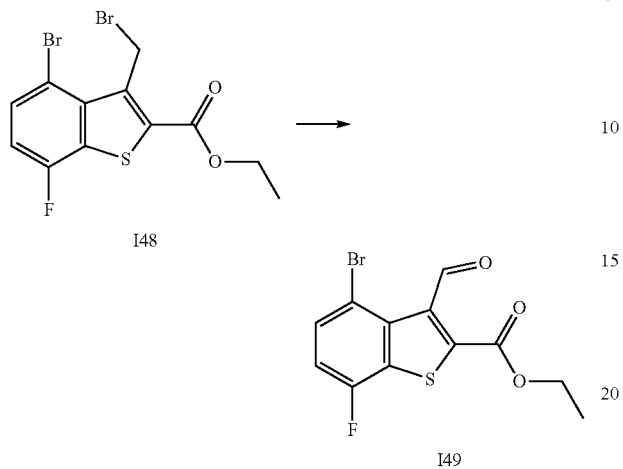

Compound I48 is compound I52 of WO 2019/219820.

A solution of ethyl 4-bromo-3-(bromomethyl)-7-fluorobenzo[b]thiophene-2-carboxylate (I48) (676 mg, 1.71 mmol) and NMO (800 mg, 6.84 mmol) in THF (5 mL) was heated at reflux under $N_2$ for 16 h. The mixture was partitioned between water (30 mL) and EtOAc (30 mL), the layers were separated and the aqueous layer was further extracted with EtOAc (30 mL×3). The combined organic extracts were washed with brine, dried over $Na_2SO_4$, filtered and concentrated under reduced pressure. The residue was purified by silica gel chromatography (Pet. Ether/EtOAc=100:1 to 30:1) to give the title compound (243 mg, 43%) as a white solid. $^1$H NMR (400 MHz, DMSO-$d_6$) δ 10.8 (s, 1H), 7.85 (dd, J=8.4, 4.4 Hz, 1H), 7.52 (t, J=9.2 Hz, 1H), 4.39 (q, J=7.2 Hz, 2H), 1.33 (t, J=7.2 Hz, 3H).

(xiii) Ethyl 4-bromo-3-formylbenzo[b]thiophene-2-carboxylate (I51)

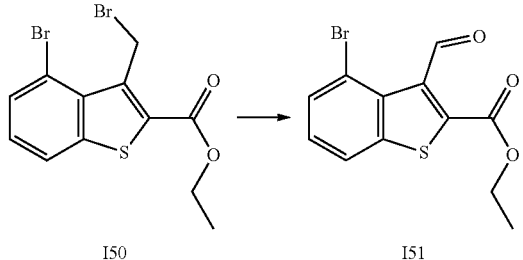 [SMILES: "I50" ; "I51" ; CCOC(=O)c1sc2cccc(Br)c2c1CBr ; CCOC(=O)c1sc2cccc(Br)c2c1C=O]

Compound I50 is compound I62 of WO 2019/219820.

A solution of ethyl 4-bromo-3-(bromomethyl)benzo[b]thiophene-2-carboxylate (I50) (100 mg, 2.64 mmol) and NMO (124 mg, 10.6 mmol) in THF (20 mL) was heated at reflux under $N_2$ overnight. The mixture was partitioned between water and EtOAc, the layers were separated and the aqueous layer was further extracted with EtOAc. The combined organic extracts were washed with brine, dried over $Na_2SO_4$, filtered and concentrated under reduced pressure. The residue was purified by silica gel chromatography (Pet. Ether/EtOAc=200:1 to 50:1) to give the title compound (290 mg, 35%) as a white solid. LCMS-B (ES-API): rt 3.33 min; m/z 312.9 [M+H]$^+$.

(xiv) Ethyl 3-formyl-4-methylbenzo[b]thiophene-2-carboxylate (I52)

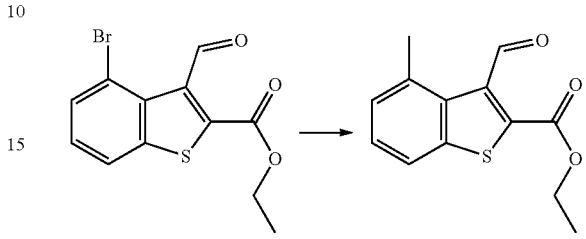

A mixture of ethyl 4-bromo-3-formylbenzo[b]thiophene-2-carboxylate (I51) (225 mg, 0.78 mmol), 2,4,6-trimethyl-1,3,5,2,4,6-trioxatriborinane (361 mg, 2.87 mmol), $K_2CO_3$ (397 mg, 2.87 mmol) and Pd(PPh$_3$)$_4$ (125 mg, 0.11 mmol) in dioxane (10 mL) was heated at reflux overnight under $N_2$. Water (50 mL) was added and the mixture was extracted with EtOAc (50 mL×3). The combined organic extracts were washed with water, brine, dried over $Na_2SO_4$, filtered, concentrated under reduced pressure. The residue was purified by silica gel chromatography (Pet. Ether/EtOAc=100:1 to 50:1) to give the title compound (50 mg, 28%) as a white solid. LCMS-B (ES-API): rt 4.26 min, m/z 249.1 [M+H]$^+$.

(xv) Ethyl 4-ethoxy-3-formylbenzo[b]thiophene-2-carboxylate (I54)

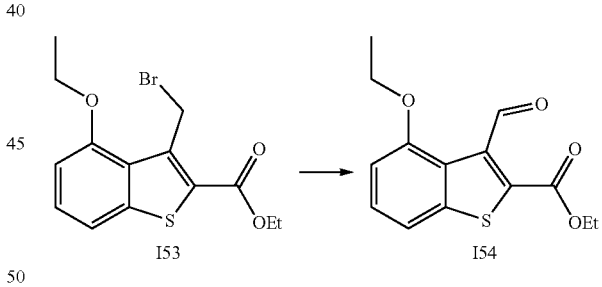

Compound I53 is compound I40 of WO 2019/219820.

A solution of ethyl 3-(bromomethyl)-4-ethoxybenzo[b]thiophene-2-carboxylate (I53) (2.0 g 6.00 mmol) and NMO (4.7 g, 24.0 mmol) in THF (100 mL) was heated at reflux overnight. The mixture was diluted with water, extracted with EtOAc and the combined organic extracts were washed with brine, dried over $Na_2SO_4$, filtered and concentrated under reduced pressure. The residue was purified by silica gel chromatography (Pet. Ether) to give the title compound (600 mg, 37%) as a gray solid. $^1$H NMR (400 MHz, DMSO-$d_6$) δ 10.6 (s, 1H), 7.65 (d, J=8.1 Hz, 1H), 7.52 (t, J=8.0 Hz, 1H), 7.02 (d, J=7.9 Hz, 1H), 4.32 (q, J=7.1 Hz, 2H), 4.17 (q, J=6.9 Hz, 2H), 1.36 (t, J=6.9 Hz, 3H), 1.29 (t, J=7.1 Hz, 3H).

(xvi) Ethyl 3-formyl-4-methoxythieno[3,2-c]pyridine-2-carboxylate (I56)

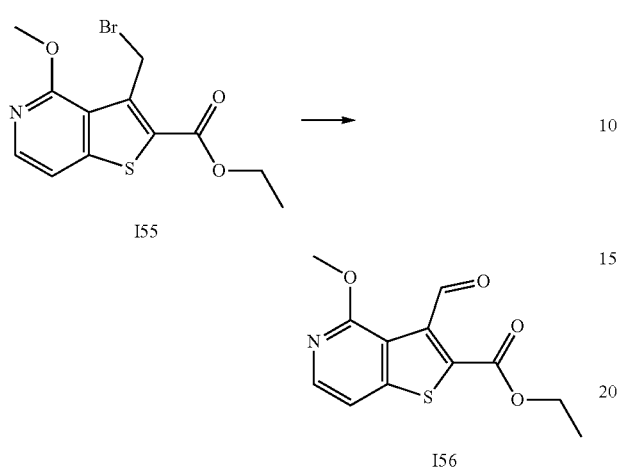

Compound I55 is compound I29 of WO 2019/219820.

A mixture of ethyl 3-(bromomethyl)-4-methoxythieno[3,2-c]pyridine-2-carboxylate (I55) (1 g, 3.03 mmol) and NMO (2.15 g, 12.2 mmol) in THF (20 mL) was heated at reflux overnight. Water (100 mL) was added and the mixture was extracted with EtOAc (50 mL×3). The combined organic extracts were washed with water (100 mL×2), brine (100 mL×2), dried over Na$_2$SO$_4$, filtered and concentrated under reduced pressure. The residue was purified by silica gel chromatography (Pet. Ether/EtOAc=50:1 to 5:1) to give the title compound (260 mg, 32%) as a yellow solid. LCMS-B (ES-API): rt 3.87 min; m/z 266.0 [M+H]$^+$.

EXAMPLES 3,3'-(Ethane-1,2-diylbis(5-carbamoyl-1H-benzo[d]imidazole-1,2-diyl))bis(4-chlorobenzo[b]thiophene-2-carboxylic acid) (1.1 and 1.2)

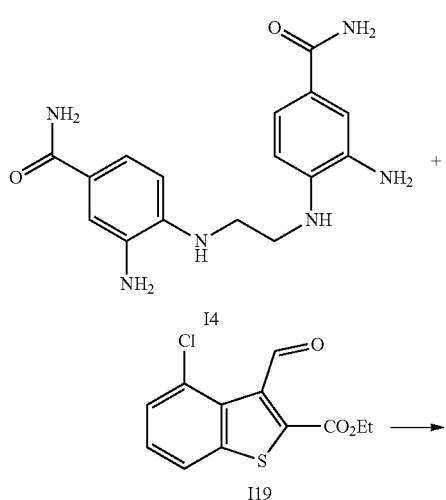

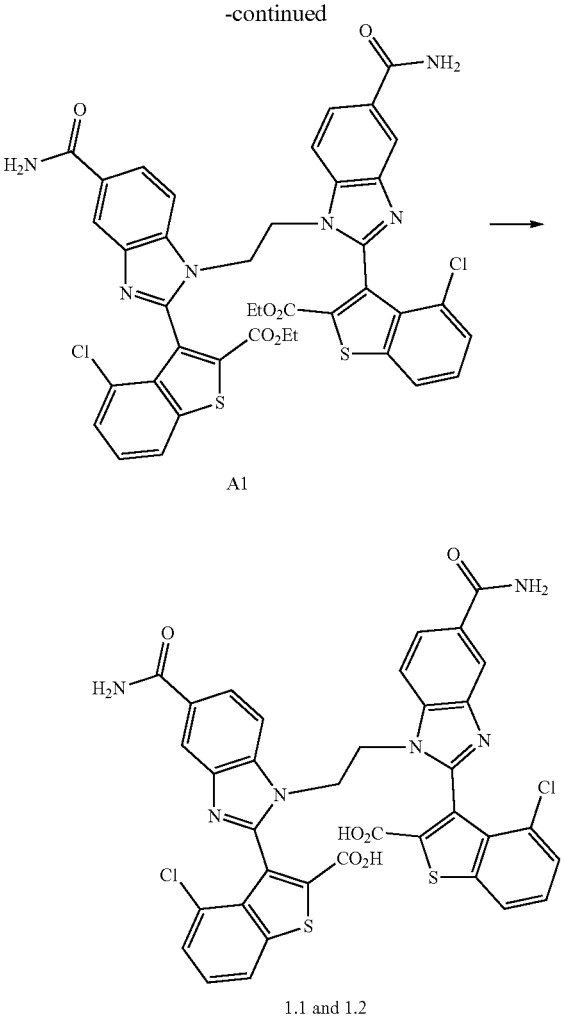

(a) Diethyl 3,3'-(ethane-1,2-diylbis(5-carbamoyl-1H-benzo[d]imidazole-1,2-diyl))bis(4-chlorobenzo[b]thiophene-2-carboxylate) (A1)

To a solution of 4,4'-(ethane-1,2-diylbis(azanediyl))bis(3-aminobenzamide) (I4) (20 mg, 0.061 mmol) in EtOH (3 mL) was added ethyl 4-chloro-3-formylbenzo[b]thiophene-2-carboxylate (I19) (33 mg, 0.12 mmol) and AcOH (0.3 mL) and the mixture was stirred at room temperature overnight. The mixture was diluted with EtOAc, washed with a saturated aqueous NaHCO$_3$ solution, brine, dried over Na$_2$SO$_4$, filtered and concentrated under reduced pressure. The residue was purified by prep. HPLC (Agilent 10 prep-C18, 10 μm, 250×21.2 mm column, eluting with a gradient of ACN in water with 0.1% TFA, at a flow rate of 20 mL/min) to give the title compound A1 (5 mg, 10%) as a yellow solid (mixture of atropisomeric diastereomers: $^1$H NMR showed a 1:1 mixture of racemate:meso). LCMS-B: rt 3.43 min; m/z 825.1/827.1 [M+H]$^+$. $^1$H NMR (400 MHz, MeOD) δ 8.29 (s, 2H), 8.14 (dd, J=8.3, 0.8 Hz, 1H), 8.12-8.05 (m, 2H), 8.04-7.91 (m, 3H), 7.63 (t, J=8.0 Hz, 1H), 7.54-7.48 (m, 2H), 7.23 (d, J=7.2 Hz, 1H), 4.77-4.67 (m, 2H), 4.53-4.40 (m, 2H), 4.17-4.09 (m, 2H), 3.85-3.71 (m, 2H), 1.08 (t, J=7.2 Hz, 3H), 0.91 (t, J=7.2 Hz, 3H).

(b) 3,3'-(Ethane-1,2-diylbis(5-carbamoyl-1H-benzo[d]imidazole-1,2-diyl))bis(4-chlorobenzo[b]thiophene-2-carboxylic acid) (1.1 and 1.2)

To a solution of diethyl 3,3'-(ethane-1,2-diylbis(5-carbamoyl-1H-benzo[d]imidazole-1,2-diyl))bis(4-chlorobenzo[b]thiophene-2-carboxylate) (A1) (150 mg, 0.18 mmol) in EtOH (10 mL) was added a solution of NaOH (43 mg, 1.08 mmol) in water (2 mL) and the mixture was stirred at room temperature overnight. The mixture was concentrated under reduced pressure and the residue was diluted with water, acidified to pH 3-4 with a 1 M aqueous HCl solution and the resulting precipitate was collected by filtration. The solid was purified by prep. HPLC (Agilent 10 prep-C18, 10 μm, 250×21.2 mm column, eluting with a gradient of ACN in water with 0.1% TFA, at a flow rate of 20 mL/min) to give separated atropisomers of the title compound 1.1 (peak 1: 20 mg, 14%) and title compound 1.2 (peak 2: 15 mg, 11%) as yellow solids.

Peak 1 (1.1) (prep HPLC: rt 13.27 min): LCMS-B: rt 2.81 min; m/z 769.0/771.0 [M+H]$^+$. $^1$H NMR (400 MHz, MeOD) δ 8.30 (d, J=1.2 Hz, 2H), 8.11 (dd, J=8.3, 0.8 Hz, 2H), 8.02 (dd, J=8.7, 1.6 Hz, 2H), 7.87 (d, J=8.8 Hz, 2H), 7.62 (t, J=8.0 Hz, 2H), 7.49 (dd, J=7.7, 0.8 Hz, 2H), 4.70-4.67 (m, 2H), 4.60-4.57 (m, 2H).

Peak 2 (1.2) (prep HPLC: rt 15.45 min): LCMS-B: rt 2.94 min; m/z 769.0/771.0 [M+H]$^+$. $^1$H NMR (400 MHz, MeOD) δ 8.29 (d, J=1.2 Hz, 2H), 8.11 (dd, J=8.8, 0.8 Hz, 2H), 8.02 (d, J=8.4 Hz, 2H), 7.92 (d, J=8.4 Hz, 2H), 7.51 (t, J=8.0 Hz, 2H), 7.22 (d, J=7.6 Hz, 2H), 4.78-4.76 (m, 2H), 4.52-4.50 (m, 2H).

3,3'-(Ethane-1,2-diylbis(5-carbamoyl-1H-benzo[d]imidazole-1,2-diyl))bis(4-chloro-7-fluorobenzo[b]thiophene-2-carboxylic acid) (2.1 and 2.2)

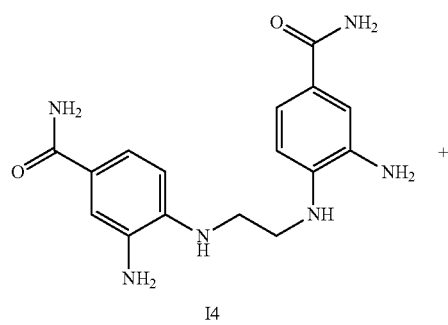

(a) Diethyl 3,3'-(ethane-1,2-diylbis(5-carbamoyl-1H-benzo[d]imidazole-1,2-diyl))bis(4-chloro-7-fluorobenzo[b]thiophene-2-carboxylate) (A2)

To a solution of ethyl 4-chloro-7-fluoro-3-formylbenzo[b]thiophene-2-carboxylate (I24) (250 mg, 0.87 mmol) in DMF (10 mL) was added 4,4'-(ethane-1,2-diylbis(azanediyl))bis(3-aminobenzamide) (I4) (143 mg, 0.44 mmol) and NaHSO$_3$ (90 mg, 0.87 mmol) and the mixture was heated at 120° C. under N$_2$ overnight. The mixture was partitioned between EtOAc and water, the layers were separated and the organic layer was washed with brine, dried over Na$_2$SO$_4$, filtered and concentrated under reduced pressure. The residue was purified by silica gel chromatography (Pet. Ether/EtOAc=10:1 to 1:1 to DCM/MeOH=10:1) to give the title compound A2 (90 mg, 24%) as a grey solid (mixture of atropisomeric diastereomers): $^1$H NMR showed a 1:1 mixture of racemate:meso). LCMS-B: rt 3.55 min; m/z 861.0 [M+H]$^+$. $^1$H NMR (400 MHz, DMSO-d$_6$) δ 8.23 (s, 2H), 8.09-7.96 (m, 6H), 7.70-7.58 (m, 2H), 7.50 (t, J=8.9 Hz, 1H), 7.39-7.29 (m, 3H), 4.54-4.32 (m, 4H), 4.08 (q, J=7.1 Hz, 2H), 3.84 (q, J=7.1 Hz, 2H), 0.96 (t, J=7.1 Hz, 3H), 0.85 (t, J=7.1 Hz, 3H).

(b) 3,3'-(Ethane-1,2-diylbis(5-carbamoyl-1H-benzo[d]imidazole-1,2-diyl))bis(4-chloro-7-fluorobenzo[b]thiophene-2-carboxylic acid) (2.1 and 2.2)

To a solution of diethyl 3,3'-(ethane-1,2-diylbis(5-carbamoyl-1H-benzo[d]imidazole-1,2-diyl))bis(4-chloro-7-fluorobenzo[b]thiophene-2-carboxylate) (A2) (80 mg, 0.09 mmol) in EtOH/water (3 mL/3 mL) was added NaOH (11 mg, 0.28 mmol) and the mixture was stirred at room temperature overnight. Most of the EtOH was removed under reduced pressure and the aqueous residue was acidified to pH 5 with a 1 M aqueous HCl solution. The resulting precipitate was collected by filtration and purified by preparative HPLC (Varian-940LC, prep-C18, 5 μm, 150×20 mm column, eluting with a gradient of ACN in water with 0.1% formic acid, at a flow rate of 15 mL/min) to give separated atropisomers of the title compound 2.1 (peak 1: 5 mg, 7%) and title compound 2.2 (peak 2: 5 mg, 7%) as white solids.

Peak 1 (2.1) (HPLC: rt 6.78 min): LCMS-B: rt 2.87 min; m/z 805.0 [M+H]$^+$. $^1$H NMR (400 MHz, DMSO-d$_6$) δ 8.21 (s, 2H), 8.02 (s, 2H), 7.93 (d, J=8.5 Hz, 2H), 7.85 (br s, 2H), 7.59-7.47 (m, 4H), 7.30 (s, 2H), 4.52-4.41 (m, 2H), 4.41-4.29 (m, 2H).

Peak 2 (2.2) (HPLC: rt 8.00 min): LCMS-B: rt 2.97 min; m/z 804.9 [M+H]$^+$. $^1$H NMR (400 MHz, DMSO-d$_6$) δ 8.21 (s, 2H), 8.03 (s, 2H), 8.00-7.93 (m, 2H), 7.81 (br s, 2H), 7.44-7.35 (m, 2H), 7.33-7.25 (m, 4H), 4.62-4.53 (m, 2H), 4.31-4.11 (m, 2H).

3,3'-(Butane-1,4-diylbis(5-carbamoyl-1H-benzo[d]imidazole-1,2-diyl))bis(4 chlorobenzo[b]thiophene-2-carboxylic acid) (3)

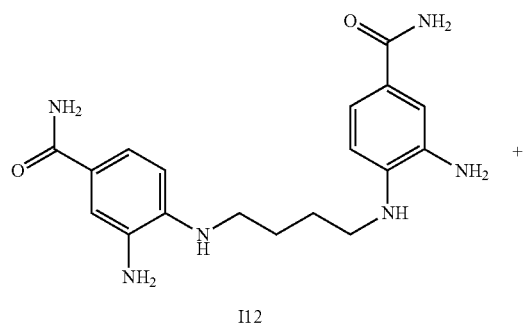

I12

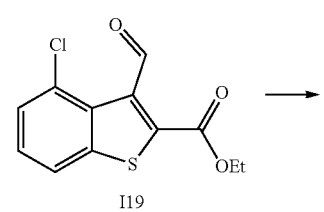

I19

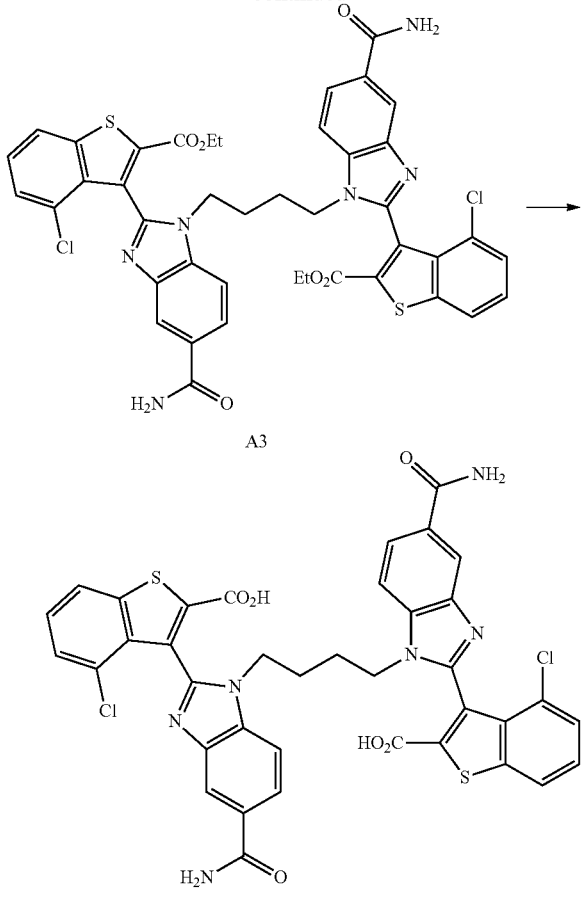

A3

3

(a) Diethyl 3,3'-(butane-1,4-diylbis(5-carbamoyl-1H-benzo[d]imidazole-1,2-diyl))bis(4-chlorobenzo[b]thiophene-2-carboxylate) (A3)

A mixture of 4,4'-(butane-1,4-diylbis(azanediyl))bis(3-aminobenzamide) (I12) (100 mg, 0.28 mmol), ethyl 4-chloro-3-formylbenzo[b]thiophene-2-carboxylate (I19) (151 mg, 0.56 mmol) and NaHSO$_3$ (59 mg, 0.56 mmol) in DMF (8 mL) was heated at 80° C. under nitrogen for 16 h. The mixture was partitioned between water (50 mL) and EtOAc (50 mL), the layers were separated and the aqueous layer extracted with EtOAc (50 mL×3). The combined organic layers were washed with brine (50 mL), dried over Na$_2$SO$_4$, filtered and concentrated under reduced pressure. The residue was purified by silica gel chromatography (DCM/MeOH=100:1 to 10:1) to give title compound A3 (130 mg, 54%) as a black solid (mixture of atropisomeric diastereomers: analytical HPLC analysis (Agilent 1200 series, Waters Nova-pak, 3.9×150 mm, 4 μm C18 column, eluting with a gradient of MeOH in water with 0.05% TFA, at a flow rate of 0.5 mL/min) showed a 1:1 mixture of components with rt 11.59 min and 11.80 min.). LCMS-B: rt 3.57 min; m/z 853.1/855.1. The mixture was used in the next step without further purification.

(b) 3,3'-(Butane-1,4-diylbis(5-carbamoyl-1H-benzo[d]imidazole-1,2-diyl))bis(4-chlorobenzo[b]thiophene-2-carboxylic acid) (3)

A solution of diethyl 3,3'-(butane-1,4-diylbis(5-carbamoyl-1H-benzo[d]imidazole-1,2-diyl))bis(4-chlorobenzo[b]

thiophene-2-carboxylate) (A3) (80 mg, 0.09 mmol) and NaOH (23 mg, 0.54 mmol) in EtOH/water (6 mL/2 mL) was stirred at room temperature for 16 h. The solvent was removed under reduced pressure and the residue was diluted with water and acidified to pH 4-5 with a 2 M aqueous HCl solution. The resulting precipitate was collected by filtration and purified by prep HPLC (Agilent 10 Prep-C18, 250×21.2 mm column, eluting with a gradient of ACN in water with 0.1% TFA, at a flow rate of 20 mL/min) to give separated atropisomers of the title compound 3 (peak 1: 5 mg, 6%) and (peak 2: 10 mg, impure) as gray solids.

Peak 1: (3) (prep HPLC: rt 11.34 min): LCMS-B: rt 2.81 min; m/z 797.0/799.0 [M+H]$^+$. $^1$H NMR (400 MHz, DMSO-d$_6$) δ 8.17 (s, 4H), 8.01 (s, 2H), 7.84 (s, 2H), 7.66-7.46 (m, 4H), 7.36-7.16 (m, 4H), 4.01-3.75 (m, 4H), 1.56-1.41 (m, 4H).

Peak 2: (prep HPLC: rt 14.51 min): LCMS-B: rt 2.90 min; m/z 797.1/799.1 [M+H]$^+$.

3,3'-(Propane-1,3-diylbis(5-carbamoyl-1H-benzo[d]imidazole-1,2-diyl))bis(4-chlorobenzo[b]thiophene-2-carboxylic acid) (4.1 and 4.2)

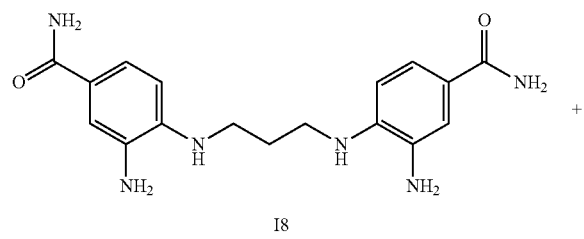

I8

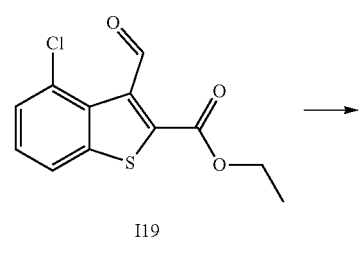

I19

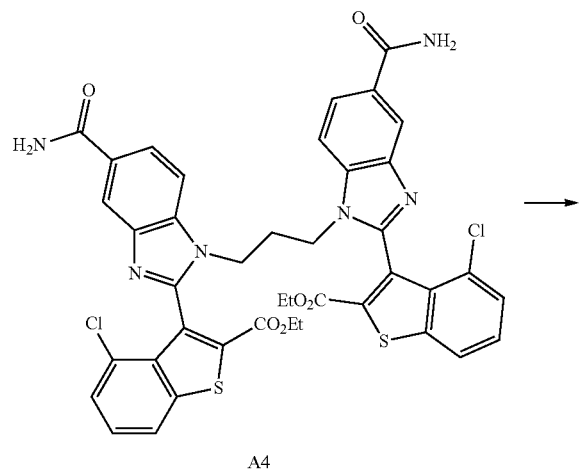

A4

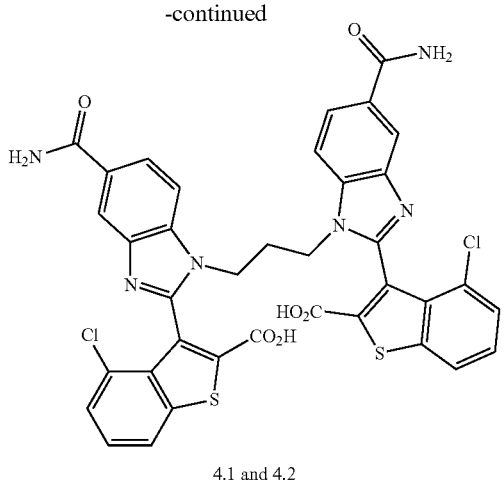

4.1 and 4.2

(a) Diethyl 3,3'-(propane-1,3-diylbis(5-carbamoyl-1H-benzo[d]imidazole-1,2-diyl))bis(4-chlorobenzo[b]thiophene-2-carboxylate) (A4)

To a solution of 4,4'-(propane-1,3-diylbis(azanediyl))bis(3-aminobenzamide) (I8) (200 mg, 0.58 mmol) in DMF (15 mL) was added ethyl 4-chloro-3-formylbenzo[b]thiophene-2-carboxylate (I19) (314 mg, 1.17 mmol) and NaHSO$_3$ (122 mg, 1.17 mmol) and the mixture was heated at 80° C. under nitrogen overnight. Water was added and the mixture was extracted with EtOAc (100 mL×3). The combined organic extracts were washed with water, brine, dried over Na$_2$SO$_4$, filtered and concentrated under reduced pressure. The residue was purified by silica gel chromatography (Pet. Ether/EtOAc=10:1 to DCM/MeOH=15:1) to give the title compound A4 (155 mg, 32%) as a gray solid (mixture of atropisomeric diastereomers: $^1$H NMR showed a 1:1 mixture of racemate:meso). LCMS-B: rt 3.48 min; m/z 839.1. $^1$H NMR (400 MHz, DMSO-d$_6$) δ 8.28-8.15 (m, 4H), 8.05-7.99 (m, 2H), 7.84-7.75 (m, 2H), 7.65-7.40 (m, 6H), 7.32-7.26 (m, 2H), 4.10-3.94 (m, 8H), 2.30-2.04 (m, 2H), 0.81 (t, J=7.2 Hz, 3H), 0.77 (t, J=7.2 Hz, 3H).

(b) 3,3'-(Propane-1,3-diylbis(5-carbamoyl-1H-benzo[d]imidazole-1,2-diyl))bis(4-chlorobenzo[b]thiophene-2-carboxylic acid) (4.1 and 4.2)

To a solution of diethyl 3,3'-(propane-1,3-diylbis(5-carbamoyl-1H-benzo[d]imidazole-1,2-diyl))bis(4-chlorobenzo[b]thiophene-2-carboxylate) (A4) (80 mg, 0.095 mmol) in EtOH/water (4 mL/2 mL) was added NaOH (23 mg, 0.57 mmol) and the mixture was stirred at room temperature overnight. The solvent was removed under reduced pressure and the residue was diluted with water and acidified to pH 4-5 with a 2 M aqueous HCl solution. The resulting precipitate was collected by filtration and purified by preparative HPLC (Agilent 10 Prep-C18, 250×21.2 mm column, eluting with a gradient of ACN in water with 0.1% TFA, at a flow rate of 20 mL/min) to give separated atropisomers of the title compound 4.1 (peak 1: 5 mg, 6%) and title compound 4.2 (peak 2: 6 mg, 7%) as white solids.

Peak 1 (4.1) (HPLC: rt 9.10 min): LCMS-B: rt 2.82 min; m/z 783.0 [M+H]$^+$. $^1$H NMR (400 MHz, DMSO-d$_6$) δ 8.27-8.17 (m, 4H), 8.01 (br s, 2H), 7.78 (d, J=8.5 Hz, 2H), 7.59 (t, J=7.9 Hz, 2H), 7.50-7.40 (m, 4H), 7.31 (br s, 2H), 4.09-4.06 (m, 4H), 2.26-2.03 (m, 2H).

Peak 2 (4.2) (HPLC: rt 11.50 min): LCMS-B: rt 2.90 min; m/z 783.0 [M+H]$^+$. $^1$H NMR (400 MHz, DMSO-d$_6$) δ 8.24-8.16 (m, 4H), 8.00 (br s, 2H), 7.82 (d, J=8.3 Hz, 2H), 7.64-7.47 (m, 4H), 7.38 (d, J=7.7 Hz, 2H), 7.29 (br s, 2H), 4.18-3.95 (m, 4H), 2.21-2.08 (m, 2H).

3,3'-(Ethane-1,2-diylbis(5-carbamoyl-1H-benzo[d]imidazole-1,2-diyl))bis(4-methoxybenzo[b]thiophene-2-carboxylic acid) (5.2)

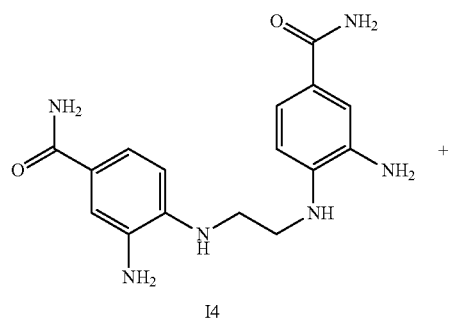

I4

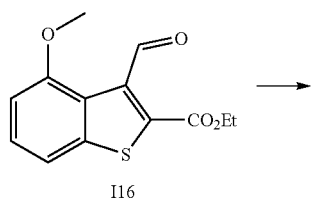

I16

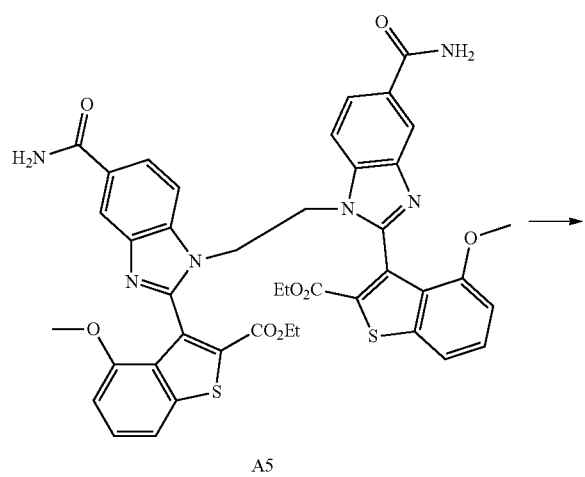

A5

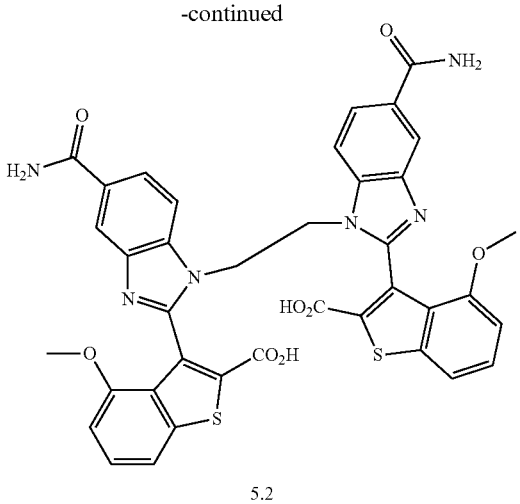

5.2

(a) Diethyl 3,3'-(ethane-1,2-diylbis(5-carbamoyl-1H-benzo[d]imidazole-1,2-diyl))bis(4-methoxy-benzo[b]thiophene-2-carboxylate) (A5)

A mixture of ethyl 3-formyl-4-methoxybenzo[b]thiophene-2-carboxylate (I16) (270 mg, 1.02 mmol), 4,4'-(ethane-1,2-diylbis(azanediyl))bis(3-aminobenzamide) (I4) (167 mg, 0.51 mmol) and NaHSO$_3$ (53 mg, 0.51 mmol) in DMF (25 mL) was heated at 120° C. under nitrogen overnight. The mixture was cooled to room temperature, poured into water (50 mL) and extracted with EtOAc (50 mL). The organic extract was washed with water, brine, dried over Na$_2$SO$_4$, filtered and concentrated under reduced pressure. The residue was purified by silica gel chromatography (DCM/MeOH=100:1 to 10:1) to give the title compound A5 (112 mg, 13%) as a white solid (mixture of atropisomeric diastereomers: $^1$H NMR showed a 3:1 mixture). The material was used in the next step without further purification. LCMS-B: rt 3.45 min; m/z 817.3. $^1$H NMR (400 MHz, DMSO-d$_6$) δ 8.18 (br s, 2H), 8.10-7.92 (m, 4H), 7.90-7.80 (m, 1H), 7.78-7.68 (m, 2H), 7.66-7.42 (m, 3H), 7.28 (br s, 2H), 6.87 (d, J=7.8 Hz, 1.5H), 6.58 (d, J=7.6 Hz, 0.5H), 4.59-4.36 (m, 3H), 4.26-4.06 (m, 3H), 4.01-3.91 (m, 1H), 3.67-3.59 (m, 1H), 3.30 (s, 4.5H, coincident with water peak), 3.18 (s, 1.5H), 0.86 (t, J=7.6 Hz, 1.5H), 0.67 (t, J=7.6 Hz, 4.5H).

(b) 3,3'-(Ethane-1,2-diylbis(5-carbamoyl-1H-benzo[d]imidazole-1,2-diyl))bis(4-methoxybenzo[b]thiophene-2-carboxylic acid) (5.2)

To a solution of diethyl 3,3'-(ethane-1,2-diylbis(5-carbamoyl-1H-benzo[d]imidazole-1,2-diyl))bis(4-methoxy-benzo[b]thiophene-2-carboxylate) (A5) (83 mg, 0.1 mmol) in EtOH/water (5:1, 10 mL) was added NaOH (40 mg, 1.0 mmol) and the mixture was stirred at room temperature overnight. The mixture was acidified to pH 6 with a 1 M aqueous HCl solution then concentrated under reduced pressure. The residue purified by preparative HPLC (Agilent PrepStar 218, prep-C18, 10 μm, 250×2.12 mm column, eluting with a gradient of MeOH in water with 0.1% TFA, at a flow rate of 20 mL/min) to give the title compound 5.2 (10 mg, 13%) as a white solid. Only one component was isolated from the reaction mixture of unknown stereochemistry.

LCMS-B: rt 2.85 min; m/z 761.1. $^1$H NMR (400 MHz, DMSO-$d_6$) δ 8.18 (s, 2H), 7.99 (br s, 2H), 7.83 (d, J=8.4 Hz, 2H), 7.70 (d, J=8.0 Hz, 2H), 7.57 (t, J=8.0 Hz, 2H), 7.35 (d, J=8.5 Hz, 2H), 7.27 (br s, 2H), 6.86 (d, J=8.0 Hz, 2H), 4.32-4.15 (m, 4H), 3.36 (s, 6H).

3,3'-(Ethane-1,2-diylbis(5-carbamoyl-1H-benzo[d]imidazole-1,2-diyl))bis(4-methoxybenzo[b]thiophene-2-carboxylic acid) (5.1 and 5.2)

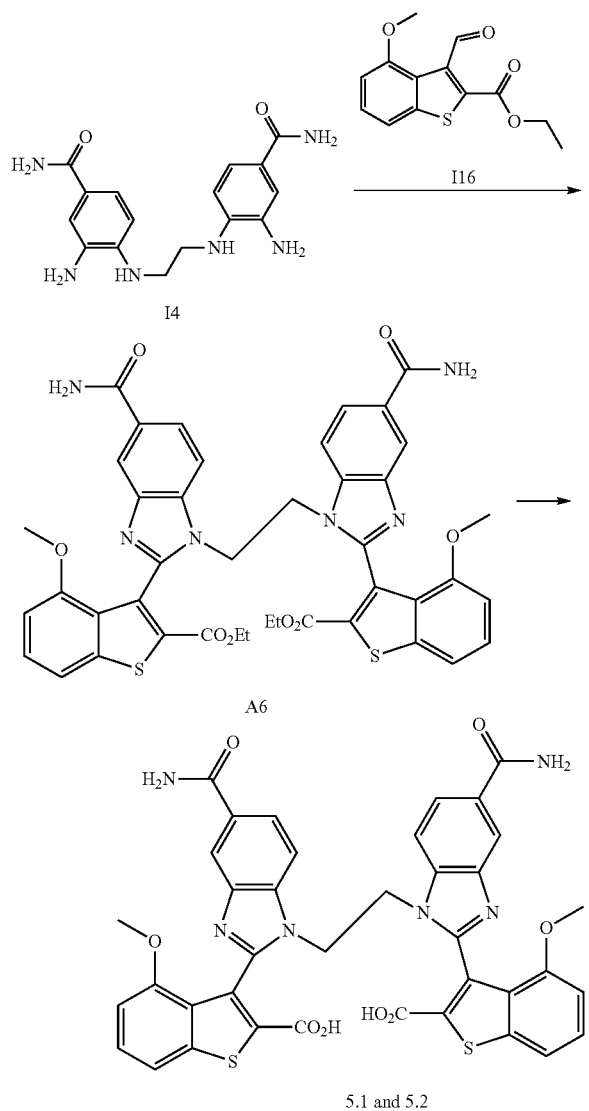

(a) Diethyl 3,3'-(ethane-1,2-diylbis(5-carbamoyl-1H-benzo[d]imidazole-1,2-diyl))bis(4-methoxybenzo[b]thiophene-2-carboxylate) (A6)

A solution of ethyl 3-formyl-4-methoxybenzo[b]thiophene-2-carboxylate (I16) (400 mg, 1.52 mmol), 3,3'-(ethane-1,2-diylbis(azanediyl))bis(4-aminobenzamide) (I4) (250 mg, 0.76 mmol) and NaHSO$_3$ (78.1 mg, 0.76 mmol) in DMF (15 mL) was heated at 120° C. under N$_2$ overnight. Water (50 mL) was added and the mixture was extracted with dichloromethane (50 mL×3). The combined organic extracts were washed with brine, dried over Na$_2$SO$_4$, filtered and concentrated under reduced pressure to give the title compound (450 mg, 36%) as a brown solid. LCMS-B (ES-API): rt 3.12 min, m/z 817.6 [M+H]$^+$ (b) 3,3'-(Ethane-1,2-diylbis(5-carbamoyl-1H-benzo[d]imidazole-1,2-diyl))bis(4-methoxybenzo[b]thiophene-2-carboxylic acid) (5.1 and 5.2)

To a solution of diethyl 3,3'-(ethane-1,2-diylbis(5-carbamoyl-1H-benzo[d]imidazole-1,2-diyl))bis(4-methoxybenzo[b]thiophene-2-carboxylate) (A6) (430 mg, 0.53 mmol) in EtOH/H$_2$O (5:1, 10 mL) was added NaOH (212 mg, 5.3 mmol) and the mixture was stirred at room temperature overnight. Most of the EtOH was removed under reduced pressure and the aqueous residue was adjusted to pH 5 with 1 M aqueous HCl. The resulting precipitate was collected by filtration and purified by prep. HPLC (Agilent, BOSTON, 250×2.12 mm, 10 μm column, eluting with a gradient of ACN in water with 0.1% formic acid at a flow rate of 20.0 mL/min) to give separated atropisomers of the title compound (5.1) (peak 1: 11 mg, 3%) as a white solid and the title compound (5.2) (peak 2: 22 mg, 5%) as a brown solid.

Peak 1 (Prep HPLC, rt 7.53 min): (5.1); LCMS-B (ES-API): rt 2.57 min, m/z 761.1 [M+H]$^+$. $^1$H NMR (400 MHz, DMSO-$d_6$) δ 8.17 (s, 2H), 7.99 (br s, 2H), 7.87 (d, J=8.4 Hz, 2H), 7.63 (d, J=8.4 Hz, 2H), 7.46-7.43 (m, 4H), 7.27 (br s, 2H), 6.61 (d, J=8.0 Hz, 2H), 4.37-4.32 (m, 2H), 4.11-4.09 (m, 2H), 3.18 (s, 6H).

Peak 2 (Prep HPLC, rt 8.60 min): (5.2); LCMS-B (ES-API): rt 2.51 min, m/z 761.1 [M+H]$^+$;

$^1$H NMR (400 MHz, DMSO-$d_6$) δ 8.17 (s, 2H), 7.98 (br s, 2H), 7.80-7.73 (m, 2H), 7.69 (d, J=8.1 Hz, 2H), 7.54 (t, J=8.1 Hz, 2H), 7.35-7.11 (m, 4H), 6.85 (d, J=8.0 Hz, 2H), 4.23-4.20 (m, 2H), 4.14-4.12 (m, 2H), 3.34 (s, 6H).

Diethyl 3,3'-(ethane-1,2-diylbis(5-carbamoyl-1H-benzo[d]imidazole-1,2-diyl))bis(4-methoxythieno[3,2-c]pyridine-2-carboxylate) (6) and 3,3'-(ethane-1,2-diylbis(5-carbamoyl-1H-benzo[d]imidazole-1,2-diyl))bis(4-methoxythieno[3,2-c]pyridine-2-carboxylic acid) (7)

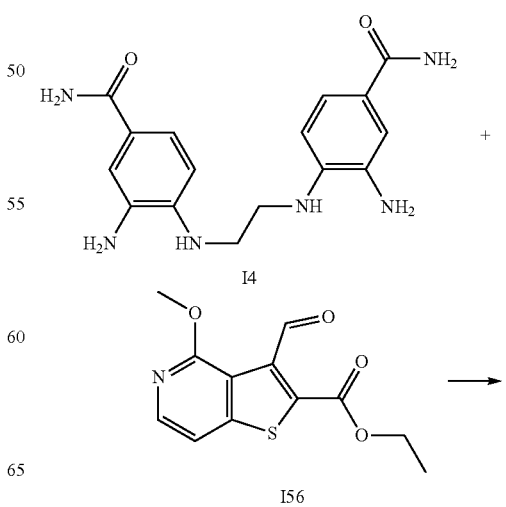

-continued

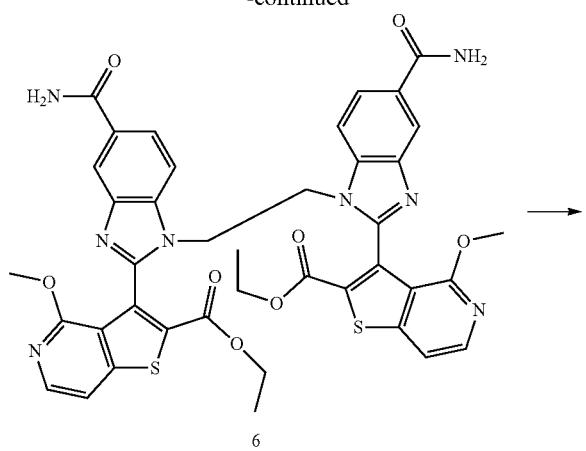

6

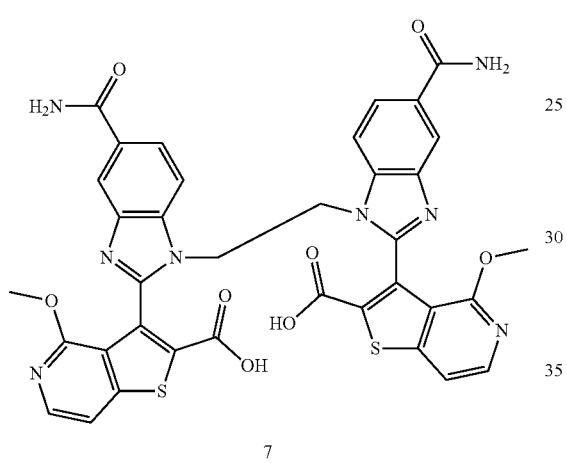

7

(a) Diethyl 3,3'-(ethane-1,2-diylbis(5-carbamoyl-1H-benzo[d]imidazole-1,2-diyl))bis(4-methoxythieno[3,2-c]pyridine-2-carboxylate) (6)

A solution of ethyl 3-formyl-4-methoxythieno[3,2-c]pyridine-2-carboxylate (I56) (162 mg, 0.61 mmol), 4,4'-(ethane-1,2-diylbis(azanediyl))bis(3-aminobenzamide) (I4) (100 mg, 0.305 mmol) and NaHSO$_3$ (64 mg, 0.61 mmol) in DMF (3 mL) was heated at 80° C. overnight. Water (30 mL) was added and the mixture was extracted with EtOAc (30 mL×3). The combined organic extracts were washed with water (30 mL×2), brine (30 mL×2), dried over Na$_2$SO$_4$, filtered and concentrated under reduced pressure. The residue was purified by prep. HPLC (Varian-940-LC, 150×20 mm, 5 µm column, eluting with a gradient of ACN in water with 0.1% formic acid at a flow rate of 15.0 mL/min) to give the title compound (6 mg, 2%) as a white solid. LCMS-B (ES-API): rt 3.08 min; m/z 819.2 [M+H]$^+$. $^1$H NMR (400 MHz, DMSO-d$_6$) δ 8.20 (s, 4H), 8.02-7.94 (m, 6H), 7.83 (d, J=5.2 Hz, 2H), 7.31 (br s, 2H), 4.54-4.48 (m, 2H), 4.20-4.13 (m, 2H), 3.79-3.73 (m, 2H), 3.65-1.66 (m, 2H), 3.54 (s, 6H), 0.77 (t, J=6.8 Hz, 6H).

(b) 3,3'-(Ethane-1,2-diylbis(5-carbamoyl-1H-benzo[d]imidazole-1,2-diyl))bis(4-methoxythieno[3,2-c]pyridine-2-carboxylic acid) (7)

To a solution of diethyl 3,3'-(ethane-1,2-diylbis(5-carbamoyl-1H-benzo[d]imidazole-1,2-diyl))bis(4-methoxythieno[3,2-c]pyridine-2-carboxylate) (6) (70 mg, 0.086 mmol) in EtOH/H$_2$O (2.0 mL/0.5 mL) was added NaOH (11 mg, 0.257 mmol) and the mixture was stirred at room temperature overnight. The mixture was diluted with water (5 mL) and most of the EtOH was removed under reduced pressure. The aqueous residue was adjusted to pH 4-5 with 2 M aqueous HCl and the resulting precipitate was collected by filtration and purified by prep-HPLC (Varian-940-LC, 150×20 mm, 5 µm column, eluting with a gradient of ACN in water with 0.1% formic acid at a flow rate of 15.0 mL/min) to give the title compound (4 mg, 6%) as a white solid. LCMS-B (ES-API): rt 2.53 min, m/z 761.0 [M−H]$^-$. $^1$H NMR (400 MHz, DMSO-d$_6$) δ 8.19 (s, 2H), 8.06 (d, J=5.6 Hz, 2H), 8.01 (br s, 2H), 7.94 (d, J=8.4 Hz, 2H), 7.74-7.66 (m, 4H), 7.28 (br s, 2H), 4.46-4.42 (m, 2H), 4.17-4.15 (m, 2H), 3.32 (s, 6H).

Diethyl 3,3'-(ethane-1,2-diylbis(5-carbamoyl-1H-benzo[d]imidazole-1,2-diyl))bis(benzo[b]thiophene-2-carboxylate) (8) and 3,3'-(Ethane-1,2-diylbis(5-carbamoyl-1H-benzo[d]imidazole-1,2-diyl))bis(benzo[b]thiophene-2-carboxylic acid) (9)

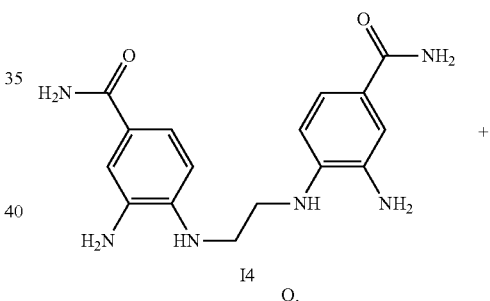

I4

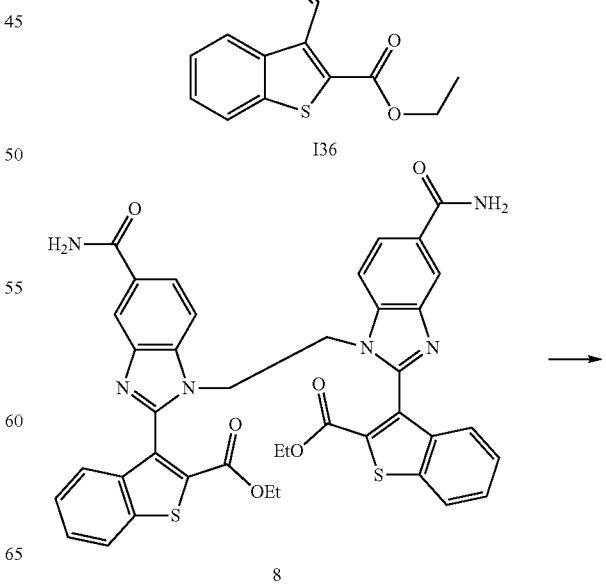

8

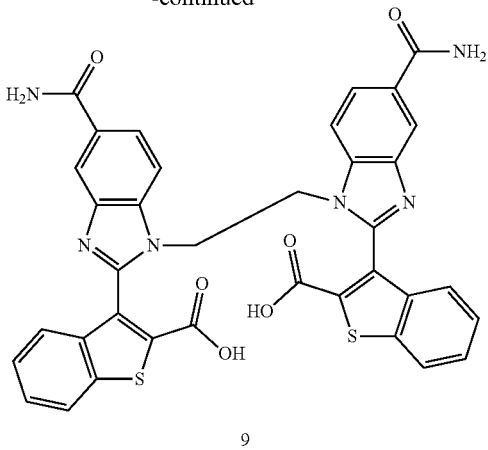

9

(a) Diethyl 3,3'-(ethane-1,2-diylbis(5-carbamoyl-1H-benzo[d]imidazole-1,2-diyl))bis(benzo[b]thiophene-2-carboxylate) (8)

A solution of ethyl 3-formylbenzo[b]thiophene-2-carboxylate (I36) (0.600 g, 2.57 mmol), 4,4'-(ethane-1,2-diylbis(azanediyl))bis(3-aminobenzamide) (I4) (0.423 g, 1.29 mmol) and $NaHSO_3$ (0.268 g, 2.57 mmol) in DMF (40 mL) was heated at 130° C. under $N_2$ for 48 h. Water was added and the mixture was extracted with EtOAc. The combined organic extracts were washed with brine, dried over $Na_2SO_4$, filtered and concentrated under reduced pressure. The residue was purified by silica gel chromatography (DCM/MeOH=80:1 to 40:1) to give the title compound (440 mg, 46%) as a brown solid (mixture of atropisomeric diastereomers: $^1$H NMR showed a 1:1 mixture of racemate:meso). LCMS-B (ES-API): rt 2.95 min; m/z 757.1 [M+H]$^+$. $^1$H NMR (400 MHz, DMSO-$d_6$) δ 8.23 (s, 1H), 8.17 (d, J=8.2 Hz, 1H), 8.04 (br s, 1H), 7.85-7.79 (m, 2H), 7.72 (d, J=8.2 Hz, 2H), 7.56 (t, J=7.6 Hz, 1H), 7.38-7.30 (m, 4H), 7.24 (t, J=7.6 Hz, 1H), 7.15-7.13 (m, 2H), 7.00-6.97 (m, 2H), 6.13 (d, J=8.2 Hz, 1H), 4.79-4.76 (m, 1H), 4.52-4.49 (m, 1H), 4.31-4.29 (m, 1H), 4.19-3.95 (m, 5H), 0.98 (t, J=7.2 Hz, 3H), 0.91 (t, J=7.2 Hz, 3H).

(b) 3,3'-(Ethane-1,2-diylbis(5-carbamoyl-1H-benzo[d]imidazole-1,2-diyl))bis(benzo[b]thiophene-2-carboxylic acid) (9)

To a solution of diethyl 3,3'-(ethane-1,2-diylbis(5-carbamoyl-1H-benzo[d]imidazole-1,2-diyl))bis(benzo[b]thiophene-2-carboxylate) (8) (0.200 g 0.26 mmol) in EtOH/$H_2O$ (20 mL/4 mL) was added NaOH (0.106 g 2.6 mmol) and the mixture was stirred at room temperature overnight. Most of the EtOH was removed under reduced pressure and the aqueous residue was acidified to pH 4-5 with 1 M aqueous HCl. The resulting precipitate was collected by filtration and purified by prep-HPLC (Shimadzu LC-8A, 150×20 mm, 10 μm column, eluting with a gradient of ACN in water with 0.1% TFA at a flow rate of 15.0 mL/min) to give the title compound (5 mg, 2%) as a white solid (mixture of atropisomeric diastereomers: $^1$H NMR showed a 1:1 mixture of racemate:meso). LCMS-C (ES-API): rt 3.14 min; m/z 701.2 [M+H]$^+$. $^1$H NMR (400 MHz, 60° C., DMSO-$d_6$) δ 8.23 (s, 1H), 8.15 (d, J=8.0 Hz, 1H), 7.85-7.82 (m, 3H), 7.73 (dd, J=8.4, 1.7 Hz, 1H), 7.56 (t, J=7.7 Hz, 1H), 7.38-7.36 (m, 3H), 7.23-7.18 (m, 3H), 7.13-7.05 (m, 3H), 6.90 (d, J=8.8 Hz, 1H), 6.28 (d, J=8.4 Hz, 1H), 4.73-4.70 (m, 1H), 4.67-4.34 (m, 2H), 4.17-4.14 (m, 1H).

Diethyl 3,3'-(ethane-1,2-diylbis(5-carbamoyl-1H-benzo[d]imidazole-1,2-diyl))bis(4-bromobenzo[b]thiophene-2-carboxylate) (10) and 3,3'-(Ethane-1,2-diylbis(5-carbamoyl-1H-benzo[d]imidazole-1,2-diyl))bis(4-bromobenzo[b]thiophene-2-carboxylic acid) (11.1 and 11.2)

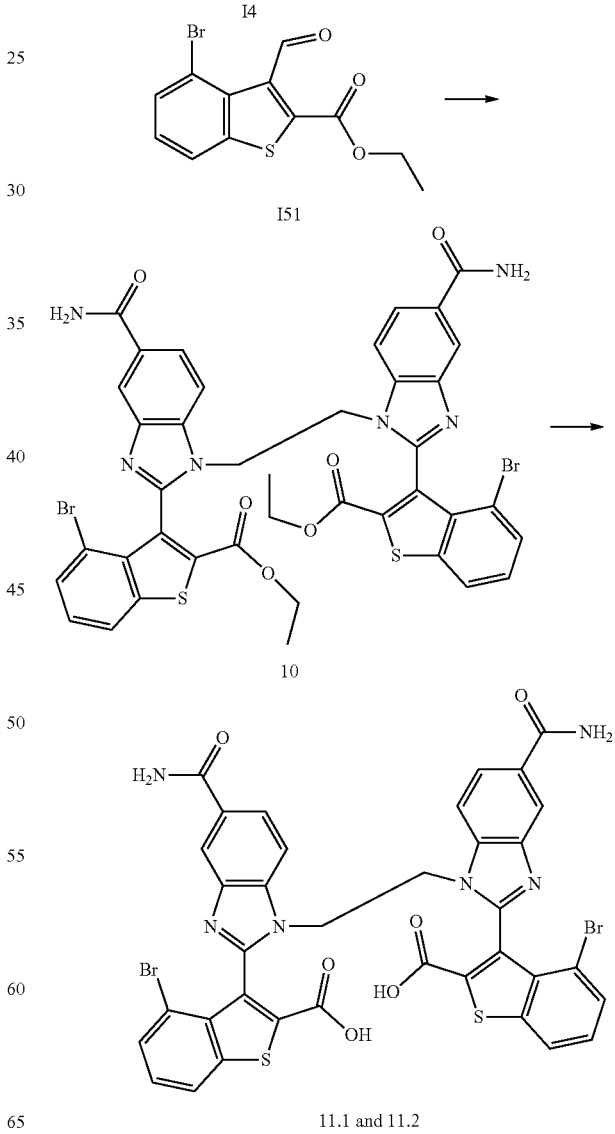

11.1 and 11.2

(a) Diethyl 3,3'-(ethane-1,2-diylbis(5-carbamoyl-1H-benzo[d]imidazole-1,2-diyl))bis(4-bromobenzo[b]thiophene-2-carboxylate) (10)

A solution of ethyl 4-bromo-3-formylbenzo[b]thiophene-2-carboxylate (I51) (0.300 g, 0.96 mmol), 4,4'-(ethane-1,2-diylbis(azanediyl))bis(3-aminobenzamide) (I4) (0.157 g, 0.48 mmol) and NaHSO$_4$ (0.199 g, 1.92 mmol) in DMF (15 mL) was heated at 80° C. under N$_2$ overnight. Additional NaHSO$_4$ (0.199 g, 1.92 mmol) was added and the mixture was heated at 100° C. overnight. The mixture was diluted with water, extracted with EtOAc (100 mL×3) and the combined organic extracts were washed with brine, dried over Na$_2$SO$_4$, filtered and concentrated under reduced pressure. The residue was purified by silica gel chromatography (DCM/MeOH=60:1 to 20:1) to give the title compound (180 mg, 21%) as a white solid (mixture of atropisomeric diastereomers: $^1$H NMR showed a 1:1 mixture of racemate:meso). LCMS-B (ES-API): rt 3.18 min; m/z 912.9, 914.8 [M+H]$^+$. $^1$H NMR (400 MHz, DMSO-d$_6$) δ 8.30 (dd, J=8.0, 0.8 Hz, 1H), 8.25-8.22 (m, 2H), 8.19-8.16 (m, 1H), 8.04-7.95 (m, 5H), 7.92-7.90 (m, 1H), 7.71 (dd, J=8.0, 0.8 Hz, 1H), 7.57 (t, J=8.0 Hz, 1H), 7.49-7.46 (m, 2H), 7.32 (br s, 2H), 4.63-4.57 (m, 1H), 4.50-4.46 (m, 1H), 4.38-4.34 (m, 1H), 4.28-4.21 (m, 1H), 4.05 (q, J=7.2 Hz, 2H), 3.65-3.57 (m, 2H), 0.94 (t, J=7.2 Hz, 3H), 0.78 (t, J=7.2 Hz, 3H).

(b) 3,3'-(Ethane-1,2-diylbis(5-carbamoyl-1H-benzo[d]imidazole-1,2-diyl))bis(4-bromobenzo[b]thiophene-2-carboxylic acid) (11.1. and 11.2)

To a solution of 3,3'-(ethane-1,2-diylbis(5-carbamoyl-1H-benzo[d]imidazole-1,2-diyl))bis(4-bromobenzo[b]thiophene-2-carboxylate) (10) (150 mg, 0.16 mmol) in EtOH/H$_2$O (10 mL/2 mL) was added NaOH (39 mg, 0.98 mmol) and the mixture was stirred at room temperature overnight. Most of the EtOH was removed under reduced pressure and the aqueous residue was adjusted to pH 4-5 with 1 M aqueous HCl. The resulting precipitate was collected by filtration and purified by prep. HPLC (Agilent 10 prep-C18, 10 μm, 250×21.2 mm column, eluting with a gradient of ACN in water with 0.1% TFA, at a flow rate of 20 mL/min) to give separated atropisomers of the title compound (11.1) (peak 1: 10 mg, 7%) and the title compound (11.2) (peak 2: 14 mg, 10%) as white solids.

Peak 1 (Prep HPLC, rt 8.99 min): (11.1); LCMS-B (ES-API): rt 0.56 min, m/z 856.9, 858.9 [M+H]$^+$; $^1$H NMR (400 MHz, DMSO-d$_6$) δ 8.21-8.19 (m, 6H), 7.97 (br s, 2H), 7.64 (d, J=8.0 Hz, 2H), 7.59-7.53 (m, 2H), 7.42-7.39 (m, 2H), 7.20 (br s, 2H), 4.35-4.33 (m, 2H), 4.27-4.24 (m, 2H).

Peak 2 (Prep HPLC, rt 12.15 min): (11.2); LCMS-B (ES-API): rt 0.67 min, m/z 856.9, 858.9 [M+H]$^+$; $^1$H NMR (400 MHz, DMSO-d$_6$) δ 8.23-8.16 (m, 6H), 8.01 (br s, 2H), 7.89-7.81 (m, 2H), 7.51 (d, J=8.0 Hz, 2H), 7.44-7.42 (m, 2H), 7.25 (br s, 2H), 4.57-4.50 (m, 2H), 4.19-4.07 (m, 2H).

Diethyl 3,3'-(ethane-1,2-diylbis(5-carbamoyl-1H-benzo[d]imidazole-1,2-diyl))bis(7-fluoro-4-methoxybenzo[b]thiophene-2-carboxylate) (12) and 3,3'-(Ethane-1,2-diylbis(5-carbamoyl-1H-benzo[d]imidazole-1,2-diyl))bis(7-fluoro-4-methoxybenzo[b]thiophene-2-carboxylic acid) (13.1 and 13.2)

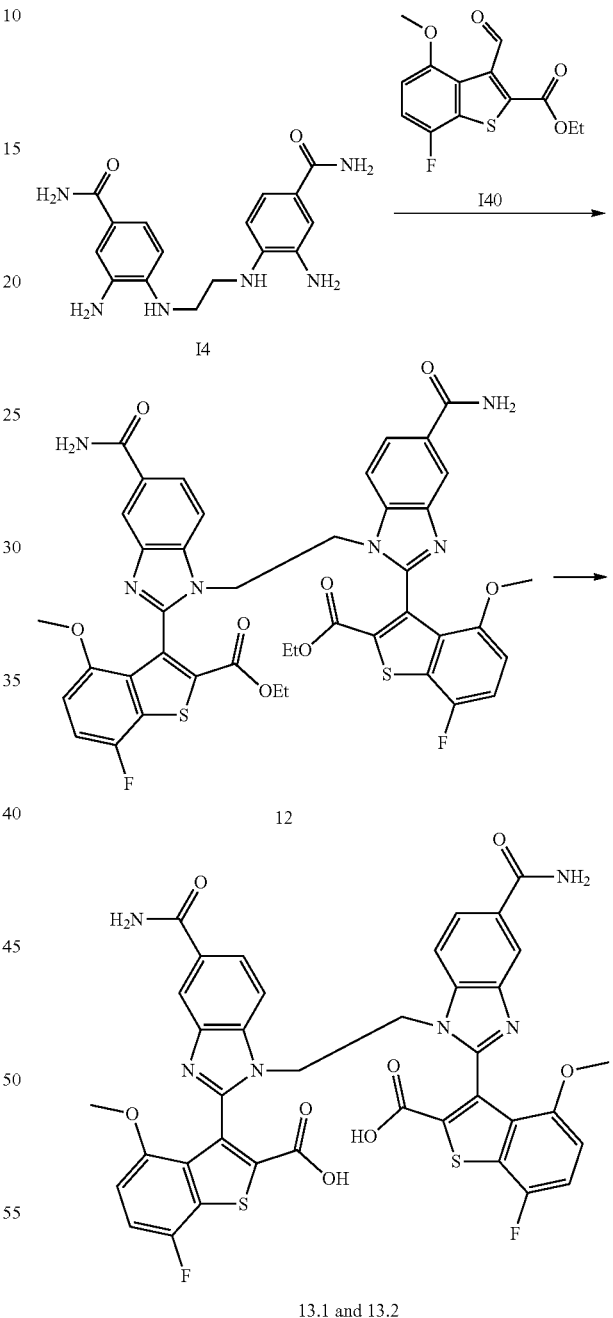

12

13.1 and 13.2

(a) Diethyl 3,3'-(ethane-1,2-diylbis(5-carbamoyl-1H-benzo[d]imidazole-1,2-diyl))bis(7-fluoro-4-methoxybenzo[b]thiophene-2-carboxylate) (12)

A solution of ethyl 7-fluoro-3-formyl-4-methoxybenzo[b]thiophene-2-carboxylate (I40) (158 mg, 0.56 mmol), 4,4'-

(ethane-1,2-diylbis(azanediyl))bis(3-aminobenzamide) (I4) (37 mg, 0.28 mmol) and NaHSO₃ (58 mg, 0.56 mmol) in DMF (3 mL) was heated at 100° C. under N₂ overnight. The mixture was poured into water (30 mL), extracted with EtOAc (30 mL×3) and the combined organic extracts were washed brine, dried over Na₂SO₄, filtered and concentrated under reduced pressure. The residue was purified by silica gel chromatography (Pet. Ether/EtOAc=40:1 to 20:1 and DCM/MeOH=10:1) to give the title compound (80 mg, 16%) as a yellow solid (mixture of atropisomeric diastereomers). LCMS-B (ES-API): rt 1.21 min, m/z 853.1 [M+H]⁺.

(b) 3,3'-(Ethane-1,2-diylbis(5-carbamoyl-1H-benzo [d]imidazole-1,2-diyl))bis(7-fluoro-4-methoxybenzo [b]thiophene-2-carboxylic acid) (13.1 and 13.2)

To a solution of diethyl 3,3'-(ethane-1,2-diylbis(5-carbamoyl-1H-benzo[d]imidazole-1,2-diyl))bis(7-fluoro-4-methoxybenzo[b]thiophene-2-carboxylate) (12) (25 mg, 0.03 mmol) in EtOH/H₂O (5 mL/1 mL) was added NaOH (7 mg, 0.18 mmol) and the mixture was stirred at room temperature overnight. Water (5 mL) was added and the mixture was washed with EtOAc (5 mL×3). The aqueous layer was acidified to pH 4-5 with 3 M aqueous HCl and the resulting precipitate was collected by filtration and purified by prep. HPLC (Shimadzu LC-20AP, BOSTON, 250×2.12 mm, 10 μm column, eluting with a gradient of ACN in water with 0.1% TFA at a flow rate of 20.0 mL/min) to give separated atropisomers of the title compound (13.1) (peak 1: 3.5 mg, 15%) and (13.2) (peak 2: 4 mg, 17%) as yellow solids.

Peak 1 (Prep HPLC, rt 12.70 min): (13.1); LCMS-B (ES-API): rt 0.56 min, m/z 797.1 [M+H]⁺;

¹H NMR (400 MHz, DMSO-d₆) δ 8.18 (s, 2H), 8.02 (br s, 2H), 7.97 (d, J=8.6 Hz, 2H), 7.82 (d, J=8.6 Hz, 2H), 7.43 (t, J=9.1 Hz, 2H), 7.29 (br s, 2H), 6.82 (dd, J=8.8, 3.1 Hz, 2H), 4.38-4.34 (m, 2H), 4.22-4.19 (m, 2H), 3.51 (s, 6H).

Peak 2 (Prep HPLC, rt 13.46 min): (13.2); LCMS-B (ES-API): rt 0.65 min, m/z 797.0 [M+H]⁺;

¹H NMR (400 MHz, DMSO-d₆) δ 8.19 (s, 2H), 8.06-7.97 (m, 4H), 7.89 (d, J=8.6 Hz, 2H), 7.31-7.25 (m, 4H), 6.55 (dd, J=8.8, 3.3 Hz, 2H), 4.44-4.39 (m, 2H), 4.21-4.16 (m, 2H), 3.19 (s, 6H).

Diethyl 3,3'-(1,1'-(ethane-1,2-diyl)bis(5-carbamoyl-1H-benzo[d]imidazole-2,1-diyl))bis(4-methylbenzo [b]thiophene-2-carboxylate) (14) and 3,3'-(Ethane-1,2-diylbis(5-carbamoyl-1H-benzo[d]imidazole-1,2-diyl))bis(4-methylbenzo[b]thiophene-2-carboxylic acid) (15.1 and 15.2)

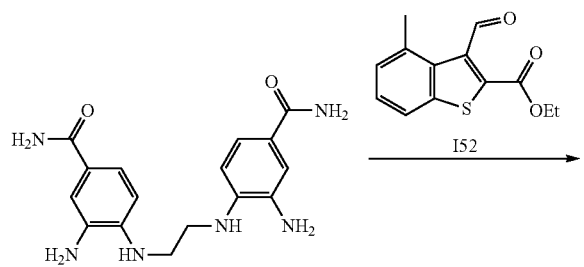

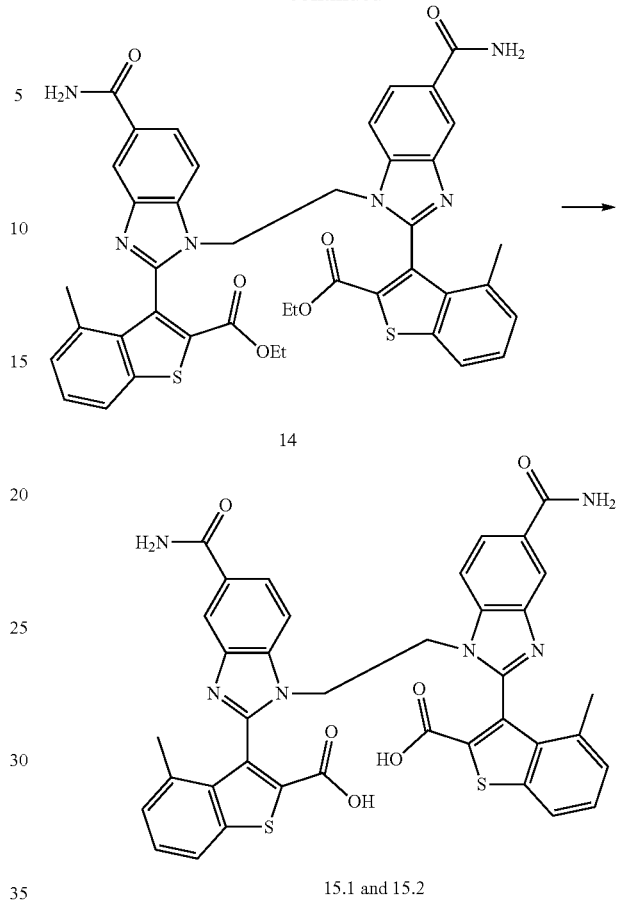

(a) Diethyl 3,3'-(1,1'-(ethane-1,2-diyl)bis(5-carbamoyl-1H-benzo[d]imidazole-2,1-diyl))bis(4-methylbenzo[b]thiophene-2-carboxylate) (14)

A solution of ethyl 3-formyl-4-methylbenzo[b]thiophene-2-carboxylate (I52) (50 mg, 0.75 mmol), 4,4'-(ethane-1,2-diylbis(azanediyl))bis(3-aminobenzamide) (I4) (23 mg, 0.07 mmol) and NaHSO₃ (14.6 mg, 0.14 mmol) in DMF (2 mL) was heated at 80° C. overnight under N₂. The mixture was diluted with water (10 mL), extracted with EtOAc (10 mL×3) and the combined organic extracts were washed with water, brine, dried over Na₂SO₄, filtered and concentrated under reduced pressure. The residue was purified by prep-TLC (DCM/MeOH=20/1) to give the title compound (20 mg, 13%) as a white solid (mixture of atropisomeric diastereomers in ~2:1 ratio). LCMS-B (ES-API): rt 3.32 min, m/z 785.2 [M+H]⁺. ¹H NMR (400 MHz, DMSO-d₆) δ 8.25-8.24 (m, 2H), 8.11-8.04 (m, 3H), 8.03-7.93 (m, 3H), 7.86 (d, J=8.5 Hz, 1.35H), 7.59 (d, J=8.6 Hz, 0.65H), 7.54-7.48 (m, 1.35H), 7.46-7.41 (m, 0.65H), 7.32 (br s, 2H), 7.21 (d, J=7.1 Hz, 1.35H), 7.02 (d, J=7.3 Hz, 0.65H), 4.78-4.69 (m, 1.35H), 4.59-4.54 (m, 0.65H), 4.15-3.96 (m, 4H), 3.51-3.40 (m, obscured by solvent), 1.70 (s, 4H), 1.54 (s, 2H), 0.90 (t, J=7.1 Hz, 2H), 0.73 (t, J=7.1 Hz, 4H).

(b) 3,3'-(Ethane-1,2-diylbis(5-carbamoyl-1H-benzo [d]imidazole-1,2-diyl))bis(4-methylbenzo[b]thiophene-2-carboxylic acid) (15.1 and 15.2)

To a solution of diethyl 3,3'-(ethane-1,2-diylbis(5-carbamoyl-1H-benzo[d]imidazole-1,2-diyl))bis(4-methylbenzo[b]thiophene-2-carboxylate) (14) (140 mg, 0.18 mmol) in EtOH (10 mL) and water (2 mL) was added NaOH (43 mg, 1.10 mmol) and the mixture was stirred at room temperature overnight. The mixture was concentrated under reduced pressure and the residue was diluted with water (3 mL) and adjusted to pH 4-5 with 1 M aqueous HCl. The resulting precipitate was collected by filtration and purified by prep. HPLC (Varian-940-LC, YMC-C18, 150×20 mm, 5 µm column, eluting with a gradient of ACN in water with 0.1% formic acid at a flow rate of 15.0 mL/min) to give separated atropisomers of the title compound (15.1) (peak 1: 9 mg, 7%) and (15.2) (peak 2: 12.7 mg, 10%) as white solids.

Peak 1 (Prep HPLC, rt 10.85 min): (15.1); LCMS-B (ES-API): rt 2.82 min, m/z 729.1 [M+H]$^+$;
$^1$H NMR (400 MHz, DMSO-d$_6$) δ 8.24 (d, J=1.7 Hz, 2H), 8.02 (br s, 2H), 7.97 (d, J=8.2 Hz, 2H), 7.87 (d, J=8.6 Hz, 2H), 7.46-7.39 (m, 2H), 7.36-7.26 (m, 4H), 7.05 (d, J=7.2 Hz, 2H), 4.57-4.49 (m, 2H), 3.99-3.95 (m, 2H), 1.56 (s, 6H).

Peak 2 (Prep HPLC, rt 12.01 min): (15.2); LCMS-B (ES-API): rt 2.80 min, m/z 729.1 [M+H]$^+$;
$^1$H NMR (400 MHz, DMSO-d$_6$) δ 8.24 (d, J=1.6 Hz, 2H), 8.07-7.96 (m, 6H), 7.72 (d, J=8.5 Hz, 2H), 7.48 (t, J=7.7 Hz, 2H), 7.28 (br s, 2H), 7.17 (d, J=7.3 Hz, 2H), 4.30-4.21 (m, 4H), 1.66 (s, 6H).

Diethyl 3,3'-(ethane-1,2-diylbis(5-carbamoyl-1H-benzo[d]imidazole-1,2-diyl))bis(4-cyanobenzo[b]thiophene-2-carboxylate) (16) and 3,3'-(Ethane-1,2-diylbis(5-carbamoyl-1H-benzo[d]imidazole-1,2-diyl))bis(4-cyanobenzo[b]thiophene-2-carboxylic acid) (17)

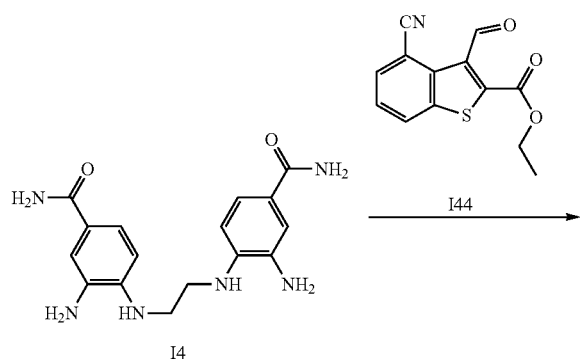

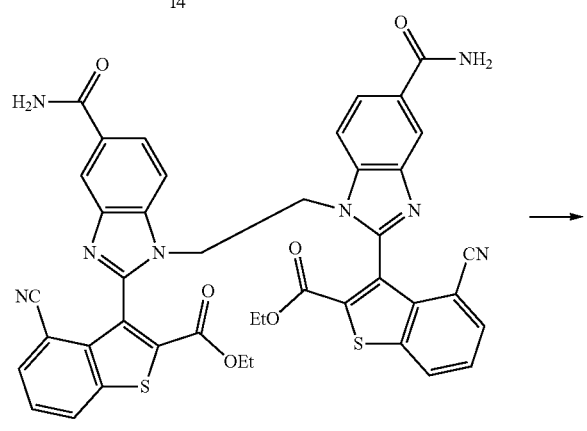

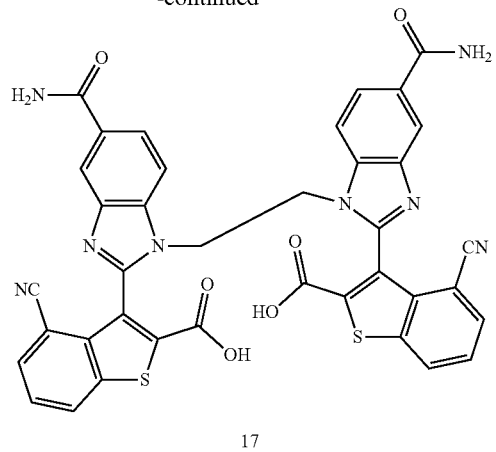

(a) Diethyl 3,3'-(ethane-1,2-diylbis(5-carbamoyl-1H-benzo[d]imidazole-1,2-diyl))bis(4-cyanobenzo[b]thiophene-2-carboxylate) (16)

A solution of 4,4'-(ethane-1,2-diylbis(azanediyl))bis(3-aminobenzamide) (I4) (139 mg, 0.42 mmol), ethyl 4-cyano-3-formylbenzo[b]thiophene-2-carboxylate (I44) (220 mg, 0.84 mmol) and NaHSO$_3$ (88 mg, 0.84 mmol) in DMF (15 mL) was heated at 120° C. under N$_2$ for 16 h. The mixture poured into water (80 mL), extracted with EtOAc (80 mL×3) and the combined organic extracts were washed water (80×2 mL), brine (80 mL), dried over Na$_2$SO$_4$, filtered and concentrated under reduced pressure. The residue was purified by silica gel chromatography (DCM/MeOH=1:0 to 20:1) to give the title compound (130 mg, 38%) as a brown solid (mixture of atropisomeric diastereomers: $^1$H NMR showed a 1:1 mixture of racemate:meso). LCMS-C (ES-API): rt 3.42 min, m/z 807.2 [M+H]$^+$. $^1$H NMR (400 MHz, DMSO-d$_6$) δ 8.58 (d, J=8.3 Hz, 1H), 8.54 (d, J=7.8 Hz, 1H), 8.24 (s, 2H), 8.06-8.00 (m, 7H), 7.83-7.72 (m, 3H), 7.34 (br s, 2H), 4.59-4.44 (m, 2H), 4.38-4.25 (m, 2H), 4.09 (q, J=7.0 Hz, 2H), 3.89 (q, J=7.0 Hz, 2H), 0.98 (t, J=7.1 Hz, 3H), 0.88 (t, J=7.1 Hz, 3H).

(b) 3,3'-(Ethane-1,2-diylbis(5-carbamoyl-1H-benzo[d]imidazole-1,2-diyl))bis(4-cyanobenzo[b]thiophene-2-carboxylic acid) (17)

To a solution of diethyl 3,3'-(ethane-1,2-diylbis(5-carbamoyl-1H-benzo[d]imidazole-1,2-diyl))bis(4-cyanobenzo[b]thiophene-2-carboxylate) (16) (125 mg, 0.15 mmol) in EtOH/water (5 mL/5 mL) was added NaOH (6 mg, 0.90 mmol) and the mixture was stirred at room temperature for 16 h. The mixture was concentrated under reduced pressure and the residue was diluted with water (5 mL) and adjusted to pH 4-5 with 2 M aqueous HCl. The resulting precipitate was collected by filtration and purified by prep. HPLC (Agilent, BOSTON, 250×2.12 mm, 10 µm column, eluting with a gradient of ACN in water with 0.1% formic acid at a flow rate of 20.0 mL/min) to give the title compound as a mixture of atropisomers (1:1 racemate:meso, 15 mg, 12%). LCMS-C (ES-API): rt 2.43 min, m/z 751.1 [M+H]$^+$ and 2.72 min, m/z 751.1 [M+H]$^+$. $^1$H NMR (400 MHz, DMSO-d$_6$) δ 8.48-8.45 (m, 2H), 8.22 (s, 2H), 8.10-7.98 (m, 2H), 7.94-7.55 (m, 7H), 7.40-7.21 (m, 3H), 4.54-4.52 (m, 2H), 4.22-4.10 (m, 2H).

Diethyl 3,3'-(ethane-1,2-diylbis(5-carbamoyl-1H-benzo[d]imidazole-1,2-diyl))bis(4-(trifluoromethyl) benzo[b]thiophene-2-carboxylate) (18) and 3,3'-(Ethane-1,2-diylbis(5-carbamoyl-1H-benzo[d]imidazole-1,2-diyl))bis(4-(trifluoromethyl)benzo[b]thiophene-2-carboxylic acid) (19.1 and 19.2)

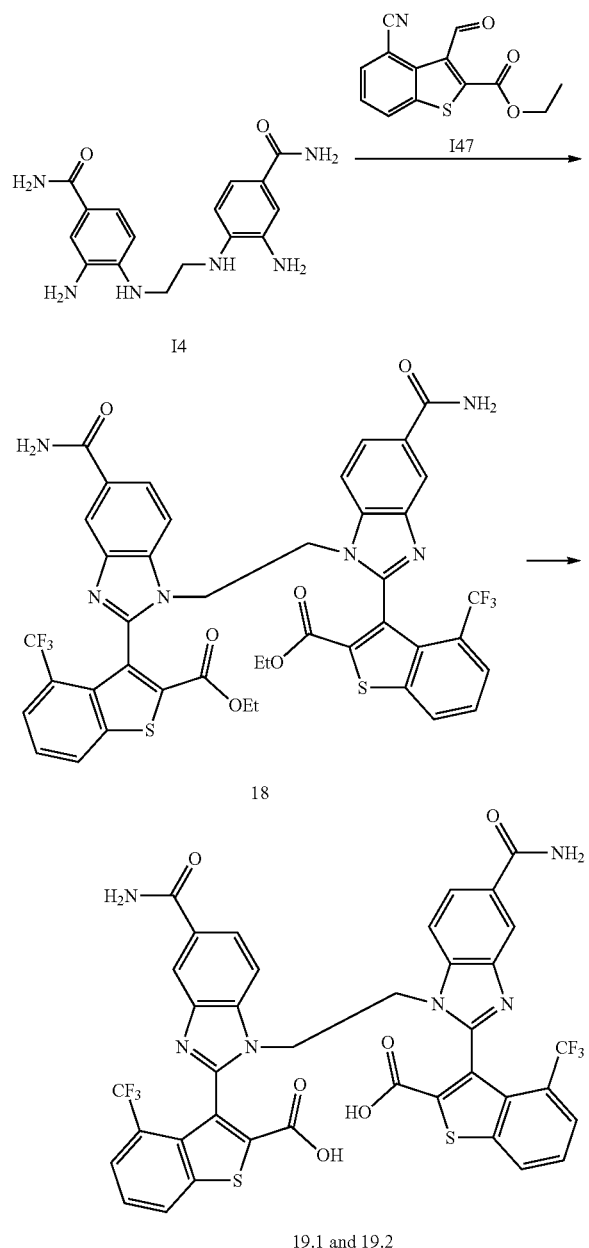

(a) Diethyl 3,3'-(ethane-1,2-diylbis(5-carbamoyl-1H-benzo[d]imidazole-1,2-diyl))bis(4-(trifluoromethyl)benzo[b]thiophene-2-carboxylate) (18)

To a solution of 4,4'-(ethane-1,2-diylbis(azanediyl))bis(3-aminobenzamide) (I4) (197 mg, 0.6 mmol) in DMF (4 mL) was added H$_2$O (0.1 mL) followed by oxone (369 mg, 0.6 mmol). A solution of ethyl 3-formyl-4-(trifluoromethyl)benzo[b]thiophene-2-carboxylate (I47) (300 mg, 1.0 mmol) in DMF (2 mL) was then added dropwise over 1 h and the mixture was heated at 80° C. for 2 days. Water (20 mL) was added and the resulting precipitate was collected by filtration and triturated with a 1:1 mixture of Pet. Ether/EtOAc to give the title compound (183 mg, 21%) as a black solid (mixture of atropisomeric diastereomers in ~1.5:1 ratio). LCMS-B (ES-API): rt 3.20 min, m/z 893.2 [M+H]$^+$. $^1$H NMR (400 MHz, DMSO-d$_6$) δ 8.66-8.64 (m, 1H), 8.52-8.50 (m, 1H), 8.23-8.20 (m, 2H), 8.06-7.98 (m, 5H), 7.96-7.84 (m, 4H), 7.78-7.76 (m, 1H), 7.32 (br s, 2H), 4.52-4.35 (m, 2.4H), 4.14-4.07 (m, 1.6H), 4.05 (q, J=7.1 Hz, 1.6H), 3.54 (q, J=7.1 Hz, 2.4H), 0.90 (t, J=7.1 Hz, 2.4H), 0.74 (t, J=7.1 Hz, 3.6H).

(b) 3,3'-(Ethane-1,2-diylbis(5-carbamoyl-1H-benzo[d]imidazole-1,2-diyl))bis(4-(trifluoromethyl)benzo[b]thiophene-2-carboxylic acid) (19.1 and 19.2)

To a solution of diethyl 3,3'-(ethane-1,2-diylbis(5-carbamoyl-1H-benzo[d]imidazole-1,2-diyl))bis(4-(trifluoromethyl)benzo[b]thiophene-2-carboxylate) (18) (183 mg, 0.20 mmol) in EtOH/water (8 mL, 10:1) was added NaOH (80 mg, 2.0 mmol) and the mixture was stirred at room temperature overnight. Most of the EtOH was removed under reduced pressure and the aqueous layer was adjusted to pH 5 with 1 M aqueous HCl. The resulting precipitate was collected by filtration and purified by prep. HPLC (Agilent Prep Star 218, 150×20 mm, 5 μm column, eluting with a gradient of ACN in water with 0.1% formic acid at a flow rate of 20.0 mL/min) to give separated atropisomers of the title compound (19.1) (peak 1: 5 mg, 3%) and (19.2) (peak 2: 10.8 mg, 7%) as brown solids.

Peak 1 (Prep HPLC, rt, 10.27 min): (19.1); LCMS-B (ES-API): rt 2.66 min, m/z 837.1 [M+H]$^+$;

$^1$H NMR (400 MHz, DMSO-d$_6$) δ 8.51 (d, J=7.1 Hz, 2H), 8.21 (s, 2H), 8.01 (br s, 2H), 7.94-7.70 (m, 8H), 7.27 (br s, 2H), 4.29-4.19 (m, 4H).

Peak 2 (Prep HPLC, rt, 14.98 min): (19.2); LCMS-B (ES-API): rt 2.77 min, m/z 837.1 [M+H]$^+$;

$^1$H NMR (400 MHz, DMSO-d$_6$) δ 8.50-8.48 (m, 2H), 8.22 (s, 2H), 8.01 (br s, 2H), 7.93-7.86 (m, 2H), 7.79-7.69 (m, 6H), 7.28 (br s, 2H), 4.43-4.41 (m, 2H), 4.07-4.05 (m, 2H).

3,3'-(Ethane-1,2-diylbis(5-carbamoyl-1H-benzo[d]imidazole-1,2-diyl))bis(4-bromo-7-fluorobenzo[b]thiophene-2-carboxylic acid) (20.1 and 20.2)

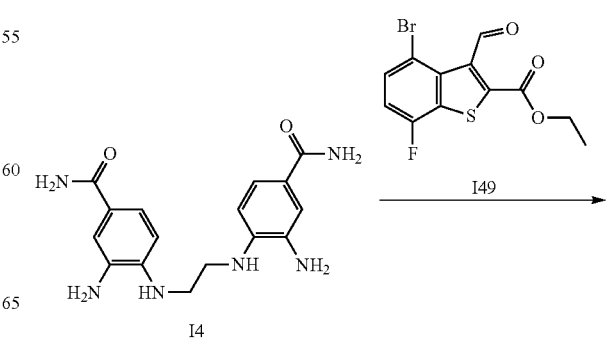

-continued

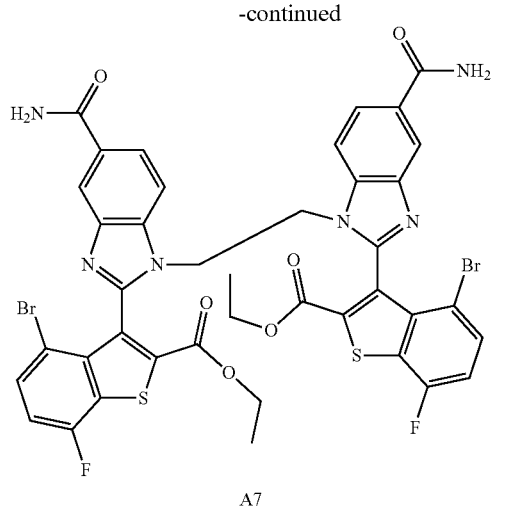

A7

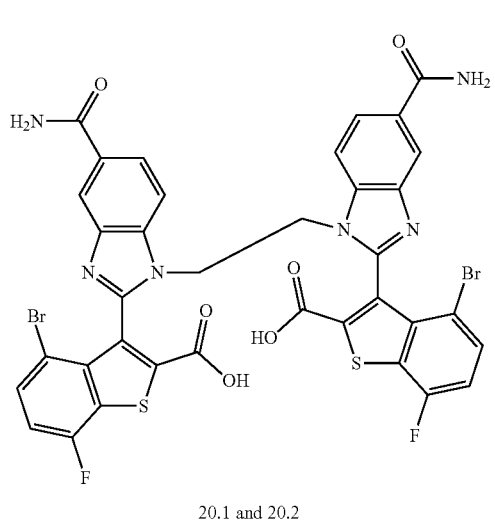

20.1 and 20.2

(a) Diethyl 3,3'-(ethane-1,2-diylbis(5-carbamoyl-1H-benzo[d]imidazole-1,2-diyl))bis(4-bromo-7-fluorobenzo[b]thiophene-2-carboxylate) (A7)

A mixture of 4,4'-(ethane-1,2-diylbis(azanediyl))bis(3-aminobenzamide) (I4) (200 mg, 0.61 mmol) and ethyl 4-bromo-7-fluoro-3-formylbenzo[b]thiophene-2-carboxylate (I49) (404 mg, 1.22 mmol) in AcOH/EtOH (10 mL/10 mL) was heated at 50° C. for 6 h. The solvent was removed under reduced pressure and the residue was dissolved in EtOAc, washed with water and brine, dried over $Na_2SO_4$, filtered and concentrated under reduced pressure. The residue was purified by silica gel chromatography (DCM/MeOH=20:1) to give the title compound (260 mg, 45%) as a yellow solid. LCMS-B (ES-API): rt 3.61 min; m/z 475.0 $[M/2+H]^+$.

(b) 3,3'-(Ethane-1,2-diylbis(5-carbamoyl-1H-benzo[d]imidazole-1,2-diyl))bis(4-bromo-7-fluorobenzo[b]thiophene-2-carboxylic acid) (20.1 and 20.2)

To a solution of 3,3'-(ethane-1,2-diylbis(5-carbamoyl-1H-benzo[d]imidazole-1,2-diyl))bis(4-bromo-7-fluorobenzo[b]thiophene-2-carboxylate) (A7) (260 mg, 0.27 mmol) in EtOH (10 mL) was added a solution of NaOH (65 mg, 1.62 mmol) in water (2 mL) and the mixture was heated at 50° C. overnight. Most of the EtOH was removed under reduced pressure and the aqueous residue was adjusted to pH 3-4 with 1 M aqueous HCl. The resulting precipitate was collected by filtration and purified by prep. HPLC (Agilent 10 prep-C18, 250×21.2 mm, 10 μm column, eluting with a gradient of MeOH in water with 0.1% TFA, at a flow rate of 20 mL/min) to give separated atropisomers of the title compound (20.1) (peak 1:25 mg, 10%) and title compound (20.2) (peak 2: 90 mg, 37%) as yellow solids.

Peak 1: (Prep HPLC, rt, 8.59 min): (20.1); LCMS-B (ES-API): rt 2.83 min, m/z 892.8, 894.9 $[M+H]^+$; $^1$H NMR (400 MHz, DMSO-$d_6$) δ 8.21 (s, 2H), 8.02 (br s, 2H), 7.87 (d, J=8.4 Hz, 2H), 7.70-7.59 (m, 4H), 7.42 (t, J=8.8 Hz, 2H), 7.27 (br s, 2H), 4.51-4.34 (m, 4H).

Peak 2: (Prep HPLC, rt, 10.72 min): (20.2); LCMS-B (ES-API): rt 3.02 min, m/z 892.8, 894.8 $[M+H]^+$; $^1$H NMR (400 MHz, DMSO-$d_6$) δ 8.26-7.75 (m, 8H), 7.44-7.32 (m, 6H), 4.51-4.29 (m, 4H).

Diethyl 3,3'-(ethane-1,2-diylbis(5-carbamoyl-4-methoxy-1H-benzo[d]imidazole-1,2-diyl))bis(4-chlorobenzo[b]thiophene-2-carboxylate) (21) and 3,3'-(ethane-1,2-diylbis(5-carbamoyl-4-methoxy-1H-benzo[d]imidazole-1,2-diyl))bis(4-chlorobenzo[b]thiophene-2-carboxylic acid) (22.1 and 22.2)

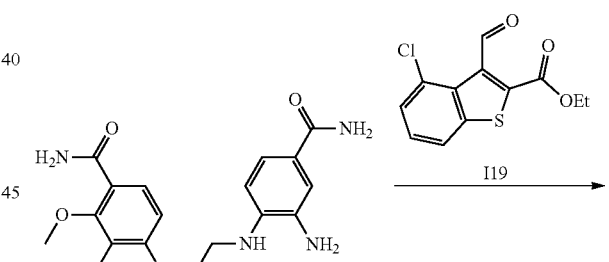

I33

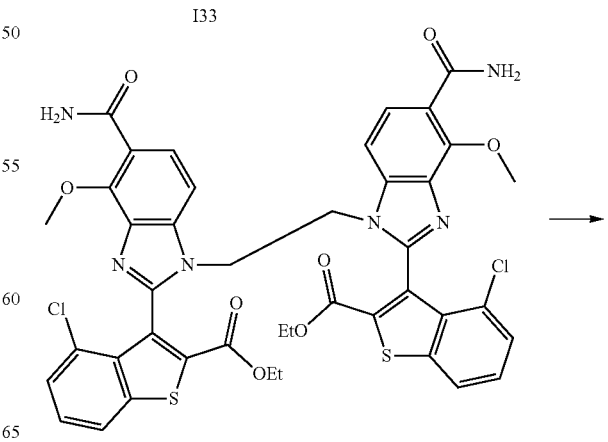

21

-continued

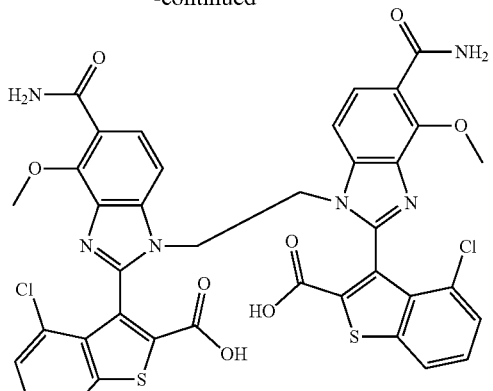

22.1 and 22.2

(a) Diethyl 3,3'-(ethane-1,2-diylbis(5-carbamoyl-4-methoxy-1H-benzo[d]imidazole-1,2-diyl))bis(4-chlorobenzo[b]thiophene-2-carboxylate) (21)

A mixture of 4,4'-(ethane-1,2-diylbis(azanediyl))bis(3-amino-2-methoxybenzamide) (I33) (145 mg, 0.37 mmol), ethyl 4-chloro-3-formylbenzo[b]thiophene-2-carboxylate (I19) (200 mg, 0.74 mmol) and $NaHSO_3$ (78 mg, 0.74 mmol) in DMF (15 mL) was heated at 120° C. under $N_2$ for 16 h. The mixture was poured into water (80 mL), extracted with EtOAc (80 mL×3) and the combined organic extracts were washed water (80×2 mL), brine (80 mL), dried over $Na_2SO_4$, filtered and concentrated under reduced pressure. The residue was purified by prep. TLC (DCM/MeOH=15:1) to give the title compound (130 mg, 39%) as a yellow solid (mixture of atropisomeric diastereomers: $^1$H NMR showed a 1:1 mixture of racemate:meso). LCMS-C (ES-API): rt 4.53 min, m/z 885.2, 887.2 [M+H]$^+$. $^1$H NMR (400 MHz, DMSO-$d_6$) δ 8.27-8.25 (m, 1H), 8.16-8.14 (m, 1H), 7.89 (s, 2H), 7.67-7.65 (m, 3H), 7.54-7.43 (s, 6H), 7.29-7.27 (m, 1H), 4.47-4.42 (m, 2H), 4.25-4.23 (m, 10H), 4.06-4.05 (m, 2H), 0.95 (t, J=6.4 Hz, 3H), 0.79 (t, J=6.8 Hz, 3H)

(b) 3,3'-(Ethane-1,2-diylbis(5-carbamoyl-4-methoxy-1H-benzo[d]imidazole-1,2-diyl))bis(4-chlorobenzo[b]thiophene-2-carboxylic acid) (22.1 and 22.2)

To a solution of 3,3'-(ethane-1,2-diylbis(5-carbamoyl-4-methoxy-1H-benzo[d]imidazole-1,2-diyl))bis(4-chlorobenzo[b]thiophene-2-carboxylate) (21) (130 mg, 0.15 mmol) in EtOH/$H_2O$ (8 mL/8 mL) was added NaOH (35 mg, 0.90 mmol) and the mixture was heated at 80° C. for 16 h. The solvent was removed under reduced pressure and the residue was diluted with water (10 mL) and adjusted to pH 4-5 with 2 M aqueous HCl. The resulting precipitate was collected by filtration and purified by prep. HPLC (Agilent, BOSTON, 250×2.12 mm, 10 μm column, eluting with a gradient of ACN in water with 0.1% formic acid at a flow rate of 20.0 mL/min) to give separated atropisomers of the title compound (22.1) (peak 1: 5 mg, 4%) and the title compound (22.2) (peak 2: 10 mg, 8%) as white solids.

Peak 1 (Prep HPLC, rt 12.08 min): (22.1); LCMS-C (ES-API): rt 3.58 min, m/z 829.1, 831.0 [M+H]$^+$; $^1$H NMR (400 MHz, DMSO-$d_6$) δ 8.17 (d, J=8.1 Hz, 2H), 7.72 (d, J=8.2 Hz, 2H), 7.67 (s, 2H), 7.58 (t, J=7.9 Hz, 2H), 7.46-7.44 (m, 4H), 7.25-6.61 (m, 2H), 4.37-4.28 (m, 2H), 4.29 (s, 6H), 4.18-4.16 (m, 2H).

Peak 2 (Prep HPLC, rt 14.84 min): (22.2); LCMS-C (ES-API): rt 3.80 min, m/z 829.1, 831.0 [M+H]$^+$; $^1$H NMR (400 MHz, DMSO-$d_6$) δ 8.14 (d, J=7.7 Hz, 2H), 7.91-7.73 (m, 2H), 7.68 (s, 2H), 7.58-7.48 (m, 2H), 7.44 (s, 2H), 7.30 (d, J=7.3 Hz, 2H), 7.19-7.04 (m, 2H), 4.45-4.43 (m, 2H), 4.28 (s, 6H), 4.12-4.01 (m, 2H).

Diethyl 3,3'-(ethane-1,2-diylbis(5-carbamoyl-1H-benzo[d]imidazole-1,2-diyl))bis(4-ethoxybenzo[b]thiophene-2-carboxylate) (23) and 3,3'-(ethane-1,2-diylbis(5-carbamoyl-1H-benzo[d]imidazole-1,2-diyl))bis(4-ethoxybenzo[b]thiophene-2-carboxylic acid) (24)

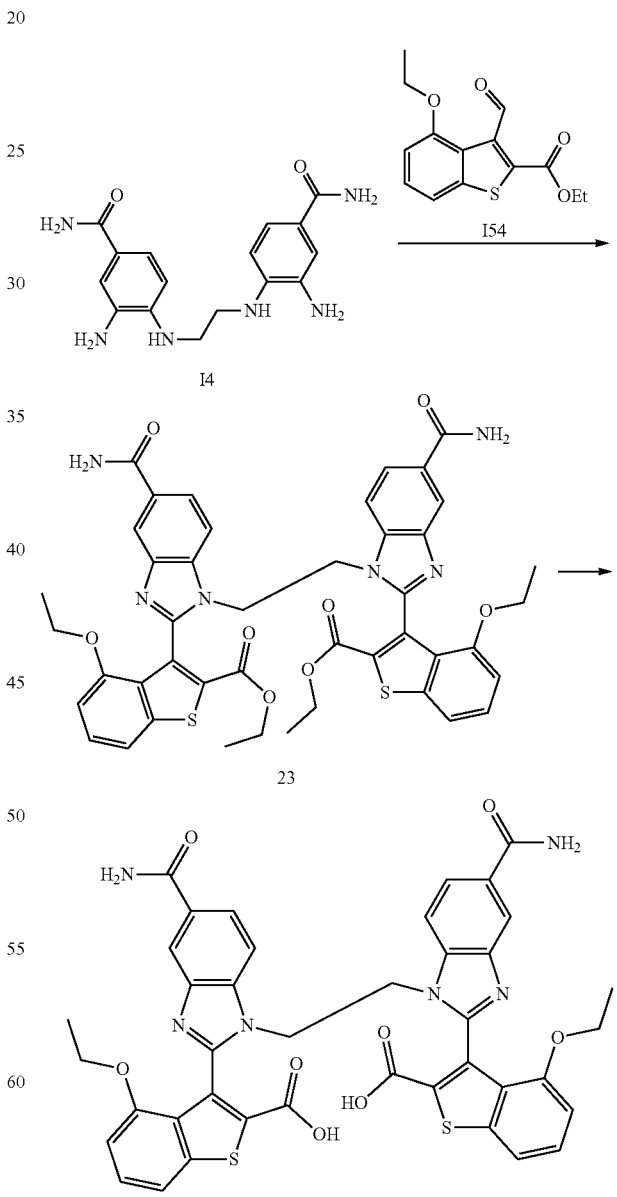

(a) Diethyl 3,3'-(ethane-1,2-diylbis(5-carbamoyl-1H-benzo[d]imidazole-1,2-diyl))bis(4-ethoxybenzo[b]thiophene-2-carboxylate) (23)

A solution of ethyl 4-ethoxy-3-formylbenzo[b]thiophene-2-carboxylate (I54) (500 mg, 1.8 mmol), 4,4'-(ethane-1,2-diylbis(azanediyl))bis(3-aminobenzamide) (I4) (300 mg, 0.91 mmol) and NaHSO$_3$ (175 mg, 1.8 mmol) in DMF (25 mL) was heated at 80° C. overnight. The mixture was diluted with water, extracted with EtOAc and the combined organic extracts were washed with brine, dried over Na$_2$SO$_4$, filtered and concentrated under reduced pressure to give the title compound (200 mg, 26%) as a pink solid. LCMS-B (ES-API): rt 3.20 min, m/z 845.2 [M+H]$^+$. $^1$H NMR (400 MHz, DMSO-d$_6$) δ 8.19 (s, 2H), 8.05 (br s, 2H), 7.95 (d, J=8.4 Hz, 2H), 7.76 (d, J=8.7 Hz, 2H), 7.71 (d, J=8.3 Hz, 2H), 7.57-7.47 (m, 2H), 7.29 (br s, 2H), 6.82 (d, J=8.1 Hz, 2H), 4.55-4.44 (m, 2H), 4.09-4.07 (m, 2H), 3.69-3.57 (m, 4H), 3.51-3.45 (m, 4H), 0.74 (t, J=7.0 Hz, 6H), 0.35 (t, J=7.0 Hz, 6H).

(b) 3,3'-(Ethane-1,2-diylbis(5-carbamoyl-1H-benzo[d]imidazole-1,2-diyl))bis(4-ethoxybenzo[b]thiophene-2-carboxylic acid) (24)

To a solution of diethyl 3,3'-(ethane-1,2-diylbis(5-carbamoyl-1H-benzo[d]imidazole-1,2-diyl))bis(4-ethoxybenzo[b]thiophene-2-carboxylate) (23) (15 mg, 0.018 mmol) in EtOH (8 mL) was added a solution of NaOH (7 mg, 0.18 mmol) in H$_2$O (1 mL) and the mixture was stirred at room temperature overnight. Most of the EtOH was removed under reduced pressure and the aqueous residue was adjusted to pH 5 with 1 M aqueous HCl. The resulting precipitate was collected by filtration and dried under reduced pressure to give the title compound as a ~1.8:1 mixture of atropisomers (5 mg, 35%) as a black solid. LCMS-C (ES-API): rt 2.98 min, m/z 789.2 [M+H]$^+$ & 3.07 min, m/z 789.2 [M+H]$^+$. $^1$H NMR (400 MHz, DMSO-d$_6$) δ 8.13-8.08 (m, 2H), 7.96-7.90 (m, 2H), 7.65-7.48 (m, 4H), 7.34 (t, J=7.8 Hz, 2H), 7.19 (br s, 0.7H), 7.16 (s, 1.3H), 6.74-6.63 (m, 2H), 6.49-6.42 (m, 0.7H), 6.36-6.30 (m, 1.3H), 4.54-4.45 (m, 1H), 4.24-4.11 (m, 2H), 4.06-3.93 (m, 2H), 3.83-3.76 (m, 1H), 3.58-3.50 (m, 2H), 1.08 (t, J=7.3 Hz, 6H).

Assays
Protein Production and Purification

Biophysical experiments were performed with three different recombinant human STING protein variants designated according to allelic nomenclature of Yi et al., (2013). Codon optimized DNA sequences (for expression in *Escherichia coli*) encoding amino acid residues 149 to 345 (Swiss Prot Q86WV6) of human STING (WT), human STING (HAQ) and human STING (R232H) were synthesized by GenScript USA Inc (Piscataway, N.J., USA). These were ligated into a modified pET43a *E. coli* expression vector designed to encode N-terminal His tag followed by tobacco etch virus protease (TEV) cleavage site and a STING gene sequence. The resulting protein sequences for the three allelic variants are listed below:

```
His-TEV-hSTING(WT)
MGHHHHHHGTENLYFQGSE149KGNFNVAHGLAWSYYIGYLRLILPELQA

RIRTYNQHYNNLLRGAVSQRLYILLPLDCGVPDNLSMADPNIRFLDKLP

QQTGDRAGIKDRVYSNSIYELLENGQRAGTCVLEYATPLQTLFAMSQYS
```

-continued
```
QAGFSREDRLEQAKLFCRTLEDILADAPESQNNCRLIAYQEPADDSSFS

LSQEVLRHLRQEEKEEVTVGS345

His-TEV-hSTING(R232H)
MGHHHHHHGTENLYFQGSE149KGNFNVAHGLAWSYYIGYLRLILPELQA

RIRTYNQHYNNLLRGAVSQRLYILLPLDCGVPDNLSMADPNIRFLDKLP

QQTGDHAGIKDRVYSNSIYELLENGQRAGTCVLEYATPLQTLFAMSQYS

QAGFSREDRLEQAKLFCRTLEDILADAPESQNNCRLIAYQEPADDSSFS

LSQEVLRHLRQEEKEEVTVGS345

His-TEV-hSTING(HAQ)
MGHHHHHHGTENLYFQGSE149KGNFNVAHGLAWSYYIGYLRLILPELQA

RIRTYNQHYNNLLRGAVSQRLYILLPLDCGVPDNLSMADPNIRFLDKLP

QQTADRAGIKDRVYSNSIYELLENGQRAGTCVLEYATPLQTLFAMSQYS

QAGFSREDRLEQAKLFCQTLEDILADAPESQNNCRLIAYQEPADDSSFS

LSQEVLRHLRQEEKEEVTVGS345
```

To produce recombinant human STING proteins, expression plasmid encoding above-described constructs were transformed into *E. coli* BL21 DE3 strain and grown with shaking at 37° C. in 2×1 L volumes of Terrific broth (TB) supplemented with 100 μg/ml Ampicillin until OD$_{600}$ of 0.8 was reached. Cultures were then cooled to 16° C. and protein expression induced by the addition of isopropyl β-D-1-thiogalactopyranoside to a final concentration of 0.5 mM and the cultures shaken overnight for further 16 hours. Following expression, cell cultures were centrifuged at 5000×g for 20 min and cell pellet stored frozen at −70° C.

Protein purification was initiated by thawing the cell pellet in Lysis buffer (25 mM Tris-HCl pH 8.0, 300 mM NaCl, 5 mM DTT, 2 mM MgCl$_2$, 10 mM imidazole, 0.5 mg/ml lysozyme, benzonase endonuclease [EMD Millipore], 1 mM PMSF, complete protease inhibitor tablets EDTA-free [Roche]) using a ratio of 7 ml of buffer per 1 g of cells. Cells were further lysed by 3 passes through an ice cooled Avestin C5 cell crusher and then centrifuged at 48,000×g at 4° C. Supernatant (cell lysate) was filtered through a 5 μm filter and loaded onto 5 mL HiTrap IMAC Sepharose FF column (GE Healthcare) pre-equilibrated with IMAC wash buffer 1 (25 mM Tris-HCl pH 8.0, 300 mM NaCl, 5 mM DTT, 10 mM imidazole) using Profinia Affinity chromatography purification system (Bio-Rad). The IMAC column was then sequentially washed with IMAC Wash buffer 1 and IMAC Wash buffer 2 (25 mM Tris-HCl pH 8.0, 300 mM NaCl, 5 mM DTT, 20 mM Imidazole) and bound His-TEV-hSTING protein eluted with IMAC Elution buffer (25 mM Tris-HCl pH 8.0, 300 mM NaCl, 5 mM DTT, 250 mM Imidazole). IMAC-eluted protein was further purified by passing through a HiLoad 26/60 Superdex 75 column pre-equilibrated in storage buffer (25 mM Tris-HCl, pH 8.0, 150 mM NaCl, 5 mM DTT 0.02% [w/v] sodium azide). Finally, hSTING protein was concentrated to ≥2 mg/ml using Amicon Ultra centrifugal filter unit (Utra-15 MWCO 10 kDa), flash-frozen in liquid nitrogen and stored in −70° C. freezer.

Differential Scanning Fluorimetry (DSF)

Differential scanning fluorimetry (DSF) is a rapid screening method for identifying low-molecular-weight ligands that bind and, in doing so, stabilize (or sometimes destabilize) purified proteins (Niesen 2007). DSF monitors thermal unfolding of protein in the presence of a fluorescent dye and is typically performed using a real-time PCR instrument. The temperature at which a protein unfolds is measured by an increase in the fluorescence of a dye with affinity for hydrophobic parts of the protein that are gradually being exposed during unfolding. The fluorescence of the dye is quenched in aqueous environments, but when the dye associates with hydrophobic sites on unfolded protein, its fluorescence increases. The fluorescence intensity is plotted as a function of the temperature, generating a sigmoidal curve that can be described by a two-state transition. The inflection point of the transition curve (Tm) is calculated using simple equations such as that of Boltzmann.

Thermal stability of STING protein (with and without bound ligand) was measured using previously described methodology (Seabrook & Newman, 2013), with samples tested in triplicate using 96-well PCR microplate (AB Gene, ABGAB-0600/W). In a final volume of 20 μL, 2 μM protein in 1×HBS buffer (50 mM HEPES, pH 7.4, 150 mM NaCl) was mixed with SYPRO Orange dye (Sigma-Aldrich S5692, final reaction mix dilution 1:1200) and a compound (final concentration at 100 μM). Sealed plates were placed into Bio-Rad CFX96/C1000 thermocycler and FRET scanning mode ($\lambda^{excitation}$ of 490 nm and reads at a $\lambda^{emission}$ of 570 nm). Melting curves were recorded from 20° C. to 100° C. in 0.5° C. increments every 30 seconds with a read at each increment. Data were analyzed using "Meltdown analysis" protocol described by Rosa (2015). The melting temperature ($T_m$) obtained for STING protein alone (1% [v/v] DMSO) was subtracted from $T_m$ obtained for protein incubated with ligand to generate $\Delta T_m$ values listed in the table below. DSF data was generated for each compound against 3 different STING protein variants—human STING (WT), human STING (HAQ) and human STING (R232H).

| Example | DSF huSTING (HAQ) ΔTm (° C.) | DSF huSTING (WT) ΔTm (° C.) | DSF huSTING (R232H) ΔTm (° C.) |
| --- | --- | --- | --- |
| 1.1 | 31.8 | 19.9 | 12.1 |
| 1.2 | 0.13 | −7.14 | −4.3 |
| 2.1 | 32 | 21 | 11.8 |
| 2.2 | 22.2 | 8.85 | 6.9 |
| 3 | −0.55 | −1.83 | −0.15 |
| 4.1 | 2.85 | −0.82 | −2.0 |
| 4.2 | 4.56 | −0.76 | −0.91 |
| 5.2 | 30.94 | 19.17 | 11.27 |
| 5.1 | 23.59 | 6.4 | 7.51 |
| 7 | 6.96 | 0.6 | −0.34 |
| 9 | 6.7 | 2.36 | 1.03 |
| 11.1 | 31.05 | 17.83 | 10.45 |
| 11.2 | −1.75 | −5.12 | −1.64 |
| 13.1 | 31.23 | 18.17 | 11.81 |
| 13.2 | 0.89 | −1.43 | −2.9 |
| 15.1 | 24.64 | 10.53 | 6.6 |
| 15.2 | 31.87 | 20.41 | 10.23 |
| 17 | 3.27 | −2.58 | −3.79 |
| 19.1 | 21.36 | 9.38 | 8.21 |
| 19.2 | 12.26 | 2.74 | 1.85 |
| 20.1 | 31.76 | 22.71 | 14.94 |
| 20.2 | 0.44 | −4.12 | −4.15 |
| 21 | 4.33 | 3.41 | 37.65 |
| 22.1 | 45.505 | 37.67 | 30.585 |
| 22.2 | 45.31 | 35.685 | 28.13 |
| 24 | 3.15 | −0.39 | 0.81 |
| A1 | 0.36 | 1.84 | 18.93 |

Surface Plasmon Resonance (SPR)

Binding interactions of ligands with STING proteins were quantified using Surface Plasmon Resonance (SPR) with a minimally biotinylated STING protein immobilized on a streptavidin chip surface. In this manner highly active STING protein surfaces were obtained that were not compromised by a low pH required for an amine coupling method. Minimal biotinylation of purified huSTING proteins was performed using a previously described methodology (Chhabra 2012). Briefly, approximately 20 nmol of recombinant STING protein in 1×TBS buffer (25 mM Tris-HCl, pH 7.5, 150 mM NaCl, 5 mM DTT) was mixed with of EZ-Link™ Sulfo-NHS-LC-LC-Biotin (Thermofisher Scientific, cat #21338) at a molar ratio of 1 to 0.6 and incubated on ice for 2 hours. To remove any unreacted biotin reagent, protein/biotin mixture was passed through a Superdex 75 (10/300 GL) column equilibrated with 10 mM HEPES, pH 7.4, 150 mM NaCl, 5 mM DTT, 5% [v/v] glycerol. A protein peak containing biotinylated huSTING protein was collected and stored in aliquots at −80° C.

Streptavidin was simultaneously immobilized in all four channels of a CM5 sensor chip docked in a Biacore instrument (either Biacore S200 or Biacore T200, GE Healthcare) as described previously (Zender 2013). Minimally biotinylated STING protein was captured onto a streptavidin coated chip surface at 8° C. in SPR binding buffer (50 mM HEPES, pH 7.4, 150 mM NaCl, 2% [v/v] DMSO) by gradually injecting in a single channel at a constant flow-rate of 2 μL/min until desired capture level was achieved, typically 3000 to 7000 RU (1 RU=1 pg/mm²).

All binding experiments were performed at 8° C. in SPR binding buffer. To determine binding affinity, compound interaction with immobilized STING protein was analyzed using dose-response experiments. Fresh 10 mM DMSO solutions of compound were diluted directly into SPR binding buffer typically to a concentration of 50 μM and then further diluted 2-fold or 3-fold aiming for either a 5- or 7-point concentration series range. Each ligand concentration series was injected at a constant flow rate of 60 μL/min with a 90 second association and a 180 second dissociation time. These were modified for compounds with longer residence times, so that curves could reach steady-state, or so that compound would be fully dissociated before the subsequent injection. Where appropriate, tighter-binding compounds (roughly $K_D<1$ uM) were tested using a single-cycle kinetics format (Karlsson 2006), with long association and dissociation times (typically 450 s and 1800 s, respectively).

Scrubber 2 (www.biologic.com.au) was utilized for data processing, where signals were referenced against the blank surface (streptavidin+D-biotin) and further corrected for DMSO refractive index change and then "double-referenced" using a buffer-blank injection (Papalia 2006). Responses were fitted to either a 1:1 steady-state affinity model or a 1:1 kinetic model (that included a mass-transport component), available within Scrubber.

| Example | SPR (HAQ) $K_D$ (μM) | SPR (WT) $K_D$ (μM) |
| --- | --- | --- |
| 1.1 | 0.0017 | 0.119 |
| 1.2 | — | — |
| 2.1 | 0.0074 | 0.031 |
| 2.2 | 0.124 | — |
| 3 | 5.06 | 6.3 |
| 4.1 | 35.13 | 500 |
| 4.2 | 16.61 | 23 |
| 5.1 | 0.02091 | 0.692 |
| 5.2 | 0.0014 | 0.122 |
| 7 | 28 | 80 |
| 9 | 10.1 | |
| 11.1 | 0.001638 | 0.063 |
| 11.2 | | 1.43 |

-continued

| Example | SPR (HAQ) $K_D$ (μM) | SPR (WT) $K_D$ (μM) |
|---|---|---|
| 13.1 | 0.004002 | 0.29995 |
| 13.2 |  | 2.371 |
| 15.1 |  | 0.43 |
| 15.2 | 0.004984 | 0.191 |
| 17 | 38 |  |
| 20.1 | 0.001652 | 0.016 |
| 24 | 37 |  |
| A1 | 14.9 | 15.95 |

THP-1 Reporter Cell Line Assays

THP-1 STING Lucia ISG cells (InvivoGen #thpl-isg) were cultured in RPMI-1640 containing 2 mM L-glutamine, 25 mM HEPES, 100 μg/mL Normocin (InvivoGen) and 10% heat-inactivated FBS. Cells were seeded at a density of $7 \times 10^5$ cells/mL, maintained at 37° C./5% $CO_2$, and passaged every 3-4 days. Selection pressure was maintained by the addition of 100 μg/mL Zeocin every second passage.

Assay conditions: cells were harvested and resuspended at a concentration of $5 \times 10^5$ cells/mL in fresh growth media. Of this cell preparation 20 μL per well was dispensed into 384 well cell culture plates (Greiner, #781098X) and incubated at 37° C./5% $CO_2$ for 2 hours.

Concentration Response Curves (commonly 11 doses) were prepared by 2.5 fold serial dilution starting from 10 mM compound stock solution in DMSO. Compound dilutions were transferred into the cell culture plates using a pintool (0.1 μL transfer), control wells were matched for DMSO. Positive control wells received ML RR-S2 CDA (Med Chem Express HY12885B) in 5 μL of media to a final concentration of 40 μM. All other wells received additional 5 μL of media only to equalize volume. The plates were incubated for 24 h at 37° C./5% $CO_2$.

For the detection step, QUANTI-Luc (InvivoGen #rep-qlc1) was prepared according to manufacturer's instruction and 10 μL were added per well to the culture plates. Plates were shaken for ten seconds on an orbital shaker and left in the dark at room temperature for two minutes, before luminescence was read on a Perkin Elmer Envision plate reader.

Data analysis: Luminescence raw data was normalized % activity relative to the signal of the positive control wells and negative control wells which were not treated with compound. The following formula was used to calculate normalized % activity from raw signals:

% activity=(sample−negative)/(positive−negative)

The THP-1 STING Lucia ISG cell $EC_{50}$ provides an assessment of activity at the human HAQ isoform of STING. For assessing compound activity against the WT human STING isoform, an equivalent method was conducted where the cells used were THP-1-Dual KI-hSTING-R232 (InvivoGen #thpd-r232).

| Example | $EC_{50}$ THP-I STING Lucia ISG cells (μM) | $EC_{50}$ THP-1 Dual KI-hSTING-R232 cells (μM) |
|---|---|---|
| 1.1 | 0.681 | 0.271 |
| 1.2 | 14.2 | 6.33 |
| 2.1 | 1.83 | 0.518 |
| 2.2 | 8.32 | 4.30 |
| 3 | >40 | >40 |
| 4.1 | >40 | >40 |
| 4.2 | >40 | 18.97 |
| 5.1 | >40 | 13.59 |
| 5.2 | 1.66 | 0.489 |
| 6 | >40 | >40 |
| 7 | >40 | 7.523 |
| 8 | >40 | >40 |
| 9 | >40 | 3.653 |
| 10 | 19.886 | 12.666 |
| 11.1 | 0.182 | 0.172 |
| 11.2 | 5.478 | 2.828 |
| 12 | 5.082 | 9.181 |
| 13.1 | 8.306 | 3.747 |
| 13.2 | >40 | >40 |
| 14 | >40 | >40 |
| 15.1 | 1.541 | 1.012 |
| 15.2 | 0.272 | 0.199 |
| 16 | >40 | >40 |
| 17 | 14.927 | 9.399 |
| 18 | 3.737 | >40 |
| 19.1 | 0.189 | 0.196 |
| 19.2 | 2.60 | 3.663 |
| 20.1 | 1.576 | 0.632 |
| 20.2 | 14.672 | 5.809 |
| 21 | 0.019 | 0.007 |
| 22.1 | 0.256 | 0.130 |
| 22.2 | 1.014 | 0.498 |
| 23 | >40 | >40 |
| 24 | >40 | >40 |
| A1 | 18.397 | 11.987 |
| A2 | 9.528 | 3.166 |

STATEMENTS OF INVENTION

1. A compound of formula I:

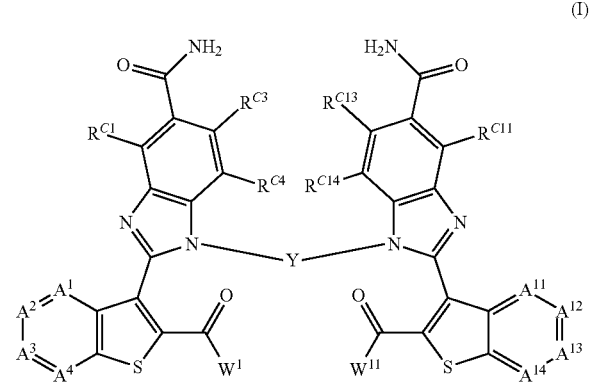

(I)

wherein:
Y is $(CH_2)_n$, where n is from 2 to 4;
$W^1$ and $W^{11}$ are independently selected from OH and $OR^P$, where $R^P$ is Me or Et;
$A^1$ is $CR^A$ or N;
$A^2$ is $CR^B$ or N;
$A^3$ is $CR^C$ or N;
$A^4$ is $CR^D$ or N;
where no more than two of $A^1$, $A^2$, $A^3$, and $A^4$ may be N;
one or two of $R^A$, $R^B$, $R^C$ and $R^D$, (if present) are selected from H, F, Cl, Br, Me, $CF_3$, cyclopropyl, cyano, OMe, OEt, $CH_2OH$, $CH_2OMe$ and OH;
the remainder of $R^A$, $R^B$, $R^C$ and $R^D$, (if present) are H;
$A^{11}$ is $CR^{AA}$ or N;
$A^{12}$ is $CR^{BB}$ or N;
$A^{13}$ is $CR^{CC}$ or N;

$A^{14}$ is $CR^{DD}$ or N;

where no more than two of $A^{11}$, $A^{12}$, $A^{13}$ and $A^{14}$ may be N;

one or two of $R^{AA}$, $R^{BB}$, $R^{CC}$ and $R^{DD}$ (if present) are selected from H, F, Cl, Br, Me, $CF_3$, cyclopropyl, cyano, OMe, OEt, $CH_2OH$, $CH_2OMe$ and OH;

the remainder of $R^{AA}$, $R^{BB}$, $R^{CC}$ and $R^{DD}$, (if present) are H;

$R^{C1}$, $R^{C3}$ and $R^{C4}$ are independently selected from H, Cl, F, Br, Me, OMe, OEt, cyano, $CF_3$, $CH_2OH$, $CH_2OMe$, $C_{2-4}$ alkenyl and $C_5$heterocyclyl;

$R^{C11}$, $R^{C13}$ and $R^{C14}$ are independently selected from H, Cl, F, Br, Me, OMe, OEt, cyano, $CF_3$, $CH_2OH$, $CH_2OMe$, $C_{2-4}$alkenyl and $C_5$heterocyclyl.

2. A compound according to statement 1, wherein $A^{11}=A^1$, $A^{12}=A^2$, $A^{13}=A^3$, $A^{14}=A^4$, $R^{C11}=R^{C1}$, $R^{C13}=R^{C3}$, $R^{C14}=R^{C4}$, $W^{11}=W^1$.

3. A compound according to statements 1 or 2, wherein $A^1$ is $CR^A$.

4. A compound according to statements 1 or 2, wherein $A^1$ is N.

5. A compound according to any one of statements 1 to 4, wherein $A^2$ is $CR^B$.

6. A compound according to any one of statements 1 to 4, wherein $A^2$ is N.

7. A compound according to any one of statements 1 to 6, wherein $A^3$ is $CR^C$.

8. A compound according to any one of statements 1 to 6, wherein $A^3$ is N.

9. A compound according to any one of statements 1 to 6, wherein $A^4$ is $CR^D$.

10. A compound according to any one of statements 1 to 6, wherein $A^4$ is N.

11. A compound according to statements 1 or 2, wherein $A^1$ is $CR^A$, $A^2$ is $CR^B$, $A^3$ is $CR^C$, and $A^4$ is $CR^D$.

12. A compound according to statements 1 or 2, wherein one of $A^1$, $A^2$, $A^3$ and $A^4$ are N.

13. A compound according to statements 1 or 2, wherein two of $A^1$, $A^2$, $A^3$ and $A^4$ are N.

14. A compound according to any one of statements 1 to 13, wherein $A^{11}$ is $CR^{AA}$.

15. A compound according to any one of statements 1 to 13, wherein $A^{11}$ is N.

16. A compound according to any one of statements 1 to 15, wherein $A^{12}$ is $CR^{BB}$.

17. A compound according to any one of statements 1 to 15, wherein $A^{12}$ is N.

18. A compound according to any one of statements 1 to 17, wherein $A^{13}$ is $CR^{CC}$.

19. A compound according to any one of statements 1 to 17, wherein $A^{13}$ is N.

20. A compound according to any one of statements 1 to 19, wherein $A^{14}$ is $CR^{DD}$.

21. A compound according to any one of statements 1 to 19, wherein $A^{14}$ is N.

22. A compound according to any one of statements 1 to 13, wherein $A^{11}$ is $CR^{AA}$, $A^{12}$ is $CR^{BB}$, $A^{13}$ is $CR^{CC}$, and $A^{14}$ is $CR^{DD}$.

23. A compound according to any one of statements 1 to 13, wherein one of $A^{11}$, $A^{12}$, $A^{13}$ and $A^{14}$ are N.

24. A compound according to any one of statements 1 to 13, wherein two of $A^{11}$, $A^{12}$, $A^{13}$ and $A^{14}$ are N.

25. A compound according to any one of statements 1 to 13, wherein the compound is of formula IIIb:

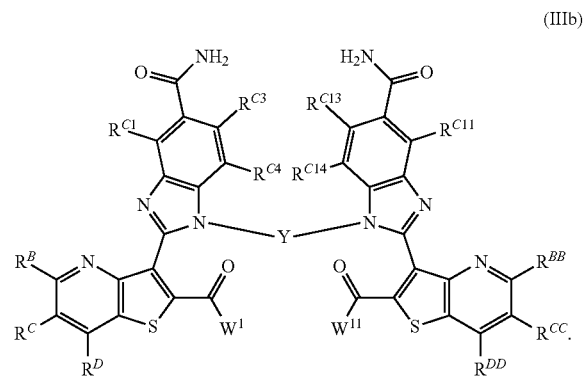

(IIIb)

26. A compound according to any one of statements 1 to 13, wherein the compound is of formula IIIc:

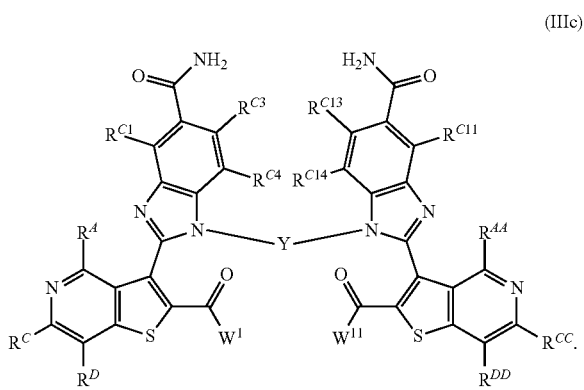

(IIIc)

27. A compound according to any one of statements 1 to 13, wherein the compound is of formula IIId:

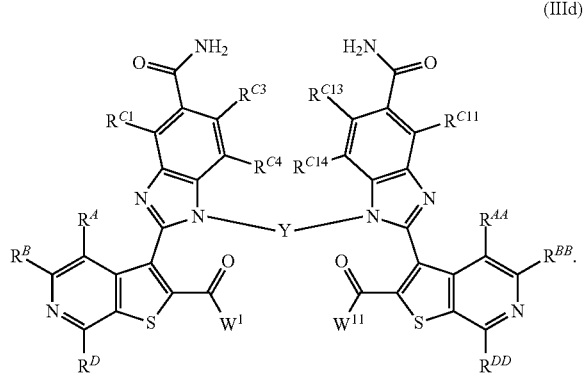

(IIId)

28. A compound according to any one of statements 1 to 13, wherein the compound is of formula IIIe:

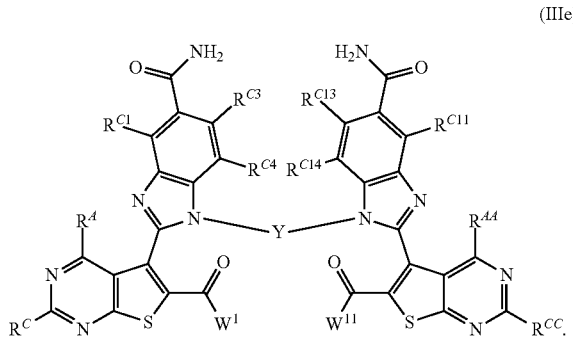

(IIIe)

29. A compound according to any one of statements 1 to 28, wherein one or two of $R^A$, $R^B$, $R^C$ and $R^D$, (if present) are selected from H, F, Cl, Br, Me, $CF_3$, cyclopropyl, cyano and OMe, the remainder (if present) are H.

30. A compound according to any one of statements 1 to 28, wherein one or two of $R^A$, $R^B$, $R^C$ and $R^D$, (if present) are selected from H, F, Cl, Br, Me, $CF_3$, cyclopropyl and OMe, the remainder (if present) are H.

31. A compound according to any one of statements 1 to 28, wherein one or two of $R^A$, $R^B$, $R^C$ and $R^D$, (if present) are selected from H, F, Cl, Br, Me, $CF_3$ and OMe, the remainder (if present) are H.

32. A compound according to any one of statements 1 to 31, wherein:
  $R^A$ (if present) is selected from H, F, Cl, Br, Me, $CF_3$, cyclopropyl, cyano, OMe, OEt and $CH_2OMe$;
  $R^B$ (if present) is H;
  $R^C$ (if present) is H;
  $R^D$ (if present) is selected from H, F, Cl, Br, Me, $CF_3$, cyclopropyl, cyano, OMe, $CH_2OH$ and $CH_2OMe$.

33. A compound according to any one of statements 1 to 31, wherein:
  $R^A$ (if present) is selected from F, Cl, Br, Me, $CF_3$, cyclopropyl, cyano and OMe;
  $R^B$ (if present) is H;
  $R^C$ (if present) is H;
  $R^D$ (if present) is selected from H, F, Br, Me and OMe.

34. A compound according to any one of statements 1 to 31, wherein:
  $R^A$ (if present) is selected from Cl, Br and OMe;
  $R^B$ (if present) is H;
  $R^C$ (if present) is H;
  $R^D$ (if present) is selected from H, F, Br, Me and OMe.

35. A compound according to statement 11, wherein:
  $R^A$ is Cl;
  $R^B$ is H;
  $R^C$ is H;
  $R^D$ is H.

36. A compound according to statement 11, wherein:
  $R^A$ is Cl;
  $R^B$ is H;
  $R^C$ is H;
  $R^D$ is Me.

37. A compound according to statement 11, wherein:
  $R^A$ is Cl;
  $R^B$ is H;
  $R^C$ is H;
  $R^D$ is Br.

38. A compound according to statement 11, wherein:
  $R^A$ is Br;
  $R^B$ is H;
  $R^C$ is H;
  $R^D$ is H.

39. A compound according to statement 11, wherein:
  $R^A$ is Cl;
  $R^B$ is H;
  $R^C$ is H;
  $R^D$ is F.

40. A compound according to statement 11, wherein:
  $R^A$ is Cl;
  $R^B$ is H;
  $R^C$ is H;
  $R^D$ is OMe.

41. A compound according to statement 11, wherein:
  $R^A$ is Br;
  $R^B$ is H;
  $R^C$ is H;
  $R^D$ is F.

42. A compound according to statement 11, wherein:
  $R^A$ is OMe;
  $R^B$ is H;
  $R^C$ is H;
  $R^D$ is H.

43. A compound according to statement 11, wherein:
  $R^A$ is $CF_3$;
  $R^B$ is H;
  $R^C$ is H;
  $R^D$ is H.

44. A compound according to statement 11, wherein:
  $R^A$ is $CH_3$;
  $R^B$ is H;
  $R^C$ is H;
  $R^D$ is H.

45. A compound according to any one of statements 1 to 44, wherein one or two of $R^{AA}$, $R^{BB}$, $R^{CC}$ and $R^{DD}$, (if present) are selected from H, F, Cl, Br, Me, $CF_3$, cyclopropyl, cyano and OMe, the remainder (if present) are H.

46. A compound according to any one of statements 1 to 44, wherein one or two of $R^{AA}$, $R^{BB}$, $R^{CC}$ and $R^{DD}$, (if present) are selected from H, F, Cl, Br, Me, $CF_3$, cyclopropyl and OMe, the remainder (if present) are H.

47. A compound according to any one of statements 1 to 44, wherein one or two of $R^{AA}$, $R^{BB}$, $R^{CC}$ and $R^{DD}$, (if present) are selected from H, F, Cl, Br, Me, $CF_3$ and OMe, the remainder (if present) are H.

48. A compound according to any one of statements 1 to 44, wherein:
  $R^{AA}$ (if present) is selected from H, F, Cl, Br, Me, $CF_3$, cyclopropyl, cyano, OMe, OEt and $CH_2OMe$;
  $R^{BB}$ (if present) is H;
  $R^{CC}$ (if present) is H;
  $R^{DD}$ (if present) is selected from H, F, Cl, Br, Me, $CF_3$, cyclopropyl, cyano, OMe, $CH_2OH$ and $CH_2OMe$.

49. A compound according to any one of statements 1 to 44, wherein:
  $R^{AA}$ (if present) is selected from F, Cl, Br, Me, $CF_3$, cyclopropyl, cyano and OMe;
  $R^{BB}$ (if present) is H;
  $R^{CC}$ (if present) is H;
  $R^{DD}$ (if present) is selected from H, F, Br, Me and OMe.

50. A compound according to any one of statements 1 to 44, wherein:
  $R^{AA}$ (if present) is selected from Cl, Br and OMe;
  $R^{BB}$ (if present) is H;
  $R^{CC}$ (if present) is H;

$R^{DD}$ (if present) is selected from H, F, Br, Me and OMe.

51. A compound according to statement 22, wherein:
$R^{AA}$ is Cl;
$R^{BB}$ is H;
$R^{CC}$ is H;
$R^{DD}$ is H.

52. A compound according to statement 22, wherein:
$R^{AA}$ is Cl;
$R^{BB}$ is H;
$R^{CC}$ is H;
$R^{DD}$ is Me.

53. A compound according to statement 22, wherein:
$R^{AA}$ is Cl;
$R^{BB}$ is H;
$R^{CC}$ is H;
$R^{DD}$ is Br.

54. A compound according to statement 22, wherein:
$R^{AA}$ is Br;
$R^{BB}$ is H;
$R^{CC}$ is H;
$R^{DD}$ is H.

55. A compound according to statement 22, wherein:
$R^{AA}$ is Cl;
$R^{BB}$ is H;
$R^{CC}$ is H;
$R^{DD}$ is F.

56. A compound according to statement 22, wherein:
$R^{AA}$ is Cl;
$R^{BB}$ is H;
$R^{CC}$ is H;
$R^{DD}$ is OMe.

57. A compound according to statement 22, wherein:
$R^{AA}$ is Br;
$R^{BB}$ is H;
$R^{CC}$ is H;
$R^{DD}$ is F.

58. A compound according to statement 22, wherein:
$R^{AA}$ is OMe;
$R^{BB}$ is H;
$R^{CC}$ is H;
$R^{DD}$ is H.

59. A compound according to statement 11, wherein:
$R^A$ is $CF_3$;
$R^B$ is H;
$R^C$ is H;
$R^D$ is H.

60. A compound according to statement 11, wherein:
$R^A$ is $CH_3$;
$R^B$ is H;
$R^C$ is H;
$R^D$ is H.

61. A compound according to any one of statements 1 to 60, wherein $R^{C11}=R^{C1}$, $R^{C13}=R^{C3}$ and $R^{C14}=R^{C4}$.

62. A compound according to any one of statements 1 to 61, wherein $R^{C1}$, $R^{C3}$ and $R^{C4}$ are independently selected from H, Cl, F, Br, Me, OMe, cyano, $CF_3$ and $CH_2OH$.

63. A compound according to any one of statements 1 to 61, wherein $R^{C1}$, $R^{C3}$ and $R^{C4}$ are independently selected from H, Cl, F, $CF_3$, OMe and $CH_2OH$ 64. A compound according to any one of statements 1 to 61, wherein $R^{C1}$, $R^{C3}$ and $R^{C4}$ are independently selected from H, F and OMe.

65. A compound according to any one of statements 1 to 64, wherein two of $R^{C1}$, $R^{C3}$ and $R^{C4}$ are H, and the other is selected from the defined groups, except H.

66. A compound according to any one of statements 1 to 64, wherein one of $R^{C1}$, $R^{C3}$ and $R^{C4}$ is H, and the other two are independently selected from the defined groups, except H.

67. A compound according to any one of statements 1 to 61, wherein $R^{C1}$, $R^{C3}$ and $R^{C4}$ are H.

68. A compound according to any one of statements 1 to 61, wherein:
$R^{C1}$ is H;
$R^{C3}$ is H; and
$R^{C4}$ is F.

69. A compound according to any one of statements 1 to 61, wherein:
$R^{C1}$ is OMe;
$R^{C3}$ is H; and
$R^{C4}$ is H.

70. A compound according to any one of statements 1 to 69, wherein $R^{C11}$, $R^{C13}$ and $R^{C14}$ are independently selected from H, Cl, F, Br, Me, OMe, cyano, $CF_3$ and $CH_2OH$.

71. A compound according to any one of statements 1 to 69, wherein $R^{C11}$, $R^{C13}$ and $R^{C14}$ are independently selected from H, Cl, F, $CF_3$, OMe and $CH_2OH$.

72. A compound according to any one of statements 1 to 69, wherein $R^{C11}$, $R^{C13}$ and $R^{C14}$ are independently selected from H, F and OMe.

73. A compound according to any one of statements 1 to 72, wherein two of $R^{C11}$, $R^{C13}$ and $R^{C14}$ are H, and the other is selected from the defined groups, except H.

74. A compound according to any one of statements 1 to 72, wherein one of $R^{C11}$, $R^{C13}$ and $R^{C14}$ is H, and the other two are independently selected from the defined groups, except H.

75. A compound according to any one of statements 1 to 69, wherein $R^{C11}$, $R^{C13}$ and $R^{C14}$ are H.

76. A compound according to any one of statements 1 to 69, wherein:
$R^{C11}$ is H;
$R^{C13}$ is H; and
$R^{C14}$ is F.

77. A compound according to any one of statements 1 to 69, wherein:
$R^{C11}$ is OMe;
$R^{C13}$ is H; and
$R^{C14}$ is H.

78. A compound according to any one of statements 1 to 77, wherein Y is $(CH_2)_n$, where n is from 2 to 3.

79. A compound according to any one of statements 1 to 77, wherein Y is $(CH_2)_2$.

80. A compound according to any one of statements 1 to 77, wherein Y is $(CH_2)_3$.

81. A compound according to any one of statements 1 to 77, wherein Y is $(CH_2)_4$.

82. A compound according to any one of statements 1 to 81, wherein $W^1$ and $W^{11}$ are OH.

83. A compound according to any one of statements 1 to 82, wherein $W^1$ and $W^{11}$ are $OR^P$, where $R^P$ is Me or Et.

84. A compound as defined in any one of statements 1 to 83, for use in a method of therapy.

85. A pharmaceutical composition comprising a compound as defined in any one of statements 1 to 83, and a pharmaceutically acceptable excipient.

86. A method of treatment or prevention of a disease ameliorated by the modulation of STING, comprising administering to a patient in need of treatment, a compound as defined in any one of statements 1 to 83, or a pharmaceutical composition according to statement 85.

87. The use of a compound as defined in any one of statements 1 to 83, in the manufacture of a medicament for treating or preventing disease ameliorated by the modulation of STING.

89. A compound as defined in any one of statements 1 to 83, or pharmaceutical composition according to statement 85 for use in the treatment or preventing of disease ameliorated by the modulation of STING.

|  | Reference | DOI |
|---|---|---|
| Abraham 1996 | Abraham, R. T. (1996), Current Opinion in Immunology. 8(3), 412-8 | 10.1016/S0952-7915(96)80132-4 |
| Aguirre 2012 | Aguirre, S., et al, PloS Pathog, 2012: 8(10), e1002934 | 10.1371/journal.ppat.1002934 |
| Ashby 1998 | Ashby, M. N. (1998), Current Opinion in Lipidology. 9(2), 99-102 | 10.1097/00041433-199804000-00004 |
| Bolen 1997 | Bolen, J. B., Brugge, J. S., (1997) Annual review of Immunology. 15: 371-404 | 10.1146/annurev.immunol.15.1.371 |
| Brekken 2000 | Brekken, R. A. et al, Cancer Res. (2000), 60(18), 5117-5124 | PMID: 11016638 |
| Brodt 2000 | Brodt, P, Samani, A., and Navab, R. (2000), Biochemical Pharmacology, 60, 1101-1107 | 10.1016/S0006-2952(00)00422-6 |
| Burdette 2013 | Burdette, D. L, et al, Nature Immunology, 2013: 14, 19-26 | 10.1038/ni.2491 |
| Cai 2014 | Cai, X., et al, Molecular Cell, 2014: 54, 289-296 | 10.1016/j.molcel.2014.03.040 |
| Canman 1998 | Canman, C. E., Lim, D. S. (1998), Oncogene 17(25), 3301-3308 | 10.1038/sj.onc.1202577 |
| Chen 2014 | Chen, X., et al, Protein & Cell, 2014: 5, 369-381 | 10.1007/s13238-014-0026-3 |
| Chhabra2012 | Chhabra, S., et al, PLoS ONE (2012), 7(1) e29444 | 10.1371/journal.pone.0029444 |
| Cirulli 2015 | Cirulli, E. T., et al, Science, 2015: 347, 1436-1441 | 10.1126/science.aaa3650 |
| Collins 2015 | Collins, A. C., et al, Cell Host & Microbe, 2015: 17, 820-828 | 10.1016/j.chom.2015.05.005 |
| Conlon 2013 | Conlon, J., et al, J. Immunol. 2013: 190, 5216-5225 | 10.4049/jimmunol.1300097 |
| Corrales 2015 | Corrales, L, et al, Clin. Cancer Res., 2015: 21,4774-4779 | 10.1158/1078-0432.CCR-15-1362 |
| Crow 2006 | Crow, Y. J., et al, Nat Genet., 2006: 38, 917-920 | 10.1038/ng1845 |
| Diner 2013 | Diner, E. J., et al, Cell Reports, 2013: 3, 1355-1361 | 10.1016/j.celrep.2013.05.009 |
| Ding 2013 | Ding, Q., et al, J. Hepatol., 2013: 59, 52-58 | 10.1016/j.jhep.2013.03.019 |
| Dubensky 2013 | Dubensky, T. W., et al, Ther. Adv. Vaccines, 2013: 1, 131-134 | 10.1177/2051013613501988 |
| Freischmidt 2015 | Freischmidt, A., et al, Nat. Neurosci., 2015: 18, 631-636 | 10.1038/nn.4000 |
| Gao 2013A | Gao, P., et al, Cell, 2013: 153, 1094-1107 | 10.1016/j.cell.2013.04.046 |
| Gao 2013B | Gao, D., et al, Science, 2013: 341, 903-906 | 10.1126/science.1240933 |
| Gao 2013C | Gao, P., et al, Cell, 2013: 154, 748-762 | 10.1016/j.cell.2013.07.023 |
| Green 2000 | Green, M. C. et al, Cancer Treat. Rev., (2000), 26(4), 269-286 | 10.1053/ctrv.2000.0176 |
| Herzner2015 | Herzner, A.-M., et al, Nat Immunol., 2015, 16, 1025-1033 | 10.1038/ni.3267 |
| Holm 2016 | Holm, C. K., et al, Nat. Comm., 2016: 7, 10680 | 10.1038/ncomms10680 |
| Huber 2010 | Huber, J. P., et al, J. Immunol., 2010: 185, 813-817 | 10.4049/jimmunol.1000469 |
| Hutloff 1999 | Hutloff, A., et al, Nature (1999), 397: 263-266 | 10.1038/16717 |
| Isaacs 1957 | Isaacs, A., et al, Proc. R. Soc. Lon. Ser. B. Biol. Sci., 1957: 147, 258-267 | 10.1098/rspb.1957.0048 |
| Ishikawa 2008 | Ishikawa, H., et al, Nature, 2008: 455, 674-678 | 10.1038/nature07317 |
| Ishikawa 2009 | Ishikawa, H., et al, Nature, 2009: 461, 788-792 | 10.1038/nature08476 |
| Jackson 1997 | Jackson, S. P. (1997), International Journal of Biochemistry and Cell Biology. 29(7): 935-8 | 10.1016/S1357-2725(97)00006-X |
| Jin 2011A | Jin, L, et al, J. Immunol., 2011: 187, 2595-2601 | 10.4049/jimmunol.1100088 |

| Reference | | DOI |
|---|---|---|
| Jin 2011B | Jin, L, et al, Genes and Immunity, 2011: 12, 263-269 | 10.1038/gene.2010.75 |
| Kath 2000 | Kath, J. C., Exp. Opin. Then Patents (2000) 10(6):803-818 | 10.1517/13543776.10.6.803 |
| Karlsson 2006 | Karlsson, R., et al., Anal. Biochem., 2006, 349, 136-147. | 10.1016/j.ab.2005.09.034 |
| Lackey 2000 | Lackey, K. et al, Bioorganic and Medicinal Chemistry Letters, 10(3), 2000, 223-226 | 10.1016/S0960-894X(99)00668-X |
| Lau 2013 | Lau, L, et al, Science, 2013: 350, 568-571 | 10.1126/science.aab3291 |
| Lemos 2014 | Lemos, H., et al, J. Immunol., 2014: 192, 5571-5578 | 10.4049/jimmunol.1303258 |
| Lemos 2016 | Lemos, H., et al, Cancer Res. (2016), 76(8), 2076-81 | 10.1158/0008-5472.CAN-15-1456 |
| Libanova 2012 | Libanova, R., et al, Microbial Biotechnology, 2012: 5, 168-176 | 10.1111/j.1751-7915.2011.00306.x |
| Liu 2016 | Liu, Y., et al, J. Virol., 2016: 90, 9406-9419 | 10.1128/J VI.00748-16 |
| Lofts 1994 | Lofts, F. J., et al, "Growth factor receptors as targets", New Molecular Targets for Cancer Chemotherapy, ed. Workman, Paul and Kerr, David, CRC press 1994, London | ISBN 9780849349058 |
| Ma 2015 | Ma, Z., et al, PNAS, 2015: 112, E4306-E4315 | 10.1073/pnas.1503831112 |
| Ma 2016 | Ma, Z., et al, Cell Host & Microbe, 2016: 19, 150-158 | 10.1016/j.chom.2016.01.010 |
| Martnez-Lacaci 2000 | Martnez-Lacaci, L, et al, Int. J. Cancer (2000), 88(1), 44-52 | 10.1002/1097-0215(20001001 )88:1<44::AID-IJC7>3.0.CO;2-8 |
| Massague 1996 | Massague, J., Weis-Garcia, F. (1996) Cancer Surveys "Cell Signalling". 27:41-64 | ISBN: 9780879694845 |
| McNab 2015 | McNab, F., et al, Nat. Rev. Immunol., 2015: 15, 87-103 | 10.1038/nri3787 |
| Moisan 2006 | Moisan, J., et al, Am. J. Physiol. Lung Cell Mol. Physiol., 2006: 290, L987-L995 | 10.1152/ajplung.00440.2005 |
| Munn 2016 | Munn, D. H., et al, Trends Immunol. (2016), 37(3), 193-207 | 10.1016/j.it.2016.01.002 |
| Niesen 2007 | Niesen, F. H., et al, Nat. Protoc. (2007), 2(9), 2212-2221 | 10.1038/nprot.2007.321 |
| Nitta 2013 | Nitta, S., et al, Hepatology, 2013: 57, 46-58 | 10.1002/hep.26017 |
| Oliff 1999 | Oliff, A. (1999), Biochim. Biophys. Acta, 1423(3), 19-30 | 10.1016/S0304-419X(99)00007-4 |
| Papalia 2006 | Papalia, G. A., et al, Anal. Biochem. (2006), 359, 94-105 | 10.1016/j.ab.2006.08.021 |
| Paulos 2010 | Paulos, C. M., et al, Sci Transl Med (2010), 2(55); 55ra78 | 10.1126/scitranslmed.3000448 |
| Persing 2002 | Persing, D. H., et al, Trends Microbiol., 2002: 10(10 Suppl), S32-S37 | 10.1016/S0966-842X(02)02426-5 |
| Philip 1995 | Philip, P. A., and Harris, A. L. (1995), Cancer Treatment and Research. 78: 3-27 | 10.1007/978-1-4615-2007-8_1 |
| Powis 1994 | Powis, G., and Kozikowski A., (1994) New Molecular Targets for Cancer Chemotherapy ed., Paul Workman and David Kerr, CRC press 1994, London, 81-96 | ISBN: 9780849349058 |
| Prantner2010 | Prantner, D., et al, J. Immunol., 2010: 184, 2551-2560 | 10.4049/jimmunol.0903704 |
| Rakoff-Nahoum 2004 | Rakoff-Nahoum, S., et al, Cell, 2004: 118, 229-241 | 10.1016/j.cell.2004.07.002 |
| Ramanjulu 2018 | Ramanjulu J., et al., Nature, 2018, 564, 439-443 | 10.1038/S41586-018-0705-y |
| Rosa 2015 | Rosa, N., et al, J. Biomol. Screen. 2015, 20(7) 898-905 | 10.1177/1087057115584059 |
| Rosania 2000 | Rosania, G. R., et al, Exp. Opin. Then Patents (2000), 10(2), 215-230 | 10.1517/13543776.10.2.215 |
| Scharovsky 2000 | Scharovsky, O. G., et al, (2000), Journal of Biomedical Science. 7(4), 292-8 | 10.1159/000025462 |

-continued

| Reference | | DOI |
|---|---|---|
| Seabrook & Newman 2013 | Seabrook, S. A. and Newman, J., ACS Comb. Sci. (2013), 15, 387-392 | 10.1021/co400013v |
| Sharma 2011 | Sharma, S., et al, Immunity, 2011: 35, 194-207 | 10.1016/j.immuni.2011.05.016 |
| Shawver 1997 | Shawver et al, DDT Vol 2, No. 2 February 1997 (50-63) | 10.1016/S1359-6446(96) 10053-2 |
| Sinh 1999 | Sinh, S. and Corey, S.J., (1999) Journal of Hematotherapy and Stem Cell Research 8(5): 465-80 | 10.1089/152581699319920 |
| Smithgall 1995 | Smithgall, T. E. (1995), Journal of Pharmacological and Toxicological Methods. 34(3) 125-32 | 10.1016/1056-8719(95)00082-7 |
| Stern 2000 | Stern, D. F., Breast Cancer Res. (2000), 2(3), 176-183 | 10.1186/bcr51 |
| Stetson 2008 | Stetson, D. B., et al, Cell, 2008: 134, 587-598 | 10.1016/j.cell.2008.06.032 |
| Storek 2015 | Storek, K. M., et al, J. Immunol., 2015: 194, 3236-3245 | 10.4049/jimmunol.1402764 |
| Sun 2012 | Sun, L, et al, PloS One, 2012: 7(2), e30802 | 10.1371/journal.pone.0030802 |
| Takeuchi 2010 | Takeuchi, O., et al, Cell, 2010: 140, 805-820 | 10.1016/j.cell.2010.01.022 |
| Wakamatsu 2013 | Wakamatsu, E., et al, PNAS USA (2013), 110(3), 1023-8 | 10.1073/pnas.1220688110 |
| Wassermann 2015 | Wassermann, R., et al, Cell Host & Microbe, 2015: 17, 799-810 | 10.1016/j.chom.2015.05.003 |
| Watson 2015 | Watson, R. O., et al, Cell Host& Microbe, 2015: 17, 811-819 | 10.1016/j.chom.2015.05.004 |
| Wu 2015 | Wu, J.-J. et al, Cell Host& Microbe, 2015: 18, 333-344 | 10.1016/j.chom.2015.07.015 |
| Yamamoto 1999 | Yamamoto, T., Taya, S., Kaibuchi, K., (1999), Journal of Biochemistry. 126(5) 799-803 | 10.1093/oxfordjournals.jbchem.a022519 |
| Yao 2011 | Yao, S., et al, Immunity (2011), 34(5), 729-40 | 10.1016/j.immuni.2011.03.014 |
| Yi 2013 | Yi, G., et al, PLOS One, 2013: 8(10), e77846 | 10.1371/journal.pone.0077846 |
| Zender 2013 | Zender, M., et al, J. Med. Chem. (2013), 56, 6761-6774 | 10.1021/jm400830r |
| Zhong 2000 | Zhong, H. et al, Cancer Res, (2000), 60(6), 1541-1545 | PMID: 10749120 |
| Zitvogel 2015 | Zitvogel, L, et al, Nature Reviews Immunology, 2015, 15, 405-414 WHO Drug Information, Vol. 27, No. 1, pages 68-69 (2013) WHO Drug Information, Vol. 27, No. 2, pages 161-162 (2013) | 10.1038/nri3845 |
| | Patents | |
| | GB2563642A | |
| | EP1065213 | |
| | EP1125585 | |
| | EP1374901 | |
| | EP1374902 | |
| | US2005/0176701 | |
| | US2011/0271358 | |
| | US2011/0280877 | |
| | US2013/0034559 | |
| | US2013/0045201 | |
| | US2013/0045201 | |
| | US2014/0341902 | |
| | US2015/0274835 | |
| | US2016/0215059 | |
| | US2016/0304610 | |
| | US2018/0093964 | |
| | US5681835 | |
| | US5877219 | |
| | US6113918 | |
| | US6207716 | |
| | US6268391 | |
| | US6525028 | |
| | US6911434 | |
| | US6984720 | |
| | US7129219 | |
| | US7488802 | |

| Reference | DOI |
|---|---|
| US7504101 | |
| US7521051 | |
| US7550140 | |
| US7595048 | |
| US7605238 | |
| US7758852 | |
| US7858765 | |
| US7943743 | |
| US7960515 | |
| US8008449 | |
| US8034953 | |
| US8168179 | |
| US8168757 | |
| US8217149 | |
| US8217149 | |
| US8354509 | |
| US8383796 | |
| US8552154 | |
| US8779108 | |
| US8779108 | |
| US9212224 | |
| WO01/47883 | |
| WO2001/090129 | |
| WO02/04425 | |
| WO02/74769 | |
| WO2002/057245 | |
| WO2002/057287 | |
| WO2003/000254 | |
| WO2003/007945 | |
| WO2003/085375 | |
| WO2003/095441 | |
| WO2004/004771 | |
| WO2004/037818 | |
| WO2004/054581 | |
| WO2004/054974 | |
| WO2004/055010 | |
| WO2004/055011 | |
| WO2004/055012 | |
| WO2004/055016 | |
| WO2004/056875 | |
| WO2004/064925 | |
| WO2004/065367 | |
| WO2004/072286 | |
| WO2004/074270 | |
| WO2005/014543 | |
| WO2005/080388 | |
| WO2005/087238 | |
| WO2005/105761 | |
| WO2006/016997 | |
| WO2006/018725 | |
| WO2006/020082 | |
| WO2006/045613 | |
| WO2006/122011 | |
| WO2007/005874 | |
| WO2007/005874 | |
| WO2007/054279 | |
| WO2008/137915 | |
| WO2008/156712 | |
| WO2010/027827 | |
| WO2010/056804 | |
| WO2010/077634 | |
| WO2011/066342 | |
| WO2011/066389 | |
| WO2012/027328 | |
| WO2012/131004 | |
| WO2013/019906 | |
| WO2013/028231 | |
| WO2013/166000 | |
| WO2013/185052 | |
| WO2014/033327 | |
| WO2014/055897 | |
| WO2014/093936 | |
| WO2014/189805 | |
| WO2015/077354 | |
| WO2015/185565 | |
| WO2016/007235 | |
| WO2016/120789 | |

| Reference | DOI |
|---|---|
| WO2017/175147 | |
| WO2017/175156 | |
| WO2018/234805 | |
| WO2018/234807 | |
| WO2018/234808 | |
| WO2019/069269 | |
| WO2019/027858 | |
| WO2019/069270 | |
| WO2019/165032 | |
| WO2019/195063 | |
| WO2019/195124 | |
| WO 2019/219820 | |

The invention claimed is:

1. A compound of formula I:

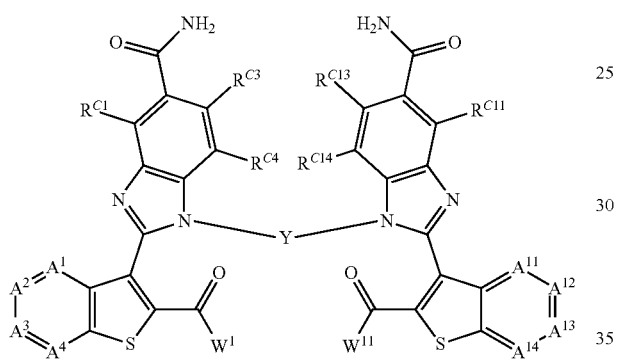

(I)

wherein:
Y is $(CH_2)_n$, where n is from 2 to 4;
$W^1$ and $W^{11}$ are independently selected from OH and $OR^P$, where $R^P$ is Me or Et;
$A^1$ is $CR^A$ or N;
$A^2$ is $CR^B$ or N;
$A^3$ is $CR^C$ or N;
$A^4$ is $CR^D$ or N;
where no more than two of $A^1$, $A^2$, $A^3$, and $A^4$ may be N;
one or two of $R^A$, $R^B$, $R^C$ and $R^D$, (if present) are selected from H, F, Cl, Br, Me, $CF_3$, cyclopropyl, cyano, OMe, OEt, $CH_2OH$, $CH_2OMe$ and OH;
the remainder of $R^A$, $R^B$, $R^C$ and $R^D$, (if present) are H;
$A^{11}$ is $CR^{AA}$ or N;
$A^{12}$ is $CR^{BB}$ or N;
$A^{13}$ is $CR^{CC}$ or N;
$A^{14}$ is $CR^{DD}$ or N;
where no more than two of $A^{11}$, $A^{12}$, $A^{13}$ and $A^{14}$ may be N;
one or two of $R^{AA}$, $R^{BB}$, $R^{CC}$ and $R^{DD}$, (if present) are selected from H, F, C, Br, Me, $CF_3$, cyclopropyl, cyano, OMe, OEt, $CH_2OH$, $CH_2OMe$ and OH;
the remainder of $R^{AA}$, $R^{BB}$, $R^{CC}$ and $R^{DD}$, (if present) are H;
$R^{C1}$, $R^{C3}$ and $R^{C4}$ are independently selected from H, Cl, F, Br, Me, OMe, OEt, cyano, $CF_3$, $CH_2OH$, $CH_2OMe$, $C_{2-4}$ alkenyl and $C_5$ heterocyclyl;
$R^{C11}$, $R^{C13}$ and $R^{C14}$ are independently selected from H, Cl, F, Br, Me, OMe, OEt, cyano, $CF_3$, $CH_2OH$, $CH_2OMe$, $C_{2-4}$ alkenyl and $C_5$ heterocyclyl.

2. A compound according to claim 1, wherein $A^{11}=A^1$, $A^{12}=A^2$, $A^{13}=A^3$, $A^{14}=A^4$, $R^{C11}=R^{C1}$, $R^{C13}=R^{C3}$, $R^{C14}=R^{C4}$, $W^{11}=W^1$.

3. A compound according to claim 1 or 2, wherein $A^1$ is $CR^A$, $A^2$ is $CR^B$, $A^3$ is $CR^C$, and $A^4$ is $CR^D$.

4. A compound according to claim 1, wherein $A^{11}$ is $CR^{AA}$, $A^{12}$ is $CR^{BB}$, $A^{13}$ is $CR^{CC}$, and $A^{14}$ is $CR^{DD}$.

5. A compound according to claim 1 wherein the compound is selected from formulae IIIb, IIIc, IIId and IIIe:

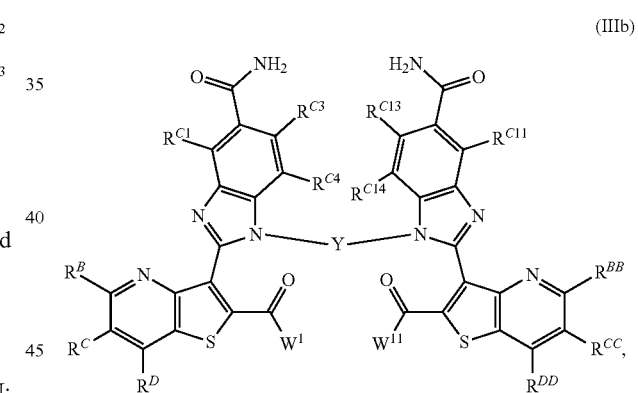

(IIIb)

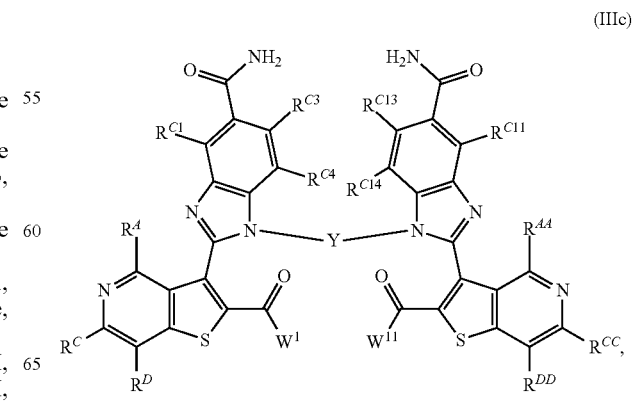

(IIIc)

-continued (IIId)

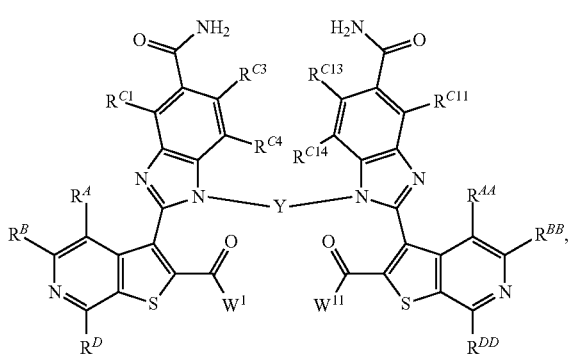

(IIIe)

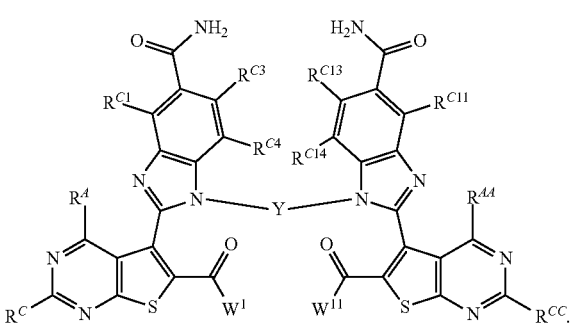

6. A compound according to claim 1, wherein:
$R^A$ (if present) is selected from Cl, Br and OMe:
$R^B$ (if present) is H;
$R^C$ (if present) is H;
$R^D$ (if present) is selected from H, F, Br, Me and OMe.

7. A compound according to claim 1, wherein $A^1$, $A^2$, $A^3$ and $A^4$ are selected from combinations 1-10:

| Combination | $A^1$ | $A^2$ | $A^3$ | $A^4$ |
| --- | --- | --- | --- | --- |
| 1 | CCl | CH | CH | CH |
| 2 | CCl | CH | CH | CCH$_3$ |
| 3 | CCl | CH | CH | CBr |
| 4 | CBr | CH | CH | CH |
| 5 | CCl | CH | CH | CF |
| 6 | CCl | CH | CH | C—OCH$_3$ |
| 7 | CBr | CH | CH | CF |
| 8 | C—OCH$_3$ | CH | CH | CH |
| 9 | CCF$_3$ | H | H | H |
| 10 | CCH$_3$ | H | H | H. |

8. A compound according to claim 1, wherein:
$R^{AA}$ (if present) is selected from Cl, Br and OMe;
$R^{BB}$ (if present) is H;
$R^{CC}$ (if present) is H;
$R^{DD}$ (if present) is selected from H, F, Br, Me and OMe.

9. A compound according to claim 1, wherein $A^{11}$, $A^{12}$, $A^{13}$ and $A^{14}$ are selected from combinations 1-10:

| Combination | $A^{11}$ | $A^{12}$ | $A^{13}$ | $A^{14}$ |
| --- | --- | --- | --- | --- |
| 1 | CCl | CH | CH | CH |
| 2 | CCl | CH | CH | CCH$_3$ |
| 3 | CCl | CH | CH | CBr |
| 4 | CBr | CH | CH | CH |
| 5 | CCl | CH | CH | CF |
| 6 | CCl | CH | CH | C—OCH$_3$ |
| 7 | CBr | CH | CH | CF |
| 8 | C—OCH$_3$ | CH | CH | CH |
| 9 | CCF$_3$ | H | H | H |
| 10 | CCH$_3$ | H | H | H. |

10. A compound according to claim 1, wherein $R^{C11}=R^{C1}$, $R^{C13}=R^{C3}$ and $R^{C14}=R^{C4}$.

11. A compound according to claim 10, wherein $A^1$, $A^2$, $A^3$, $A^4$, $A^{11}$, $A^{12}$, $A^{13}$ and $A^{14}$ are selected from combinations 1, 4, 9 and 10:

| Combination | $A^1/A^{11}$ | $A^2/A^{12}$ | $A^3/A^{13}$ | $A^4/A^{14}$ |
| --- | --- | --- | --- | --- |
| 1 | CCl | CH | CH | CH |
| 4 | CBr | CH | CH | CH |
| 9 | CCF$_3$ | H | H | H |
| 10 | CCH$_3$ | H | H | H. |

12. A compound according to claim 1, wherein $R^{C1}$, $R^{C3}$ and $R^{C4}$ are selected from combinations 1-3:

| Combination | $R^{C1}$ | $R^{C3}$ | $R^{C4}$ |
| --- | --- | --- | --- |
| 1 | H | H | H |
| 2 | H | H | F |
| 3 | OMe | H | H. |

13. A compound according to claim 1, wherein $R^{C11}$, $R^{C13}$ and $R^{C14}$ are selected from combinations 1-3:

| Combination | $R^{C11}$ | $R^{C13}$ | $R^{C14}$ |
| --- | --- | --- | --- |
| 1 | H | H | H |
| 2 | H | H | F |
| 3 | OMe | H | H. |

14. A compound according to claim 1, wherein Y is $(CH_2)_n$, where n is from 2 to 3.

15. A compound according to claim 1, wherein Y is $(CH_2)_2$.

16. A compound according to claim 1, wherein $W^1$ and $W^{11}$ are OH.

17. A pharmaceutical composition comprising a compound as defined in claim 1, and a pharmaceutically acceptable excipient.

* * * * *